(12) United States Patent
Ray

(10) Patent No.: US 11,375,926 B2
(45) Date of Patent: *Jul. 5, 2022

(54) SYSTEMS, DEVICES, AND METHODS FOR PERFORMING TRANS-ABDOMINAL FETAL OXIMETRY AND/OR TRANS-ABDOMINAL FETAL PULSE OXIMETRY USING A HEARTBEAT SIGNAL FOR A PREGNANT MAMMAL

(71) Applicant: Raydiant Oximetry, Inc., Mountain View, CA (US)

(72) Inventor: Neil Padharia Ray, Sacramento, CA (US)

(73) Assignee: RAYDIANT OXIMETRY, INC., San Ramon, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 16/521,431

(22) Filed: Jul. 24, 2019

(65) Prior Publication Data

US 2019/0343437 A1 Nov. 14, 2019

Related U.S. Application Data

(63) Continuation-in-part of application No. 15/973,141, filed on May 7, 2018, now Pat. No. 10,362,974.
(Continued)

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0011* (2013.01); *A61B 5/01* (2013.01);
(Continued)

(58) Field of Classification Search
CPC ... A61B 5/0011; A61B 5/0205; A61B 5/1455; A61B 5/14551; A61B 5/14552;
(Continued)

(56) References Cited

U.S. PATENT DOCUMENTS 4,911,167 A 3/1990 Corenman et al.
5,348,002 A 9/1994 Caro
(Continued)

FOREIGN PATENT DOCUMENTS

CN 103381094 A 11/2013
EP 1054620 B1 1/2010
(Continued)

OTHER PUBLICATIONS

Steven A. Julious, Sample size of 12 per group rule ofthumb for a pilot study, Pharmaceut. Statist. 2005, 4, pp. 287-291, 2005.
(Continued)

*Primary Examiner* — Chu Chuan Liu
(74) *Attorney, Agent, or Firm* — Resonance IP Law, PC

(57) ABSTRACT

Light reflected from a pregnant woman's abdomen and fetus contained therein that has been received by a detector and converted into a reflected electronic signal may be received by a processor. A portion of the reflected electronic signal that is reflected from the fetus may be isolated and the isolated portion of the reflected electronic signal may be analyzed to determine a fetal hemoglobin oxygen saturation level of the fetus. The isolation may be achieved by synchronizing the reflected electronic signal with a fetal heartbeat signal and multiplying the synchronized reflected electronic signal by the synchronized fetal heartbeat signal.

23 Claims, 28 Drawing Sheets

Related U.S. Application Data which is a continuation of application No. 15/698,954, filed on Sep. 8, 2017, now Pat. No. 9,968,286, which is a continuation of application No. 15/393,752, filed on Dec. 29, 2016, now Pat. No. 9,757,058.

(60) Provisional application No. 62/273,196, filed on Dec. 30, 2015.

(51) Int. Cl.

| | |
|---|---|
| *A61B 8/08* | (2006.01) |
| *A61B 5/145* | (2006.01) |
| *A61B 5/1482* | (2006.01) |
| *A61B 8/00* | (2006.01) |
| *A61B 5/01* | (2006.01) |
| *A61B 5/0205* | (2006.01) |
| *A61B 5/1464* | (2006.01) |
| *A61B 5/024* | (2006.01) |
| *A61B 8/02* | (2006.01) |

(52) U.S. Cl.
CPC ........ *A61B 5/02055* (2013.01); *A61B 5/1464* (2013.01); *A61B 5/1482* (2013.01); *A61B 5/14546* (2013.01); *A61B 5/4356* (2013.01); *A61B 8/4483* (2013.01); *A61B 8/488* (2013.01); *A61B 8/56* (2013.01); *A61B 5/02411* (2013.01); *A61B 5/4362* (2013.01); *A61B 8/02* (2013.01); *A61B 8/0866* (2013.01)

(58) Field of Classification Search
CPC . A61B 5/14546; A61B 5/4356; A61B 5/0059; A61B 5/72; A61B 5/488; A61B 5/1482; A61B 5/4483; A61B 5/01; A61B 5/02055; A61B 5/1464; A61B 5/02411; A61B 5/4362
See application file for complete search history.

(56) References Cited

U.S. PATENT DOCUMENTS

| | | |
|---|---|---|
| 5,807,271 A | 9/1998 | Tayebi et al. |
| 5,835,558 A | 11/1998 | Maschke |
| 6,498,942 B1 | 12/2002 | Esenaliev et al. |
| 6,690,958 B1 | 2/2004 | Walker et al. |
| 7,047,055 B2 | 5/2006 | Boas et al. |
| 7,469,158 B2 | 12/2008 | Cutler et al. |
| 7,515,948 B1 | 4/2009 | Balberg et al. |
| 8,275,436 B2 | 9/2012 | Wang et al. |
| 8,644,900 B2 | 2/2014 | Balberg et al. |
| 9,757,058 B2 | 9/2017 | Ray |
| 9,968,286 B2 | 5/2018 | Ray |
| 10,362,974 B2 | 7/2019 | Ray |
| 2003/0073910 A1 | 4/2003 | Chance |
| 2004/0116789 A1 | 6/2004 | Boas et al. |
| 2005/0280531 A1 | 12/2005 | Fadem et al. |
| 2006/0122475 A1 | 6/2006 | Balberg et al. |
| 2008/0208009 A1 | 8/2008 | Shklarski |
| 2009/0281402 A1 | 11/2009 | Chance |
| 2010/0081901 A1 | 4/2010 | Buice et al. |
| 2011/0218413 A1 | 9/2011 | Wang et al. |
| 2012/0190946 A1 | 7/2012 | Bemreuter |
| 2013/0338460 A1 | 12/2013 | He et al. |
| 2015/0099950 A1 | 4/2015 | Al-Ali et al. |
| 2016/0015304 A1 | 1/2016 | Esenaliev et al. |
| 2016/0128594 A1 | 5/2016 | Amir et al. |
| 2017/0188920 A1 | 7/2017 | Ray |
| 2018/0070871 A1 | 3/2018 | Ray |
| 2019/0343437 A1 | 11/2019 | Ray |

FOREIGN PATENT DOCUMENTS

| | | |
|---|---|---|
| WO | 2004086966 A1 | 10/2004 |
| WO | 2009032168 A1 | 3/2009 |
| WO | 2018094391 A3 | 7/2018 |

OTHER PUBLICATIONS

Steven L Jacques, Optical properties of biological tissues: a review, IOP Publishing, Phys. Med. Biol. 58, pp. 5007-5008 and R37-R61, 41452.

Stipcevic; et al., "Characterization of a novel avalanche photodiode for single photon detection in VIS-NIR range", Optics Express (Aug. 2, 2010), 18(16):17448-17459.

Strangman et al., "Factors affecting the accuracy of near-infrared spectroscopy concentration calculations for focal changes in oxygenation parameters," NeuroImage 18 (2003) 865-879.

Subramaniam, "An IR Muscle Contraction Sensor", Cornell University, student project (last modified Jun. 10, 2014), fetrieved from: https://people.ece.cornell.edu/land/courses/eceprojectsland/STUDENTPROJ/2013to2014/ras578/Writeup/An%20IR%20Muscle%20Contraction%20Sensor.html, 6 pgs.

Sutin, Jason, et al., "Time-domain diffuse correlation spectroscopy," Optica, vol. 3, Issue 9, pp. 1006-1013 (2016), https://doi.org/10.1364/OPTICA.3.001006.

SVB, Silicon Valley Bank , Trends in Healthcare Investments and Exits 2018, SVB, Silicon Valley Bank, Annual report 2018, pp. 1 to 34, 2018.

Tamborini et al., Development and characterization of a multi distance and multi wave length diffuse correlation spectroscopy system, Neurophotonics 5(1), 011015 (Jan.-Mar. 2018).

Tao Tu, Yu Chen, Britton Chance, An Analytical Model for Optimization of Frequency-domain System, Bioengineering Conference, 2002. Proceedings of the IEEE 28th Annual Northeast, pp. 79-80, 2002.

Themelis et al., Near-infrared spectroscopy measurement of the pulsatilecomponent of cerebral blood flow and volume from arterialoscillations, Journal of Biomedical Optics, pp. 15, 2007.

Thomas P. Sartwelle, James C. Johnston and Berna Arda, A half century of electronic fetalmonitoring and bioethics: silence speakslouder than words, Maternal Health, Neonatology,and Perinatology (2017) 3:21, pp. 1 to 8, 2017.

Tomich, Paul G., "Fetal heart rate monitoring," Power Point—Department of Obstetrics and Gynecology, University of Nebraska College of Medicine, (uploaded Jul. 30, 2014) 69 pages.

Torbenson et al., Intrapartum factors associated with neonatal hypoxic ischemic encephalopathy: a case-controlled study, BMC Pregnancy and Childbirth, pp. 7, 2017.

Truven Health Analytics, The cost of having a baby in the United States, Truven Health Analytics Marketscan® Study, pp. 1 to 84, 2014.

Tu; et al., "An Analytical Model for Optimization of Frequency-domain System", Bioengineering Conference, 2002. Proceedings of the IEEE 28th Annual Northeast (Apr. 21, 2002), pp. 79-80.

Uchida, Toshiyuki et al., "Reevaluation of intrapartum fetal monitoring using fetal oximetry: A review," The Journal of Obstetrics and Gynaecology Research, 8 page(s), Jun. 22, 2018.

Ultman and Piantadosi, "Differential Pathlength Factor for Diffuse Photon Scattering Through Tissue by a Pulse-Response Method," Mathematical Biosciences, pp. 10, 1991.

Valverde et al, Effectiveness of pulse oximetry versus fetal electrocardiography for the intrapartum evaluation of non reassuring fetal heart rate, European Journal of Obstetric and Gynecology and Reproductive Biology, pp. 5, 2011.

Verkruysse, et al., "Calibration of Contactless Pulse Oximetry", Anesthesia and Analgesia (Jan. 2017), 124(1):136-145.

Victoria G. Woo et al., Achieving higher-value obstetrical care, American Journal of Obstetrics&Gynecology, pp. 14, 42795.

Vintzileos et al., "Transabdominal fetal pulse oximetry with near-infrared spectroscopy," American Journal of Obstetrics and Gynecology (2005), pp. 129-133.

(56) References Cited

OTHER PUBLICATIONS

Vishnoi, et al., "Photon migration through fetal head in utero using continuous wave, near-infrared spectroscopy: development and evaluation of experimental and numerical models", Journal of Biomedical Optics (Apr. 2000), 5(2):163-172.
W. G. Zijistra, A. Buursma, and W.P. Meeuwsen-Van Der Roest, Absorption Spectra of Human Fetal and Adult Oxyhemoglobin, De-Oxyhemoglobin,Carboxyhemoglobin, and Methemoglobin, Clinical chemistry, vol. 37, No. 9, 1991, pp. 1633-1638, 1991.
Weyrich et al., Development of a Phantom to Modulate the Maternal and Fetal Pulse Curve for Pulse Oximetry Measurements, Biomed Tech 2012; 57 , pp. 803-806, 2012.
XP the Xperts in Power , 400-2500 Watts fleX, 400-2500 Watts fleXPower Series, Product information sheet, xppower.com, 10 page(s).
Yamaleyeva et al., Photoacoustic imaging for in vivo quantification of placental oxygenation in mice, The FASEB Journal, vol. 31, No. 12, pp. 5520-5529, 43101.
Yan et al., "Reduction of motion artifact in pulse oximetry by smoothed pseudo Wigner-Ville distribution," Journal of NeuroEngineering and Rehabilitation, 2005, 9 pages.
Yousefi et al., Adaptive Cancellation of Motion Artifact in Wearable Biosensors, 34th Annual International Conference of the IEEE EMBS, San Diego, California USA, Aug. 28-Sep. 1, 2012, 5 pages.
Yuan et al., Motion Artefact Minimisation from Photoplethysmography based Non-invasive Hemoglobin Sensor by the Envelope Method, Measurements, pp. 19, 2018.
Zhang et al., Adaptive filtering for global interference cancellation and real-time recovery of evoked brain activity: a Monte Carlo simulation study, Journal of Biomedical Optics, p. 12, Jul./Aug. 2007.
Zhao, Jun, et al., "In vivo determination of the optical properties of infant brain using frequency-domain near-infrared spectroscopy," Journal of Biomedical Optics 10(2), 024028 (Mar./Apr. 2005), p. 024028-1-024028-7, 2005.
Zhao, Yanyu, et al., "Quantitative real-time pulse oximetry with ultrafast frequency-domain diffuse optics and deep neural network processing," Biomedical Optics Express, vol. 9, No. 12, Dec. 1, 2018, 12 pages.
Zourabian, A. et al., "Trans-abdominal monitoring of fetal arterial blood oxygenation using pulse oximetry", Journal of Biomedical Optics (Oct. 2000), 5(4):391-405.
Gregg et al., "Brain specificity of diffuse optical imaging: improvements from superficial signal regression and tomography," Frontiers in NeuroEnergetics, Jul. 2010, vol. 2, Article 14, 8 pages.
Grimes et al., Electronic Fetal Monitoring as a Public Health Screening Program, Obstetrics & Gynecology, vol. 116 No. 6, pp. 1397-1400, 40513.
Harini H. et al., Design and Implementation of a Calibration—Free Pulse Oximeter, IFMBE Proceedings, pp. 4, 2014.
Haydon et al., The effect of maternal oxygen administration onfetal pulse oximetry during labor in fetuses withnonreassuring fetal heart rate patterns, American Journal of Obstetrics and Gynecology (2006) 195 , pp. 735-738, 38897.
Haykin, Kalman filtering and neural networks, John Wiley & Sons, Inc, pp. 298, 2001.
Hiraoka et al., "A Monte Carlo investigation of optical pathlength in inhomogeneous tissue and its application to near-infrared spectroscopy," Phys. Med. Biol. 38 (1993) 1859-1876.
ICNIRP Guidelines on Limits of Exposure to Incoherent Visible and Infrared Radiation, (International Commission on Non-Ionizing Radiation Protection), Health Physics, 105(1):74-96; Jul. 2013.
International Search Report and Written Opinion dated Mar. 13, 2017, from the International Searching Authority, for International Patent Application No. PCT/US2016/068994 (filed Dec. 28, 2016), 13 pages.
Jason S. Robins, Mergers & Acquisitions in the Medical Device Industry:An Exploration of Factors Influencing Valuation, Massachusetts Institute of Technology Libraries, pp. 1 to 85, 39680.

John W. Severinghaus and Yoshiyuki Honda, History of Blood Gas Analysis. VII. Pulse Oximetry, Journal of Clinicai Monitoring vol. 3 No. 2 Apr. 1987, pp. 135-138, 35521.
Johnson and Lilford, Continuous Intrapartum Measurement of Fetal Oxygen Saturation, The Lancet, pp. 1, 32356, Aug. 27, 1988.
Johnson et al., Fetal monitoring with pulse oximetry, British Journal of Obstetrics and Gynaecology, pp. 6, 1991.
Jonhson N, Johnson VA, Continuous fetal monitoring with a pulse oximeter: a case of cord compression, Am J Obstet Gynecol, vol. 161, No. 5, pp. 1295-1296, 32813, Nov. 1989.
Jumadi et al., "Transabdominal Fetal Pulse Oximeter Using LEDs and Photodiode: A Design Consideration Study," 2015 2nd International Conference on Biomedical Engineering (ICoBE), pp. 1 to 6, 42094.
Jurovata; et al., "Simulation of Photon Propagation in Tissue Using Matlab", Faculty of Materials Science and Technology in Trnava Slovak University of Techology in Bratislava, Research Papers (2013), 21:31-37.
Kainerstorfer, Jana et al., "Optical oximetry of volume-oscillating vascular compartments: contributions from oscillatory blood flow," Journal of Biometrical Optics, vol. 21, No. 10, p. 101408-1-101408-13, 42644.
Kayte Spector-Bagdady et al., Clinician Self-Interestand the Case of Electronic Fetal Monitoring, Hastings Center Report, pp. 16-24, 43070.
Kim et al., Noise reduction of PPG signal during Free Movements Using Adaptive SFLC (scaled Fourier linear combiner) , IFMBE proceedings, pp. 4, 39083.
Klauser et al., Use of fetal pulse oximetry among high-risk women in labor: A randomized clinical trial, American Journal of Obstetrics and Gynecology, 192, pp. 1810-1817, 2005.
Kohl et al., "Determination of the wavelength dependence of the differential pathlength factor from near-infrared pulse signals," Phys. Med. Biol. 43 (1998) 1771-1782.
Komalla, "A new method based on complex EMD for motion artifacts reduction in PPG signals for pulse oximeter application," Jourmal of Engineering Technology, vol. 6, Special Issue on Technology Applications and Innovation, 2017, pp. 187-200.
Lakowicz, Joseph R., et al., Frequency-Domain Measurements of Photon Migration in Tissues, Chemical Physics Letters, vol. 166, No. 3, pp. 246-252, 32927, Feb. 23, 1990.
Laqua; et al., "A phantom with pulsating artificial vessels for non-invasive fetal pulse oximetry", Conf Proc IEEE Eng Med Biol Soc. (2014), pp. 5631-5634.
Laqua; et al., "FPGA controlled artificial vascular system", Current Directions in Biomedical Engineering (2015), 1:446-449.
Laqua; et al., "Improved FPGA controlled artificial vascular system for plethysmographic measurements", Current Directions in Biomedical Engineering (2016), 2(1): 689-693.
Larosa et al., Understanding the full Spectrum of Organ Injury Following Intrapartum Asphixia, Frontiers in Pediatrics, vol. 5, Article 16, pp. 1 to 11, 42783.
Larsen, Chrystal, Pulse Oximetry Devices Market, Meddevicetracker, Pharma Intelligence, pp. 1 to 58, 43070.
Laura Bennei, Alistair Jan Gunn, The Fetal Heart RateResponse to Hypoxia: Insights from Animal Models, Clin Perinatol 36 , pp. 655-672, 2009.
Lear et al., The peripheral chemoreflex: indefatigable guardian offetal physiological adaptation to labour, The Journal of Physiology, pp. 13, 2018.
Lemieux, P-A, et al., "Investigating non-Gaussian scattering processes by using nth-order intensity correlation functions," J. Opt. Xoc. Am. A, vol. 16, No. 7, Jul. 1999, pp. 1651-1664.
Locatelli et al., Aprotinin in cardiac surgery, etc, The Lancet, vol. 338, pp. 254-257, 33446.
Louie et al. , Four Types of Pulse Oximeters Accurately Detect Hypoxia during Low Perfusion and Motion, Anesthesiology, vol. XXX, No. X, pp. 1 to 11, 2017.
Louise Marie Roth and Megan M. Henley, Unequal Motherhood: Racial-Ethnic and Socioeconomic Disparities in Cesarean Sections in theUnited States, Social Problems, vol. 59, No. 2 University of California Press on behalf of the Society for the Study of Social Problems , pp. 207-227, 41030.

(56) References Cited

OTHER PUBLICATIONS

Luttkus et al., Pulse oximetry during labour—does it give rise to hope? Value of saturation monitoring in comparison to fetal blood gas status, European Journal of Obstetrics & Gynecology and Reproductive Biology 110, pp. S132-S138, 2003.
Mallinckrodt, Nellcor Perinatal Business, OxiFirst Fetal Oxygen Saturation Monitoring System, US Food & Drug Administration ?, pp. 31, 2000.
Mannheimer, et al., "Wavelength Selection for Low-Saturation Pulse Oximetry", IEEE Transactions on Biomedical Engineering, vol. 44, No. 3, (Mar. 1997), 44(3):148-158.
Maritta Ku Hnert and Stephan Schmidt, Intrapartum management of nonreassuring fetal heartrate patterns: A randomized controlled trial of fetalpulse oximetry, American Journal of Obstetrics and Gynecology, vol. 191, pp. 1989-1995, 38106.
Martinek et al., "Non-Invasive Fetal Monitoring: A Maternal Surface ECG Electrode Placement-Based Novel Approach for Optimization of Adaptive Filter Control Parameters Using the LMS and RLS Algorithms," MDPI Journal Sensors; Sensors 2017, 17, 1154, 32 pages.
Martinello, Management and investigation of neonatal-encephalopathy: 2017 update, Arch Dis Child Fetal Neonatal , pp. 13, 2017.
Mawn, et al., "Trans-Abdominal Monitoring of Fetal Arterial Oxygen Saturation Using Pulse Oximetry", Bioengineering Conference, 2002. Proceedings of the IEEE 28th Annual Northeast (Apr. 21, 2002), pp. 227-228.
McNamara, Didly, Continuous intrapartum pH, pO2, pCO2,and SpO2 monitoring, Obstet Gynecol Clin North Am, vol. 26, No. 4, pp. 671-693, 36495.
Medtech Insight, U.S. Patient Monitoring Devices Market, Medtech Insights, Medical Market and Technology Reports, pp. 1 to 235, 42309.
Mesquita et al., Direct measurement of tissue blood flow andmetabolism with diffuse optics, Philosophical Transactions of The Royal Society A, pp. 17, 2011.
Michael F. Greene, Obstetricians Still Await a Deus ex Machina, The new england journal of medicine, pp. 2, 2006.
Michael G. Ross, Labor and Fetal Heart Rate Decelerations: Relation to Fetal Metabolic Acidosis, Clinical Obstetrics and Gynecology, vol. 54, No. 1, pp. 74-82, 40603.
Miller, Colin, "Raydiant Oximetry: Provides Crucial Comfort for New Mothers," MedTech Strategist, vol. 5, No. 4—Mar. 27, 2018, 2 pages.
Molavi et al., "Motion Artifact Removal from Muscle NIR Spectroscopy Measurements," Canadian Conference on Electrical and Computer Engineering, 5 pages.
Mourant et al., "Mechanisms of light scattering from biological cells relevant to noninvasive optical-tissue diagnostics," Applied Optics, vol. 37, No. 16, Jun. 1, 1998, pp. 3586-3593.
Nelson et al., Electronicfetal monitoring, cerebralpalsy, and caesarean section: assumptions versus evidence, The BMJ, pp. 4, 42705.
Nioka et al., "Fetal transabdominal pulse oximeter studies using a hypoxic sheep model," The Journal of Maternal-Fetal and Neonatal Medicine, Jun. 2005; 17(6), pp. 393-399, 38504.
David S. Gardner and Dino A. Giussani, Enhanced Umbilical Blood Flow During Acute HypoxemiaAfter Chronic Umbilical Cord Compression, A Role for Nitric Oxide, Basic Science Reports in Circulation, pp. 331-335, 37824.
De Blasi et al., Noninvasive measurement of human forearm oxygen consumption by near infrared spectroscopy, Eur J Appl Physiol (1993) 67:20-25.
Delpy and Cope, Quantification in tissue near-inftared spectroscopy, Phil. Trans. R. Soc. Lond. B, pp. 11, 1997.
Delpy et al., "Estimation of optical pathlength through tissue from direct time of flight measurement," Phys. Med. Biol., 1988, vol. 33, No. 12, 1433-1442.
Dildy, et al., "Current status of the multicenter randomized clinical trial on fetal oxygen saturation monitoring in the United States," European Journal of Obstetrics & Gynecology and Reproductive Biology, Mar. 1997;72 Suppl:S43-50.
Dildy, et al., "Intrapartum fetal pulse oximetry: Fetal oxygen saturation trends during labor and relation to delivery outcome", Am J Obstet Gynecol (Sep. 1994), 171(3):679-684.
Dildy, et al., "Preliminary Experience with Intrapartum Fetal Pulse Oximetry in Humans," Obstetrics and Gynecology, Apr. 1, 1993, 81(4):630-635.
Dildy, et al., Intrapartum fetal pulse oximetry: Past, present, and future, American Journal of Obstetrics&Gynecology, pp. 9, 1996.
Dildy, et al., Management of prolonged decelerations, OBG Management, pp. 7, 2006.
Dildy, G.A., "Fetal Pulse Oximetry," Clinical Obstetrics and Gynecology, Mar. 2011;54(1):66-73. doi: 10.1097/GRF.0b013e31820a0f71.
Diniz, Adaptive Filtering Algorithms and Practical Implemetation, Springer www.springer.com, pp. 636, 2008.
Diogo Ayres-De-Campos, Electronic fetal monitoring orcardiotocography, 50 years later: what's in a name?, American Journal of Obstetrics & Gynecology, pp. 545-546, 43252.
Dong et al., "Simultaneously Extracting Multiple Parameters via Fitting One Single Autocorrelation Function Curve in Diffuse Correlation Spectroscopy," IEEE Transactions On Biomedical Engineering, vol. 60, No. 2, Feb. 2013, pp. 361-368.
Donlon, Elliott, et al., "MEG Visual Stimuli Software", MEG Setup Documentation, 3 pages.
Dr. Soheil Ghiasi, Dr. Andre Knoesen, Daniel Fong, Transabdominal Fetal Oximetry, Project conducted at the Laboratory for Embedded and Programmable Systems (LEPS), pp. 1 to 4.
Durduran and Yodh, "Diffuse correlation spectroscopy for non-invasive, micro-vascular cerebral bloodflow measurement," NeuroImage 85 (2014) 51-63.
Durduran et al., "Diffuse optics for tissue monitoring and tomography," Progress in Physics, pp. 44, 2010.
E Chandraharan, Fetal scalp blood sampling during labour: is it auseful diagnostic test or a historical test that nolonger has a place in modern clinical obstetrics?, Royal College of Obstetricians and Gynaecologists www.bjog.org, pp. 1056-1062, 41704.
East CE, Leader LR, Sheehan P, Henshall NE, Colditz PB, Lau R, Intrapartum fetal scalp lactate sampling for fetal assessmentin the presence of a non-reassuring fetal heart rate trace, Cochrane Database of Systematic Reviews 2015, Issue 5. pp. 1 to 39, 2015.
East et al., Intrapartum Oximetry of the Fetus, Anesthesia & Analgesia, vol. 105, No. 6, pp. S59-S65, 43070.
East et al., The effect of intrapartum fetal pulse oximetry, in thepresence of a nonreassuring fetal heart rate pattern, onoperative delivery rates: A multicenter, randomized,controlled trial (the FOREMOST trial), American Journal of Obstetrics and Gynecology (2006) 194, pp. 606.e1-606.e16, 2006.
East et al., A cost-effectiveness analysis of the intrapartumfetal pulse oximetry multicentre randomisedcontrolled trial (the FOREMOST trial), BJOG an International Journal of Obstetrics and Gynaecology, pp. 8, 2006.
East et al., Fetal oxygen saturation and uterine contractions during labor, ?, pp. 1, 1998.
East et al., Fetal oxygen saturation during maternal bearing down efforts in the second stage of labor, 1 page, 1998.
East et al., Fetal Oxygen Saturation Monitoring in Labour: An Analysis of 118 Cases, Journal of Obstetrics and Gynaecology, vol. 37, No. 4, pp. 397-401, 1997.
East et al., Fetal pulse oximetry for fetal assessment in labour (Review), Cochrane Collaboration, pp. 76, 2014.
East et al., Update on intrapartum fetal pulse oximetry, Aust N Z J Obstet Gynaecol, pp. 6, 2002.
Eden et al., "Reengineering Electronic Fetal Monitoring Interpretation: Using the Fetal Reserve Index to Anticipate the Need for Emergent Operative Delivery," Reproductive Sciences 2018, vol. 25(4), pp. 487-497, 2018.
Eden, et al.. The "Fetal Reserve Index":Re-Engineering the Interpretation and Responses to Fetal Heart Rate Patterns, Fetal Diagnosis and Therapy, 43, pp. 90-104, 42894.

(56) References Cited

OTHER PUBLICATIONS

Evans et al., Re-engineering the interpretation of electronicfetal monitoring to identify reversible risk forcerebral palsy: a case control series, The Journal of Maternal-Fetal & Neonatal Medicine, pp. 10, 2018.
Fabbri et al., "Optical measurements of absorption changes in two-layered diffusive media," Phys. Med. Biol. (2004) 1183-1201.
Fantini et al., "Frequency-domain multichannel optical detector for nonivasive tissue spectroscopy and oximetry," Optical Engineering, 11 pages, 34700.
Farrell, Thomas J., et al., "Influence of layered tissue architecture on estimates of tissue optical properties obtained from spatially resolved diffuse reflectometry," Applied Optics, pp. 15, 35886.
Fatemi, et al., Hypoxic Ischemic Encephalopathy in the Term Infant, Author manuscript; available in PMC Dec. 2010, pp. 23, 40148.
Figures of Two-minute tracing showing fetal heart rate, and Pulse oximetry tracing from 25-week gestation fetus undergoing open congenital diaphragmatic hernia repair, figures and its descriptions in Anesthesia for Fetal Procedures and Surgery, p. 280-281.
Firbank et al., "An investigation of light transport through scattering bodies with non-scattering regions," Phys. Med. Biol. 41 (1996) 767-783.
Fong et al., Transabdominal Fetal Pulse Oximetry:The Case of Fetal Signal Optimization, 2017 IEEE 19th International Conference on e-Health Networking, Applications and Services (Healthcom), pp. 1 to 6, 2017.
Fong et al., Recovering the Fetal Signal in Transabdominal Fetal Pulse Oximetry, Article appearing in unedited Manuscript Smart Health, https://doi.org/10.1016/j.smhl.2018.07.011, pp. 13, 43282.
Fong, Daniel D., et al., "Recovering the Fetal Signal in Transabdominal Fetal Pulse Oximetry", Smart Health, 9-10 (2018) pp. 23-36.
Franceschini et al., "Assessment of Infant Brain Development With Frequency-Domain Near-Infrared Spectroscopy," Pediatric Research vol. 61, No. 5, 2007, pp. 546-551, 2007.
Franceschini, Maria Angela, et al., "Influence of a superficial layer in the quantitative spectroscopic study of strongly scattering media," Applied Optics, Nov. 1, 1998, vol. 37, No. 31, pp. 7447-7458.
Gagnon et al., "Short separation channel location impacts the performance of short channelregression in NIRS," NeuroImage 59 (2012) 2518-2528.
Gagnon et al., Further improvement in reducing superficial contamination in NIRS using double short separation measurements, NeuroImage 85 (2014) 127-135.
Ganesan et al., "Diffuse optical spectroscopic imaging of subcutaneous adipose tissue metabolic changes during weight loss," Int J Obes (Lond). Aug. 2016; 40(8). Author Manuscript available in PMC Oct. 22, 2016., pp. 1292-1300, 42665.
Gardosi et al, Adaptation of pulse oximetry for fetal monitoringduring labour, The Lancet, vol. 337, pp. 1265-1267, 33383.
Gardosi et al., Continuous Intrapartum Monitoring Offectal Oxygen Saturation, The Lancet, pp. 2, 1989.
Garite et al., Transactions of the Twentieth Annual Meeting of the Society Formaternal-Fetal Medicine—Continued, American Journal of Obstetrics and Gynecology vol. 183 No. 5, pp. 1049-1058, 36831.
Giordano, Geoff, "New ANSI guidelines remind users to take stock of industrial laser protections," LaserFocusWorld, Oct. 7, 2014, 5 pages.
Goodlin, Robert C., "Preliminary Experience with Intrapartum Fetal Pulse Oximetry in Humans," Letter, Obstetrics and Gynecology, vol. 82, No. 2, Aug. 1993, pp. 314-315.
Graham et al., A systematic review of the role of intrapartum hypoxia-ischemia in the causation of neonatal encephalopathy, American Journal of Obstetrics&Gynecology, pp. 9, 39783.
"Assessing the Photobiological Safety of LEDs," 8 pages, 2012.
"Corometrics™ 250 Series Monitor Operator's Manual", GE Healthcare, Revision E (Apr. 28, 2009), 258 pgs.
"Fetal Pulse Oximetry System Clinical Use Guide", OxiFirst, Nellecor (2003), 60 pgs.

"Narrow beam LED in Dragon Dome package (850nm)", OSRAM Opto Semicondutors (Mar. 10, 2014), Version 1.3, SFH 4783, pp. 1-12.
"OSRAM Opto Semiconductors GF CSHPM1.24-3S4S-1", Mouser Electronics (accessed Dec. 2016), 2 pgs.
Aapo Hyvärinen, Fast and Robust Fixed-Point Algorithms for Independent Component Analysis, IEEE Trans. on Neural Networks, pp. 16, 1999.
Aaronson; et al., "Android-Based Tocodynamometer and Fetal Heart Rate Monitor", tocotronics (2013), 21 pgs.
Adam J. Wolfberg, The Future of Fetal Monitoring, Reviews in Obstetrics & Gynecology, vol. 5 No. 3/4, pp. e1322-e136, 2012.
Aldrich, C. J., et al., Late fetal heart decelerations and changes in cerebral oxygenation during the first stage of labour, British Journal of Obstetrics and Gynaecology Jan. 1995, vol. 102, pp. 9 to 13, 34700.
Alex C., Vidaeff MD, MPH and Susan Ramin, MD, Fetal pulse oximetry: 8 vital questions, OBG Management, pp. 28-44, 38047.
Alfirevic Z, Devane D, GYTE GML, Cuthbert A, Continuous cardiotocography (CTG) as a form of electronicfetal monitoring (EFM) for fetal assessment during labour(Review), Cochrane Database of Systematic Reviews 2017, Issue 2. pp. 1 to 56, 2017.
Alistair Jan Gunn and Laura Bennet, Fetal Hypoxia Insultsand Patterns of Brain Injury: Insights from Animal Models, Clin Perinatol 36, pp. 579-593, 2009.
Amer and Oorschot, Xenon Combined With Hypothermia in Perinatal Hypoxic-Ischemic Encephalopathy: A Noble Gas, a Noble Mission, Pediatric Neurology, pp. 6, 2018.
Angelo, Joseph P., et al., "Review of structured light in diffuse optical imaging," Journal of Biomedical Optics 24(7), 071602 (Jul. 2019), 20 pages.
B. Leszczynska-Gorzelak et al., "Intrapartum cardiotocography and fetal pulse oximetryin assessing fetal hypoxia," International Journal of Gynecology & Obstetrics 76 (2002), pp. 9 to 14, 37167.
Bansal, A.K., et al., "An Optoelectronic Muscle Contraction Sensor", EPSRC (accessed Dec. 2016), University of St Andrews, 1 pg.
Bansal; et al., "Wearable Organic Optoelectronic Sensors for Medicine", Advanced Materials (2014), 7 pgs.
Barry and Anthony, The Pregnant Sheep as a Model for Human Pregnancy, NIH Public Access Theriogenology, Author manuscript, pp. 20, 43101.
Belfort et al., A Randomized Trial of Intrapartum Fetal ECG ST-Segment Analysis, The new england journal of medicine, pp. 10, 42217.
Bennet, Laura, et al., "The Cerebral Hemodynamic Response to Asphyxia and Hypoxia in the Near-term Fetal Sheep as Measured by Near Infrared Spectroscopy," Pediatric Research 44, pp. 1 to 23, 36130.
Bevilacqua et al., "In vivo local determination of tissue optical properties: applications to human brain," Applied Optics, Aug. 1, 1999, vol. 38, No. 22, pp. 4939-4950.
Bloom et al., Fetal Pulse Oximetry: Duration of Desaturation and Intrapartum Outcome, Journal of Obstetrics and Gynecology, vol. 9, No. 6, pp. 1036-1040, 36312.
Bloom et al., What We Have Learned About Intrapartum Fetal Monitoring Trials in the MFMU Network, HHS Public Access Author manuscript in Semin Perinatol, vol. 40, No. 5, pp. 307-317, 42583.
Bloom et al., Fetal Pulse Oximetry and Cesarean Delivery, The new england journal of medicine, pp. 8, 39022.
Boas and Yodh, "Spatially varying dynamical properties of turbid media probed with diffusing temporal light correlation," J. Opt. Soc. Am. A, vol. 14, No. 1, Jan. 1997, pp. 192-215.
Boas et al., "Diffuse optical imaging of brain activation: approaches to optimizing image sensitivity, resolution, and accuracy," NeuroImage 23 (2004) S275-S288.
Boas et al., "Scattering and Imaging with Diffusing Temporal Fields correlation," Physical Review Letters, vol. 75, No. 9, Aug. 28, 1995, pp. 1855-1859.
Bottrich et al., "Signal Separation for Transabdominal Non-invasive Fetal Pulse Oximetry using Comb Filters," Institute of Electrical and Electronics Engineers (IEEE), pp. 5870-5873, 2018.

(56) References Cited

OTHER PUBLICATIONS

Bottrich; et al., "Principle study on the signal connection at transabdominal fetal pulse oximetry", Current Directions in Biomedical Engineering (2016), 2(1): 659-663.

Bottrich; et al., "Simulation based investigation of source-detector configurations for non-invasive fetal pulse oximetry", Current Directions in Biomedical Engineering (2015), 1:450-453.

Bozkurt, Alper et al., "Safety assessment of near infrared light emitting diodes for diffuse optical measurements," BioMedical Engineering OnLine 2004, 3, 10 pages, http://www.biomedical-engineering-online.com/content/3/1/9, Mar. 11, 2004.

Buckley et al., Diffuse correlation spectroscopy for measurement of cerebral blood flow: future prospects, Neurophotonics 1(1), 011009 (Jul.-Sep. 2014), 8 pages.

Buschmann et al., Fetal oxygen saturation measurement bytransmission pulse oximetry, The Lancet, pp. 1, 33664, Mar. 1992.

Cahill, Alison, et al., "A prospective cohort study of fetal heart rate monitoring:deceleration area is predictive of fetal acidemia," American Journal of Obstetrics&Gynecology, vol. 218, Issue 5, May 2018, 12 page(s).

Caliskan et al., Reduction in caesarean delivery with fetal heartrate monitoring and intermittent pulse oximetryafter induction of labour with misoprostol, The Journal of Maternal-Fetal & Neonatal Medicine http://dx.doi.org/10.1080/14767050802613207, pp. 8, 43009.

Carbonne et al., Multicenter oximetry study on the clinical value of fetal pulse , Am J Obstet Gynecol, pp. 593-598, 35674.

Carbonne et al., Fetal pulse oximetry: correlation between changes in oxygen saturation and neonatal outcome. Preliminary reporton 39 cases, European Journal of Obstetrics & Gynecology and Reproductive Biology , pp. 5, 1994.

Carin Dassel et al., Reflectance Pulse Oximetry in Fetal Lambs, Pediatric Research, pp. 4, 1992.

Caroline E Ahearne, Geraldine B Boylan, Deirdre M Murray, Short and long term prognosis in perinatal asphyxia: An update, World Journal of Clinical Pediatrics, vol. 5, Issue 1, pp. 67-74, 42408.

Carter et al., Calibration of a Reflectance Pulse Oximeter in Fetal Lambs for Arterial Oxygen Saturations Below 70%, J Soc Gynecol Invest, pp. 5, 1998.

Cerebral Palsy Guidance, Cerebral Palsy, Cerebral Palsy Guidance Website, pp. 1 to 14, 2018.

Chan et al., "Effects of Compression on Soft Tissue Optical Properties," IEEE Journal of Selected Topics in Quantum Electronics, vol. 2, No. 4, Dec. 1996, pp. 943-950.

Cheung et al., In vivo cerebrovascular measurement combining diffuse near-infrared absorption and correlation spectroscopies, Phys. Med. Biol. 46 (2001) 2053-2065.

Choe, Regine, "Diffuse Optical Tomography and Spectroscopy of Breast Cancer and Fetal Brain," Pub'd, Sep. 29, 2005, Faculties of the University of Pennsylvania.

Choe; et al., "Transabdominal near infrared oximetry of hypoxic stress in fetal sheep brain in utero", PNAS (Oct. 28, 2003), 100(22):12950-12954; https://doi.org/10.1073/pnas.1735462100.

Clark et al., Intrapartum management of category II fetal heart ratetracings: towards standardization of care, American Journal of Obstetrics & Gynecology, pp. 89-97, 41487.

Clark et al., The limits of electronic fetal heart rate monitoring in theprevention of neonatal metabolic acidemia, American Journal of Obstetrics & Gynecology, pp. 163 e.1-163 e.6, 42767.

ClearView Healthcare Partners LLC, 2018, 6 pages.

Colditz et al., Fetal pulse oximetry : Instrumentation and Recent Clinical Experience, Clinics in Perinatology, pp. 12, 1999.

Daniel Fong and Ghiasi Soheil, Transabdominal Fetal Blood Oximetry, Website of the University of California, Davis, Office of Research http://research.ucdavis.edu/u/s/ia, pp. 1, 2017.

Nitzan, et al., "Calibration-Free Pulse Oximetry Based on Two Wavelengths in the Infrared—A Preliminary Study," Sensors 2014, 14, 7420-7434; doi:10.3390/s140407420. pub'd Apr. 23, 2014.

Nonnenmacher et al., Predictive value of pulse oximetry for the developmentof fetal acidosis, J. Perinat. Med, pp. 4, 2010 ?.

Norén, Häkan, et al., "Reduced prevalence of metabolic acidosis at birth:an analysis of established STAN usage in the total population of deliveries in a Swedish district hospital," Am J Obstet Gynecol 2010; 202:546.e1-7.

Novak et al , Perinatal Brain Injury Mechanisms, Prevention, and Outcomes, http://perinatology.theclinics.com/, pp. 357-375, 2018.

OBG Project, Which Fetal Heart Monitoring Parameters Best Predict Fetal Acidemia?, https://www.obgproject.com/category/granrounds/.

Office Action dated Feb. 1, 2018, from the Taiwan Intellectual Property Office, for Taiwan Patent Application No. 105143848, 17 pages.

Olutoye et al., Food and Drug Administration warning on anesthesia and brain development: implications for obstetric and fetal surgery, American Journal of Obstetrics & Gynecology, pp. 98-102, 43101.

Paul Eunson, The long-term health, social, and financial burden ofhypoxic-ischaemic encephalopathy, Developmental Medicine & Child Neurology, pp. 48-50, 2015.

PCT International search report, International Searching Authority, for International Patent Application No. PCT/US2017/062782 filed on Nov. 21, 2017, pp. 1 to 4, 42005.

PCT/US2018/068042 International Search Report and Written Opinion, dated Apr. 26, 2019, 16 pages.

PCT/US2018/068049 International Search Report and Written Opinion, dated Apr. 26, 2019, 20 pages.

Peat et al., Continuous intrapartum measurement of fetal oxygen saturation , The Lancet, pp. 213, 32347, Aug. 27, 1988.

Peek et al., Fetal Pulse Oximetry and Cesarean Delivery, The New England Journal of Medicine , pp. 2, 39170.

Pereiraa and Chandraharan, Recognition of chronic hypoxia and pre-existing foetal injury on the cardiotocograph(CTG): Urgent need to think beyond the guidelines, Porto Biomedical Journal http://www.portobiomedicaljournal.com/, pp. 6, 2017.

Phelan and Joo Oh Kim , Fetal Heart Rate Observations in the Brain-Damaged Infant, Seminars in Perinatology, p. 9 (221-229), 2000.

Philips proprietary camera based monitoring technology is first in the world to measure absolute arterial blood oxygenation (SpO2) levels without ever touching the patient, Jun. 6, 2016, 4 pages (https://www.USA.philips.com/a-w/about/news/archive/standard/news/press/2016/20160606-philips-proprietary-camera-based-monitoring-technology-is-first-in-the-world-to-measure-absolute-arterial-blood-oxygenation-levels-without-ever-touching-the-patient.html).

Pifferi et al., "Real-time method for fitting time-resolved relectance and transmittance measurements with a Monte Carlo model," Applied Optics, vol. 37, No. 13, May 1998, pp. 3.

Porreco et al., Dystocia in nulliparous patients monitored with fetalpulse oximetry, American Journal of Obstetrics and Gynecology, 190, pp. 113-117, 2004.

Ragozzino et al., Average Fetal Depth in Utero: Data for Estimation of Fetal Absorbed Radiation Dose, Medical Physics, pp. 3, 1986.

Ramanujam, et al., "Photon migration through fetal head in utero using continuous wave, near infrared spectroscopy: clinical and experimental model studies", Journal of Biomedical Optics (Apr. 2000), 5(2):173-184, https://doi.org/10.1117/1.429984.

Ramanujam; et al., "Antepartum, Transabdominal Near Infrared Spectroscopy: Feasibility of Measuring Photon Migration Through the Fetal Head in Utero", The Journal of Maternal-Fetal Medicine (1999), 8:275-288.

Rei, M., et al., "Neurological damage arising from intrapartum hypoxia/acidosis," Best Practice & Research Clinical Obstetrics and Gynaecology 30 (2016) 79-86.

Ren, "Quasi-simultaneous multimodal imaging of cutaneous tissue oxygenation and perfusion," Journal of Biomedical Optics 20(12), 121307 (Dec. 2015), 11 pages.

Reuss and Siker, The pulse in reflectance pulse oximetry : modeling and experimental studies, Journal of Clinical Monitoring and Computing, pp. 11 (pp. 289-299), 2004.

Reuss, James L., "Factors Influencing Fetal Pulse Oximetry Performance," Journal of Clinical Monitoring and Computing, vol. 18, No. 1, 2004, pp. 13-24.

(56) References Cited

OTHER PUBLICATIONS

Reuss, James L., "Multilayer Modeling of Reflectance Pulse Oximetry," IEEE Transactions on Biomedical Engineering, vol. 52, No. 2, Feb. 2005, pp. 153-159.

Rivolta et al., Acceleration and Deceleration Capacity of Fetal Heart Rate in an In-Vivo Sheep Model, PLOS One, pp. 10, 41852.

Roche-Labarbe et al., "Noninvasive Optical Measures of CBV, StO2, CBF Index, and rCMRO2 in Human Premature Neonates' Brains in the First Six Weeks of Life," Human Brain Mapping 31:341-352 (2010).

Rod Kelly et al., Dose-dependent relationship between acidosis at birth and likelihood of death or cerebral palsy, Arch Dis Child Fetal Neonatal Ed 2017, pp. F1-F6, 43077.

Roemer and Walden, Sensitivity, specificity, receiver-operating characteristic (ROC)curves and likelihood ratios for electronic foetal heart rate monitoring using new evaluation techniques, Z Geburtshilfe Neonatol, vol. 214 No. 3, pp. 108-118, 40330.

S R Arridge et al., "The theoretical basis for the determination of optical path lengths in tissue: temporal and frequency analysis," Phys. Med. Biol., 1992, vol. 37, No. 7, 1531-1560.

S R Arridge, "Optical tomography in medical imaging," Inverse Problems 15 (1999) R41-R93.

S. R. Arridge, Inverse Problems in Optical Tomography, INI Cambridge, pp. 74, 2011.

Saager, Rolf B. et al., Direct characterization and removal of interfering absorption trends in two-layer turbid media, J. Opt. Soc. Am. A/vol. 22, No. 9/Sep. 2005, pp. 1874-1882.

Sabiani et al., Intra- and interobserver agreement amongobstetric experts in court regarding the reviewof abnormal fetal heart rate tracings andobstetrical management, American Journal of Obstetrics &Gynecology, pp. 8, 42339.

Saccone et al., Electrocardiogram ST Analysis During Labor A Systematic Review and Meta-analysis of Randomized Controlled Trials, Obstetrics & Gynecology, vol. 127, No. 1, pp. 127-135, 42370.

Salamalekis et al., Fetal pulse oximetry and wavelet analysis of the fetal heart rate in the evaluation of abnormal cardiotocography tracings, J. Obstet. Gynaecol Res vol. 32, No. 2, pp. 135-139, 38808.

Salamalekis et al., Computerised intrapartum diagnosis of fetal hypoxia based onfetal heart rate monitoring and fetal pulse oximetry recordingsutilising wavelet analysis and neural networks, BJOG: an International Journal of Dbstetrics and Gynaecology, Oct. 2002, vol. 109, pp. 1137-1142, 37530.

Sartwelle et al., The Ethics of Teaching Physicians Electronic Fetal Monitoring: And Now for the Rest of the Story, The Surgery Journal, pp. 6, 2017.

Sassaroli, Angelo et al., "Comment on the modified Beer-Lambert law for scattering media," Physics in Medicine & Biology, vol. 49, No. 14, pub'd Jul. 5, 2004 (Phys. Med. Biol. 49 (2004) N255-N257).

Schiermeier et al., Sensitivity and specificity of intrapartum computerised FIGO criteria for cardiotocographyand fetal scalp pH during labour: multicentre, observational study, BJOG An International Journal of Obstetrics and Gynaecology, pp. 7, 2008.

Schweiger, Martin et al., Near-infrared imaging: photon measurement density functions, SPIE, vol. 2389, 13 page(s), 1995.

Seelbach-Göbel et al., The prediction of fetal acidosis by means of intrapartum fetalpulse oximetry, American Journal of Obstetrics and Gynecol, pp. 9, 36161, Jan. 1999.

Shang et al., "Portable optical tissue flow oximeter based on diffuse correlation spectroscopy," Optics Letters, vol. 34, No. 22, Nov. 15, 2009, pp. 3556-3558.

Siristatidis et al., Alterations in Doppler velocimetry indices of the umbilical artery duringfetal hypoxia in labor, in relation to cardiotocography and fetal pulseoximetry findings, Arch Gynecol Obstet, pp. 6, 2005.

Siristatidis et al., Evaluation of fetal intrapartum hypoxia by middle cerebraland umbilical artery Doppler velocimetrywith simultaneous cardiotocography and pulse oximetry, Arch Gynecol Obstet, pp. 6, 2004.

Siristatidis et al., Intrapartum Surveillance of IUGR Fetuses with Cardiotocography and Fetal Pulse Oximetry, Biology of the Neonate, 83, pp. 162-165, 2003.

Spencer, et al., MASS Spectrometer System for Continuous Skin-Surface and Intravascular Blood Gas Measurement of Maternal-Fetal Respiration in Labour, Journal of Biomedical Engineering, pp. 8, 1986.

Spong, et al., Preventing the First Cesarean Delivery: Summary of a Joint Eunice Kennedy Shriver National Institute of Child Health and Human Development, Society for Maternal-Fetal Medicine, and American College of Obstetricians and Gynecologists Workshop, American Journal of Obstetrics and Gynecology, pp. 22, 2012.

Steinbrink et al., "Illuminating the BOLD signal: combined fMRI-fNIRS studies", Magnetic Resonance Imaging 24, pp. 495-505, 2006.

Extended European Search Report for European Patent Application No. 16882598.2 dated Jul. 25, 2019.

Zourabian et al."Non-Invasive Trans-abdominal Monitoring of Fetal Cerebral Oxygenation Using Pulse Oximetry," Visutal Communications and Image Processing; San Jose, SPIE vol. 3597, Jan. 1, 1999, pp. 669-675.

"Anesthesia for Fetal Procedures and Surgery," pp. 280-281.

Bauer, et al., "Quantitative photoacoustic imaging:correcting for heterogeneous light fluence distributions using diffuse optical tomography," Journal of Biomedical Optics, 16(9): 096016-1-096016-7, Sep. 2011.

East, et al., "Intrapartum Oximetry of the Fetus," Anesthesia & Analgesia, 105(6), pp. S59-S65, Dec. 2007.

Emberson, et al., "Isolating the effects of surface vasculature in infant neuroimaging using short-distance optical channels: a combination of local and globaleffects," Neurophotonics, 3(3), p. 031406-1-031406-12, Jul.-Sep. 2016.

Fantini, et al., "Frequency-domain techniques for tissue spectroscopy and imaging", In Handbook of Optical Biomedical Diagnostics, Second Edition, vol. 1: Light Tissue Interaction, Chapter 7, pp. 1-52, 2002.

Farzam, "Hybrid diffuse optics for monitoring of tissue hemodynamics with applications in oncology," Doctoral Thesis in Photonics, Institute of Photonic Sciences, p. 240, Jul. 2014.

International Search Report and the Written Opinion of the International Searching Authority for International Application No. PCT/US19/40639 dated Nov. 12, 2019.

International Search Report and the Written Opinion of the International Searching Authority for International Application No. PCT/US2017/062782, dated Feb. 19, 2018.

Jacques, "Corrigendum: Optical properties of biological tissues: a review," IOP Publishing, Phys. Med. Biol. 58: 5007-5008, Jun. 27, 2013.

Jezewski, et al., "Extraction of Fetal Heart-Rate Signal as the Time Event Series From Evenly Sampled Data Acquired Using Doppler Ultrasound Technique," IEEE Transactions on Biomedical Engineering, 55(2): 805-810, Feb. 2008.

Jumadi, et al., Development of theoretical oxygen saturation calibration curve based on optical density ratio and optical simulation approach,: AIP Conference Proceedings 1883, pp. 1-11, Sep. 14, 2017.

Jumadi, et al., "Investigating the Effect of Total Radiated Power on Fetus Using Optical Simulation Approach Based on Exposure Safety Limit for Eye and Tissue Injury," Journal of Life Sciences and Technologies, 2(1): 24-27, Jun. 2014.

Kirschbaum, et al., "Oxyhemoglobin dissociation characteristics of human and sheep maternal and fetal blood," Am. J. Obstetric and Gynecology, 96(5): 741-759, 1966.

Konugolu Venkata Sekar, "Broadband Time-Domain Disffuse Optics for Clinical Diagnostics and Diffuse Raman Spectroscopy," Doctoral Dissertation, Politecnico de Milano, Physics Department, pp. 1-288, 2016.

(56) References Cited

OTHER PUBLICATIONS

Meschia, et al., "A Comparison of the Oxygen Dissociation Curves of the Bloods of Maternal, Fetal and Newborn Sheep at Various pHs," In: Oxgen Dissociation Curves in Sheep at Various pHs, pp. 95-97, Sep. 23, 1960.

Nasiriavanaki, et al., "High-resolution photoacoustic tomography of resting-state functional connectivity in the mouse brain," PNAS, 111(1): 21-26, Jan. 7, 2014.

Patient Safety Movement Foundation, "Actionable Patient Safety Solution (APSS) #110: Reducing Unnecessary C-Sections," 2018 Patient Safety Movement Foundation, pp. 1-8, Aug. 15, 2018.

Peebles, et al., "Effect of oxytocin on fetal brain oxgenation during labour," The Lancet, 338: 254-255, Jul. 27, 1991.

Peters, et al., "Beat-to-beat detection of fetal heart rate: Doppler ultrasound cardiotocography compared to direct ECG cardiotocography in time and frequency domain," Physiological Measurement, 25: 585-593, 2004.

Townsend, et al., "Pulse Oximetry," Medical Electronics, Michaelmas Term, 2001.

Truven Health Analytics, The Cost of Having a Baby in the United States—Executive Summary, Truven Health Analytics Marketscan Study, p. 5, Jan. 2013.

Van 'T Hooft, In "Improving evaluation of obstetric interventions," University of Amsterdam Dissertation, pp. 1-243, 2016.

Willmann, et al., "Small-volume frequency-domain oximetry: phantom experiments and first in vivo results," Journal of Biomedical Optics, 8(4): 618-628, Oct. 2003.

Yamashiro, E., et al., "Fetal tolerance of maternal resuscitative endovascular balloon occlusion of the aorta in a sheep model," Am. J. Obstetrics & Genecology, Supplemental to Jan. 2020, pp, S718-S719, Jan. 2020.

401

402

601

602

603

Result of Multiplying Reflected Electronic Signal Intensity for $\lambda_1$ and Doppler Signal Synchronized Over Time

604

Result of Multiplying Reflected Electronic Signal Intensity for $\lambda_1$ and Doppler Signal Synchronized Over Time (Averaged Over Several Periods)

605

606 Result of Multiplying Reflected Electronic Signal Intensity for $\lambda_2$ and Doppler Signal Synchronized Over Time

607

Result of Multiplying Reflected Electronic Signal Intensity for $\lambda_2$ and Doppler Signal Synchronized Over Time (Averaged Over Several Periods)

| Wavelength [nm] | Hb HbF | Hb HbA | HbO2 HbF | HbO2 HbA | Difference HbF (Hb-HbO2) | Difference HbA (Hb-HbO2) | Ratio HbF (Hb-HbO2)/HbO2 |
|---|---|---|---|---|---|---|---|
| 450 | 12.94 | 13.51 | 15.82 | 16.2 | -2.88 | -2.69 | -0.18204804 |
| 480 | 3.18 | 3.35 | 6.61 | 6.72 | -3.43 | -3.37 | -0.51891074 |
| 500 | 4.25 | 4.34 | 5.08 | 5.15 | -0.83 | -0.81 | -0.16332582 |
| 520 | 6.5 | 6.49 | 6.03 | 5.98 | 0.47 | 0.5 | 0.07784361 |
| 540 | 10.57 | 10.5 | 14.48 | 14.32 | -3.91 | -3.82 | -0.27002762 |
| 542 | 11.19 | 11.09 | 14.62 | 14.52 | -3.43 | -3.43 | -0.23461013 |
| 550 | 13.15 | 12.97 | 11.84 | 12.01 | 1.31 | 0.96 | 0.11064189 |
| 554 | 13.55 | 13.35 | 9.95 | 10.17 | 3.6 | 3.18 | 0.36180904 |
| 560 | 13.3 | 13.09 | 8.6 | 8.77 | 4.7 | 4.32 | 0.54651162 |
| 568 | 11.97 | 11.85 | 10.49 | 10.5 | 1.48 | 1.35 | 0.14108674 |
| 576 | 10.06 | 10.07 | 15.38 | 15.37 | -5.32 | -5.3 | -0.34590377 |
| 578 | 9.6 | 9.62 | 15.45 | 15.36 | -5.85 | -5.74 | -0.37884077 |
| 590 | 6.34 | 6.87 | 4 | 4.26 | 2.34 | 2.61 | 0.735 |
| 600 | 3.74 | 3.74 | 0.9 | 0.96 | 2.84 | 2.78 | 3.15555555 |
| 630 | 1.05 | 1.06 | 0.1 | 0.11 | 0.95 | 0.95 | 9.5 |
| 660 | 0.83 | 0.81 | 0.07 | 0.08 | 0.76 | 0.73 | 10.85714286 |
| 680 | 0.62 | 0.61 | 0.08 | 0.09 | 0.54 | 0.52 | 6.75 |
| 700 | 0.46 | 0.44 | 0.09 | 0.09 | 0.37 | 0.35 | 4.625 |
| 750 | 0.4 | 0.39 | 0.13 | 0.14 | 0.27 | 0.25 | 2.07692307 |
| 775 | 0.29 | 0.29 | 0.16 | 0.17 | 0.13 | 0.12 | 0.8125 |
| 800 | 0.21 | 0.2 | 0.19 | 0.2 | 0.02 | 0 | 0.10526315 |
| 805 | 0.2 | 0.2 | 0.19 | 0.21 | 0.01 | -0.01 | 0.05263157 |
| 840 | 0.18 | 0.19 | 0.23 | 0.25 | -0.05 | -0.06 | -0.21739130 |
| 845 | 0.18 | 0.19 | 0.24 | 0.25 | -0.06 | -0.06 | -0.25 |
| 880 | 0.19 | 0.2 | 0.27 | 0.28 | -0.08 | -0.08 | -0.29629629 |
| 904 | 0.21 | 0.21 | 0.28 | 0.3 | -0.08 | -0.09 | -0.28571428 |
| 920 | 0.2 | 0.21 | 0.29 | 0.3 | -0.09 | -0.09 | -0.31034482 |
| 940 | 0.17 | 0.18 | 0.28 | 0.29 | -0.11 | -0.11 | -0.39285714 |
| 960 | 0.12 | 0.14 | 0.27 | 0.28 | -0.15 | -0.14 | -0.55555555 |
| 1000 | 0.04 | 0.06 | 0.25 | 0.25 | -0.21 | -0.19 | -0.84 |

* Notation:
Hb = haemoglobin in deoxy-state
HbO2 = haemoglobin in oxy-state
HbF = fetal haemoglobin
HbA = adult haemoglobin

** Reference: Zijlstra et al., Clin. Chem 37/9, 1633-1638 (1991)

700

SYSTEMS, DEVICES, AND METHODS FOR PERFORMING TRANS-ABDOMINAL FETAL OXIMETRY AND/OR TRANS-ABDOMINAL FETAL PULSE OXIMETRY USING A HEARTBEAT SIGNAL FOR A PREGNANT MAMMAL

RELATED APPLICATIONS

This application is a CONTINUATION-IN-PART of U.S. patent application Ser. No. 15/973,141 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING A FETAL HEARTBEAT SIGNAL FOR A PREGNANT MAMMAL" filed on May 7, 2018, which is a CONTINUATION of U.S. patent application Ser. No. 15/698,954 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING A FETAL HEARTBEAT SIGNAL" filed on Sep. 8, 2017, which is a CONTINUATION of U.S. patent application Ser. No. 15/393,752 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY" filed on Dec. 29, 2016, now U.S. Pat. No. 9,757,058, which is a NON-PROVISIONAL of, and claims priority to, U.S. Provisional Patent Application No. 62/273,196 entitled "SYSTEMS, DEVICES, AND METHODS FOR DETECTING/DETERMINING FETAL HEMOGLOBIN OXYGEN SATURATION LEVELS" filed Dec. 30, 2015, all of which are incorporated by reference, in their entireties, herein.

FIELD OF INVENTION

The present invention is in the field of medical devices and, more particularly, in the field of trans-abdominal fetal oximetry and trans-abdominal fetal pulse oximetry.

BACKGROUND

When a pregnant mammal is engaged in the labor and delivery process for her fetus, a common practice is to monitor both the heart rate of the fetus and the uterine tone of the pregnant mammal. The uterine tone of the pregnant mammal provides information regarding the uterine contractions of the pregnant mammal by measuring the pressure exerted by the uterine muscle in units of pressure, for example, millimeters of mercury (mmHg) and/or kilo Pascals (kPg). One way to provide information regarding the fetal heartbeat and uterine tone to a doctor or other healthcare provider is to provide a graph, either in paper or electronic form, that displays a fetal heart rate over time and uterine tone over time. In most cases, this information is synchronized so that the fetal heartbeat and uterine tone for a particular moment in time may be simultaneously observed. By comparing the fetal heart rate at a particular moment in time with the uterine tone at that same moment in time, a doctor may be able to determine whether the fetal heart rate decreases when the pregnant mammal experiences a contraction.

FIGS. 1A and 1B provide two examples of simultaneously displayed fetal heartbeat and uterine tone for corresponding moments in time. In FIGS. 1A and 1B, graphs 10A and 10B, respectively, display fetal heartbeat in beats per minute as a function of time where each vertical line provided on the grid represents one minute. In FIGS. 1A and 1B, graphs 12A and 12B, respectively, display uterine tone in mmHg and kPa as a function of time. In FIG. 1A, graph 10A shows fetal heart rate within a normal range of 120-180 beats per minute and there are no obvious fluctuations in the fetal heart rate that correspond with changes in uterine tone. With the information provided by FIG. 1A, a doctor may draw the conclusion that the fetus is not being negatively impacted by the uterine contractions and is not in distress. In contrast, graph 10B shows a fetal heart rate that experiences significant dips (e.g., from approximately 150 beats per minute prior to a uterine contraction to below 90 beats per minute during an immediately following a uterine contraction) that correspond with uterine contractions (i.e., increases in pressure within the uterus). With the information provided by FIG. 1B, a doctor may draw the conclusion that the fetus is being negatively impacted by the uterine contractions and may be in distress (e.g., experiencing a lack of oxygen that may cause neurologic damage). Upon drawing this conclusion, the doctor may decide that the fetus' health is in danger and, therefore, it should be surgically removed from the uterus via a Caesarian section (C-section). However, a change in fetal heart rate of the type shown in FIG. 1B does not always indicate that the fetus is in distress as there are many other possible causes for a drop in fetal heart rate. Thus, the doctor may prescribe a C-section when one is not needed causing undue harm to the pregnant mammal.

Oximetry is a method for determining the oxygen saturation of hemoglobin in a mammal's blood. Typically, 90% (or higher) of an adult human's hemoglobin is saturated with (i.e., bonded to) oxygen while only 30-60% of a fetus's blood is saturated with oxygen.

Pulse oximetry is a type of oximetry that uses changes in arterial blood volume through a heartbeat cycle to internally calibrate oxygen saturation measurements of the oxygen level of the blood.

Current methods of performing fetal oximetry are flawed for many reasons. For example, while U.S. Patent Publication No. 2004/0116789 describes a fetal oximeter using pulse oximetry, this oximeter is flawed for at least three reasons. First, the wavelengths of the electro-magnetic radiation used by the 789 Publication to determine fetal oximetry are short and consequently cannot travel a distance through the abdomen of the pregnant mammal so as to reach the fetus with sufficient strength. Thus, the signal reflected signal is too weak to decipher. Second, the 789 Publication is flawed because of the assumptions included therein are based on research with adult hemoglobin, which is fundamentally different from fetal hemoglobin because fetal hemoglobin has a different structure than adult hemoglobin and therefore absorbs/reflects light differently. Finally, the 789 Application does not process the received signal to reduce noise.

Like the 789 Publication, Patent WO 2009032168 describes a fetal oximeter using near-infrared spectroscopy but fails to provide a signal processing algorithm. In addition, the WO 2009032168 uses assumptions regarding adult hemoglobin to determine fetal oximetry, which yields inaccurate results because, as noted above, fetal hemoglobin and adult hemoglobin have different structures and, therefore reflect light differently.

U.S. Patent Publication No. 2011/0218413 describes an algorithm for signal processing that uses maternal electrocardiography (ECG), Doppler, and pulse oximetry. However, for at least the reasons pointed out above, trying to obtain a fetal oximetry signal using maternal (i.e., adult)

pulse oximetry won't work. Furthermore, the '413 Publication fails to make any compensation for structural differences in fetal and adult hemoglobin.

U.S. Patent Publication No. 2011/0218413 provides another example wherein a pregnant mammal wears a belt that shines light towards the belly and fetus that is detected on the other side of the abdomen. The distance traveled by the light would be 15-30 inches, or 35 to 75 cm, and this is not technically feasible because the signal received by the detector would be too weak to decipher. The light loses intensity quickly and there are FDA limitations on how intense the light directed into a pregnant mammal's abdomen can be because light that is too intense could cause, for example, burns to the pregnant mammal and retinal damage to the fetus.

SUMMARY

Disclosed herein are systems, devices, and methods for performing trans-abdominal fetal oximetry and/or trans-abdominal fetal pulse oximetry. The systems, devices, and methods may be performed using one or more fetal hemoglobin probes that are in contact with an abdomen of pregnant mammal (i.e., attached to the pregnant mammal via an adhesive, strap, harness, etc.). In some embodiments, all, or a portion of, a fetal hemoglobin probe may not be in contact with the pregnant mammal's abdomen as may be the case when performing a contactless pulse oximetry measurement and calculation. When a contactless pulse oximetry measurement and calculation is used, fetal hemoglobin probe and/or parts thereof may be positioned above the pregnant mammal's abdomen on, for example, a scaffold or cart.

Exemplary fetal hemoglobin probes disclosed herein may include a housing, a plurality of light sources, one or more detectors, a transceiver, and a power source. Exemplary systems disclosed herein include one or more fetal hemoglobin probes and a processor or computer that may be coupled with a display device (e.g., monitor or touch screen). More particularly, the housing of a fetal hemoglobin probe may be configured to house a first light source, a second light source, a detector, a transceiver, and a power source. In some cases the housing, first light source, second light source, detector, transceiver, and/or power source are configured to be disposable following a single use.

The first light source adapted to project light of a first wavelength into the abdomen of a pregnant mammal toward a fetus contained therein and the second light source adapted to project light of a second wavelength into the abdomen of the pregnant mammal toward the fetus. In some instances, the first and second light sources may reside in a single light housing configured with multiple light sources (e.g., LEDs) and, in other instances, the first and second light sources may be separately housed. Exemplary wavelengths for light emitted from the first light source may be between 700 nm and 740 nm and exemplary wavelengths for light emitted from the second light source may be between 800 and 900 nm.

The detector may be adapted to detect light reflected from the pregnant mammal's abdomen and the fetus. Exemplary detectors include but are not limited to photo detectors, light sensors, photodiodes and cameras. When the detector is a photo detector (or the like) the detector may also convert the detected light into an electronic reflected signal and communicate the electronic reflected signal to the transceiver.

The transceiver may be adapted to receive the electronic reflected signal from the detector and communicate the received electronic reflected signal to a processor or computer. The transceiver may be any device capable of receiving information from the detector and communicating information from the fetal hemoglobin probe.

The power source may be electrically coupled to the first light source, the second light source, and the detector and adapted to provide electrical power to first light source, the second light source, the detector, and the transceiver. Exemplary power sources include, but are not limited to, batteries and equipment to couple the fetal hemoglobin probe to a conventional power source (e.g., wall socket).

The processor may be configured to receive the electronic reflected signal from the detector and isolate a portion of the reflected electronic signal that is reflected from the fetus. The processor may then analyze the isolated portion of the reflected electronic signal to determine a fetal hemoglobin oxygen saturation level and provide an indication of the oxygen level of fetal blood to a display device, such as a monitor.

In some embodiments, the system may include an adjustment mechanism coupled to at least one of the first and second light sources. The adjustment mechanism may be adapted to adjust, for example, a frequency of light emitted by the respective first and/or second light sources, an incident angle of the light emitted by the respective first and/or second light sources when projected into the pregnant mammal's abdomen, and focus a beam of light as it is projected into the pregnant mammal's abdomen as it emitted from the respective first and/or second light sources.

In one exemplary embodiment, the system further includes an adjustment device coupled to the housing, or a portion thereof. The adjustment device may be adapted to adjust, for example, a frequency of light emitted by the respective first and second light sources, an incident angle of the light emitted by the respective first and/or second light sources when projected into the pregnant mammal's abdomen, and focus a beam of light as it is projected into the pregnant mammal's abdomen as it emitted from the respective first and/or second light sources.

In some embodiments, the system may include an additional detector, the additional detector may be positioned within the housing and coupled to the transceiver and power source. The additional detector may be adapted to detect light reflected from the pregnant mammal's abdomen and the fetus, convert the detected light into an additional electronic reflected signal, and communicate the additional electronic reflected signal to the transceiver and/or processor or a computer.

In some embodiments, the system and/or fetal hemoglobin probe may include four or more additional light sources housed within the housing, or housed in a separate housing. Each of the additional light sources being coupled to a power source. These embodiments may also include an additional detector. The additional detector may be positioned within the housing and coupled to the transceiver and power sources and may be adapted to detect light reflected from the pregnant mammal's abdomen and the fetus, convert the detected light into an additional electronic reflected signal, and communicate the additional electronic reflected signal to the transceiver and/or processor or a computer. In these embodiments, the housing may be adapted to have a length of at least 10 cm so as to extend around a portion of the pregnant mammal's abdomen and direct light at multiple positions (e.g., two or more sides) of the fetus. In these embodiments, the detector may be positioned on a first side of the housing and the additional detector may be positioned on a second side of the housing and the light sources are positioned between the first and second sides of the housing.

In some cases, the system may include a temperature probe housed within the housing and coupled to the power supply and transceiver. The temperature probe may be adapted to measure a temperature of the pregnant mammal's abdomen and/or skin and communicate the temperature measurements to, for example, the transceiver and/or controller. At times, a temperature measurement in excess of a threshold may indicate that the system is too hot and may cause injury to the pregnant mammal and/or fetus. When this happens, controller may shut off one or more components of the system and/or notify an operator of the pregnant mammal's elevated temperature.

In another embodiment, the system may include an ultrasonic detector being housed within the housing and coupled to the power supply and transceiver. The ultrasonic detector may be adapted to detect ultrasonic emissions of the pregnant mammal's abdomen and fetus caused by transient thermoelastic expansion resultant from an interaction of the pregnant mammal's abdomen and the fetus' tissue to light emitted from at least one of the first light source and the second light source due to the so-called photoacoustic effect.

In another embodiment, the system may further include a uterine contraction measurement that is housed within the housing and coupled to the power supply and transceiver, processor, and/or a computer. The uterine contraction measurement may be adapted to measure changes in a muscular state of the pregnant mammal's uterus and communicate these measurements to the transceiver, the processor, and/or a computer.

Exemplary methods described herein may include directing, by a light source, a light beam emitted from the light source into an abdomen of a pregnant mammal toward a fetus contained therein. Light reflected by the pregnant mammal and the fetus may be received at a detector over a first time domain. The detector may then convert the received light into an electronic reflected signal and communicate the electronic reflected signal to a computer/processor.

The computer may then process the electronic reflected signal to isolate a portion of the electronic reflected signal reflected from the fetus and analyze the portion of the electronic reflected signal reflected from the fetus to determine a fetal hemoglobin oxygen saturation level of the fetus. The computer may then facilitate provision of an indication of the fetal hemoglobin oxygen saturation level to an operator, such as a doctor or medical technician.

In some embodiments, processing the electronic reflected signal to isolate a portion of the electronic reflected signal reflected from the fetus includes receiving a heartbeat signal for the pregnant mammal over a second time domain. The heartbeat signal indicates when, in the second time domain, a pregnant mammal's heartbeat occurs. The electronic reflected signal and the pregnant mammal's heartbeat signal may then be synchronized over the first time domain and the second time domain and a portion of the electronic received signal that corresponds in the synchronized first and second time domains with the heartbeat signal for the pregnant mammal may be determined. The portion of the electronic received signal that corresponds with the heartbeat signal for the pregnant mammal from the electronic received signal may then be subtracted electronic received signal.

In another embodiment, the processing of the electronic reflected signal to isolate a portion of the electronic reflected signal reflected from the fetus may include receiving a fetal heartbeat signal for the fetus over a second time domain. The fetal heartbeat signal may indicate when, in the second time domain, a fetal heartbeat occurs. The electronic reflected signal and the fetal heartbeat signal may then be synchronized over the first time domain and the second time domain and portions of the electronic reflected signal that correspond in the synchronized first and second time domains with individual heartbeats of the fetus as indicated by the received heartbeat signal for the fetus may be examined to determine the fetal hemoglobin saturation level of the fetus.

In a further embodiment, processing the electronic reflected signal to isolate a portion of the electronic reflected signal reflected from the fetus comprises receiving a fetal heartbeat signal for the fetus over a second time domain, the heartbeat signal indicating when, in the second time domain, a fetal heartbeat occurs. The electronic reflected signal and the fetal heartbeat signal might then be synchronized over the first time domain and the second time domain. Then, the synchronized electronic reflected signal may be multiplied by the synchronized fetal heartbeat signal.

BRIEF DESCRIPTION OF THE FIGURES

The present invention is illustrated by way of example, and not limitation, in the figures of the accompanying drawings in which:

FIG. 7A provides a table of various hemoglobin measurements as a function of light wavelength shone into the blood of an adult donor and fetal blood obtained by puncture of the umbilical cord immediately after delivery, consistent with an embodiment of the invention;

Figure 1A:
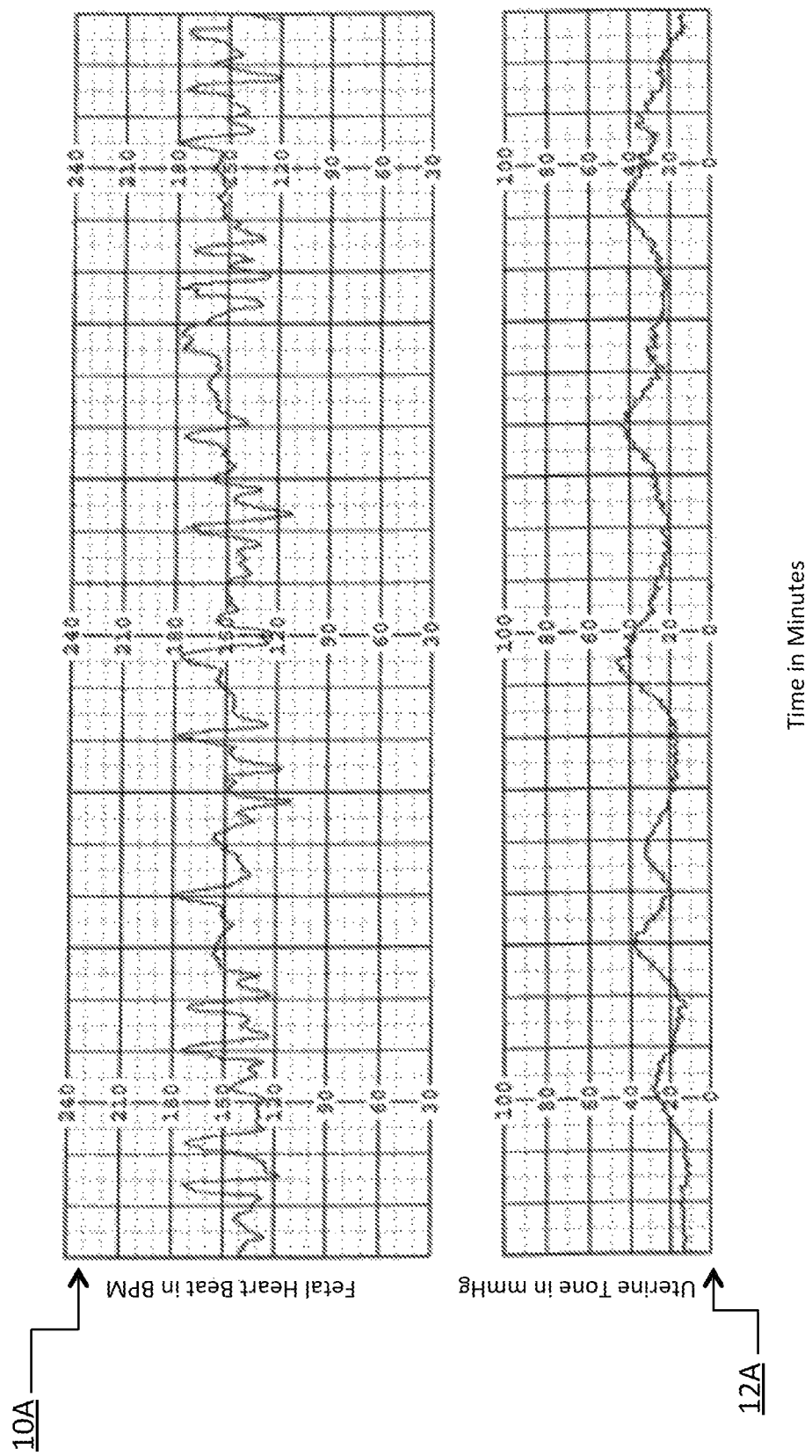
FIGS. 1A and 1B provide examples of simultaneously displayed fetal heartbeat and uterine tone for corresponding moments in time.
Figure 1B:
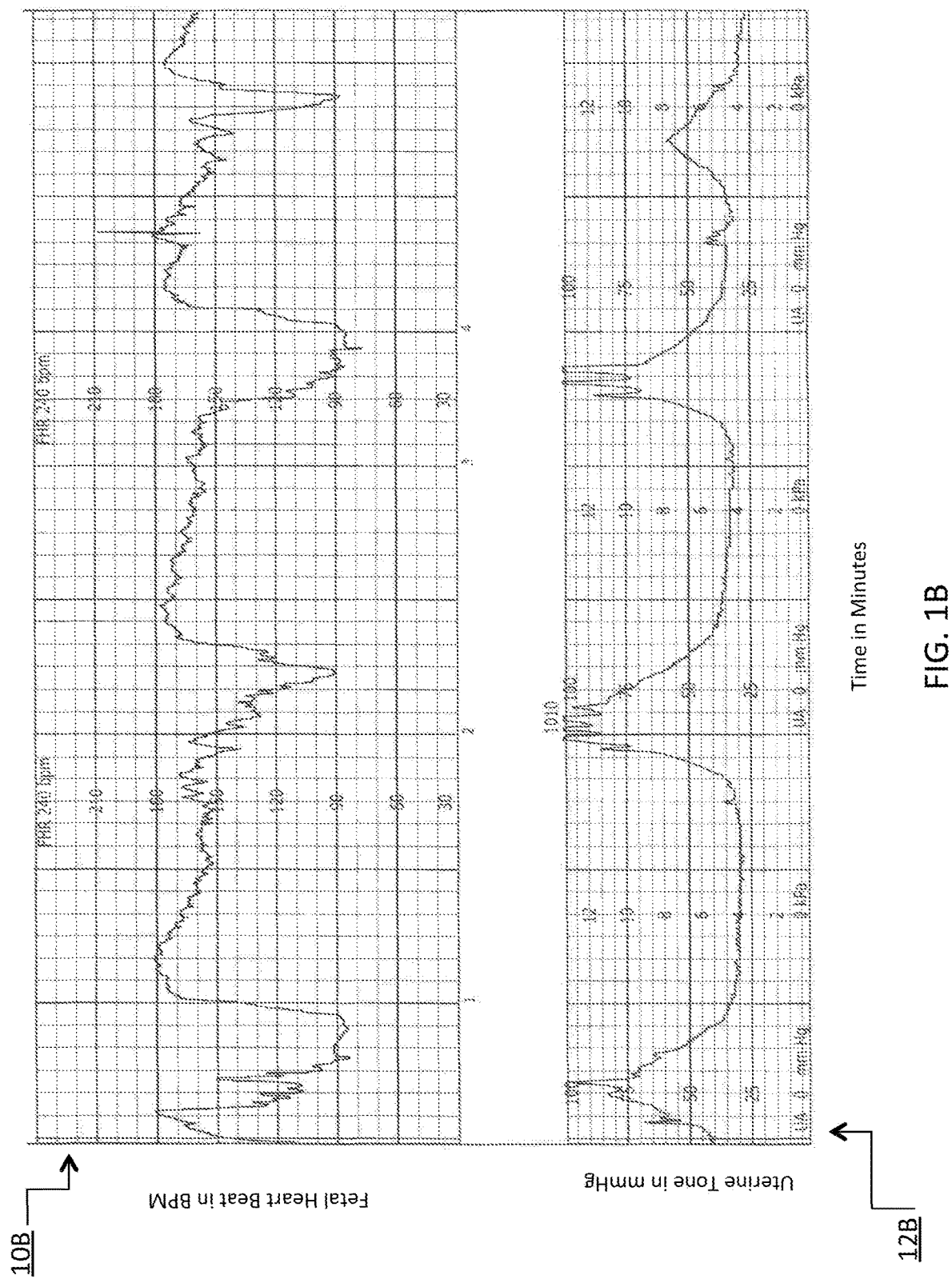

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

DESCRIPTION

Described herein are systems, devices, and methods for fetal oximetry and/or fetal pulse oximetry both trans-abdominally and in-utero. A key output of fetal oximetry and/or fetal pulse oximetry is the level of oxygen saturation of the fetus's blood (also referred to herein as "fetal hemoglobin oxygen saturation level" and "oxygen saturation level", which may also be understood as the percentage of hemoglobin present in the fetus' blood that is bound to oxygen. The oxygen saturation level of a fetus' blood may be used by trained medical professionals to assess the health of a fetus as well as a level of stress it may be under during, for example, a labor and delivery process. Typically values of oxygen saturation for fetal blood fall within the range of 30-60% with anything lower than 30% indicating that the fetus may be in distress.

For the purposes of the following discussion, the terms "pregnant mammal" or "maternal" "mother" is used to refer to female human being or animal (e.g., horse or cow) pregnant with a fetus. In most embodiments, the pregnant individual will be a human being but this need not be the case as the invention may be used for nearly any pregnant mammal. Whether, or not, the pregnant mammal is the biological mother of the fetus (i.e., source of the egg from which the fetus grows) is not relevant to this invention. What is relevant is that the woman is pregnant with the fetus.

Typically, fetal wellbeing is assessed during labor and delivery by looking at the absolute fetal heart rate as measured in beats per minute and observing how fetal heart rate changes, or reacts to, uterine contractions. It is generally accepted that a fetal heart rate within the range of 120-160 beats per minute is normal and does not indicate fetal distress. However, sudden changes in fetal heart rate as well as fetal heart rates that are too high (e.g., 180 beats per minute) or too low (e.g., 100 or 80 beats per minute) are cause for concern, especially if these changes occur during a prolonged, difficult, or otherwise complicated labor and delivery process.

For example, as the uterus contracts to expel the baby out of the birth canal, the contracting uterus constricts the blood vessels and hence blood flow to and from the placenta, which supplies blood to and from the fetus. It is expected that restricted blood flow to the fetus may result in a slowing of the fetal heart rate. However, a drop in fetal heart rate from 150 to 120 after every uterine contraction may be an indication of fetal distress and may prompt intervention (e.g., a C-section, drug administration, etc.) by a physician or other clinician during the birthing process.

However, in some instances, this intervention may not be necessary because not all drops in fetal heart rate are caused by fetal distress. In fact, the fetus is frequently just fine when its heart rate changes—but the physician has no further information to assist in determining whether the change in fetal heart rate is normal or pathological. Thus, an indication of the oxygen saturation level of the fetus' hemoglobin would be a useful additional indication of fetal wellbeing when, for example, determining whether to intervene in the labor and delivery process with surgery or other treatment administration. For example, an indication that the fetal hemoglobin oxygen saturation level is constant provides an indication to the physician that the fetus is in good health even when the heart rate of the fetus drops or changes. Conversely, a drop in the fetal hemoglobin oxygen saturation level following uterine contractions coupled with a decreasing heart rate would be a cause for concern and may indicate to the physician that an intervention, like a C-section, is necessary.

Currently, many C-sections are performed solely because of variations in, or drops of, fetal heart rate, which are seen by physicians as a sign of fetal distress. 2 million C-sections are performed annually in the United States and, in some regions of the United States, C-sections are performed in nearly half (50%) of all births. In some instances, these C-sections may not be necessary because the fetus may not truly be in distress. However, without further information (as may be provided via fetal pulse oximetry), physicians may over-prescribe C-sections and other interventions out of an abundance of caution The present invention provides a more complete picture of fetal health during the labor and delivery process and may thereby reduce the number of unnecessarily performed C-sections when the decision to perform a C-section is based on fetal heart rate readings alone. It is expected that reducing the number of unnecessarily performed C-sections will reduce the overall cost of health care for pregnant women and newborns and reduce the number of complications that result from C-sections, which can be very significant. For example, 1 in 1000 C-sections will result in a major complication such as a blood clot, requirement of a blood transfusion, or surgical wound infection and 1 in 10,000 C-sections will result in death of the mother.

Fetal hemoglobin has a structure that is slightly different from the structure hemoglobin of adult hemoglobin. More specifically, adult hemoglobin has 2 alpha and 2 beta polypeptide chains and fetal hemoglobin has 2 alpha and 2 gamma polypeptide chains. Additionally, fetal hemoglobin has a stronger affinity for oxygen than adult hemoglobin. Because of these factors, fetal hemoglobin absorbs light differently than maternal hemoglobin.

Additionally, fetal hemoglobin has a conformation when bound to oxygen that is different from the conformation of the fetal hemoglobin when unbound to oxygen. These different conformations of the hemoglobin absorb light at different amounts and hence reflect light at different amounts. Therefore, observation of fetal venous hemoglobin oxygen saturation levels may be clinically more useful than fetal arterial hemoglobin oxygen saturation levels.

Disclosed herein are systems, devices, and methods for performing non-invasive in-utero fetal oximetry using near infrared spectroscopy (NIRS) to determine the oxygen saturation level of arterial and/or venous fetal hemoglobin. The determined oxygen saturation level of arterial and/or venous fetal hemoglobin may then be used by, for example, a physical or other caregiver to ascertain information regarding fetal health and/or distress. In some embodiments, the systems, devices, and methods may employ a non-invasive monitor that can be placed on a pregnant mammal's abdomen to monitor fetal oxygen saturation levels.

Because fetal hemoglobin is microscopic, it cannot be observed directly. However, reflections of near infrared light from the fetal hemoglobin may be observed. Furthermore, different intensities for different wavelengths of light that are reflected by the fetal hemoglobin may also be observed. Additionally, different intensities for light that is reflected by fetal oxyhemoglobin when compared to fetal de-oxyhemoglobin may also be observed. Processing of this observed reflected light might yield a determination of a fetal oxygen saturation level.

Figure 2A:
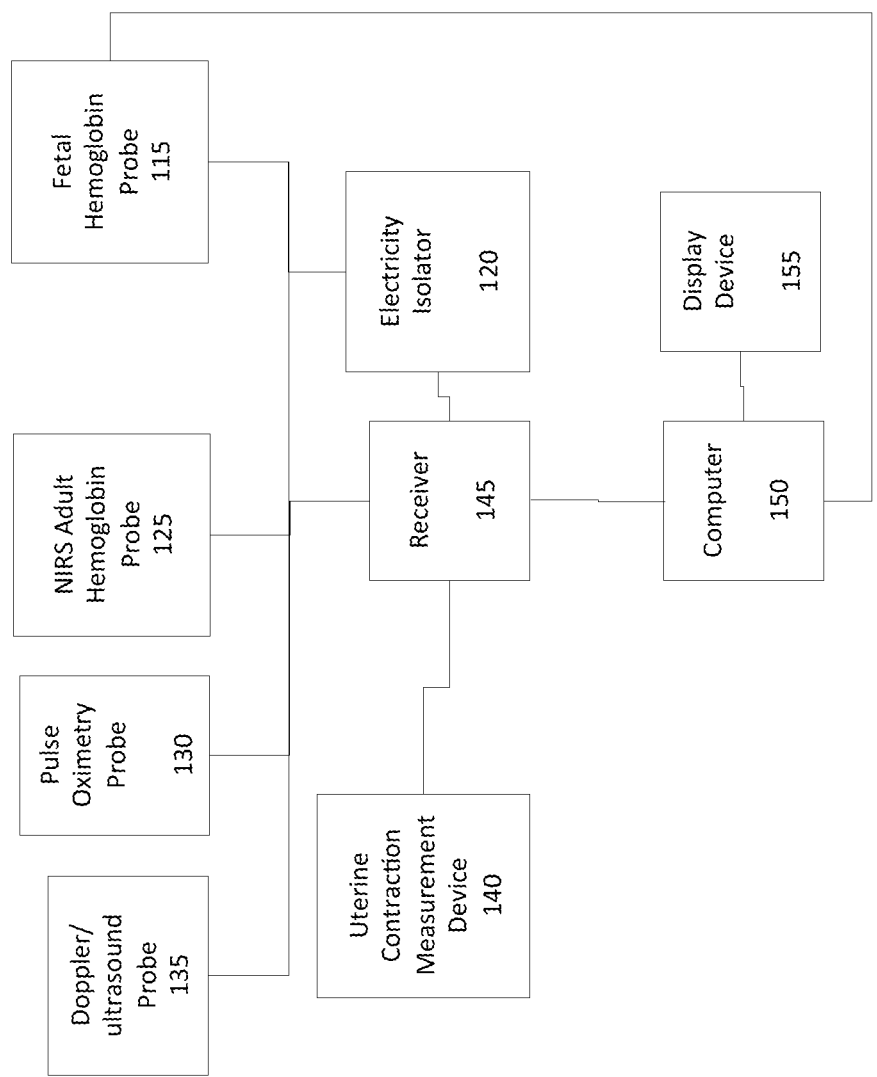
FIG. 2A provides an exemplary system 100 for determining a fetal oxygen level, consistent with an embodiment of the invention.

FIG. 2A provides an exemplary system 100 for determining a fetal oxygen level and, in some instances, detecting and/or determining fetal hemoglobin oxygen saturation levels. The components of system 100 may be coupled together via wired or wireless communication links. In some instances wireless communication of one or more components of system 100 may be enabled using short-range wireless communication protocols designed to communicate over relatively short distances (e.g., BLUETOOTH® near field communication (NFC), radio-frequency identification (RFID), and Wi-Fi) with, for example, a computer or personal electronic device as described below. In some embodiments, one or more components of system 100 may include one or more devices configured to communicate via one or more short-range communication protocols (e.g., near field communication (NFC), Bluetooth, Radio-frequency identification (RFID), and Wi-Fi).

System 100 includes a number of independent sensors/probes designed to monitor various aspects of maternal and/or fetal health and be in contact with a pregnant mammal. These probes/sensors are a fetal hemoglobin probe 115, a NIRS adult hemoglobin probe 125 a pulse oximetry probe 130, and a Doppler and/or ultrasound probe 135. In some embodiments, system 100 may also include an electrocardiography (EKG, or ECG) machine (not shown) that may be used to determine the pregnant mammal's and/or fetus' heart rate and/or an intrauterine pulse oximetry probe that may be used to determine the fetus' heart rate. The Doppler and/or ultrasound probe 135 may be configured to be placed on the abdomen of the pregnant mammal and may be of a size and shape that approximates a silver U.S. dollar coin. Pulse oximetry probe 130 may be a conventional pulse oximetry probe placed on pregnant mammal's hand and/or finger to measure the pregnant mammal's oxygen saturation. NIRS adult hemoglobin probe 125 may be placed on, for example, the pregnant mammal's 2nd finger and may be configured to, for example, use near infrared spectroscopy to calculate the ratio of adult oxyhemoglobin to adult de-oxyhemoglobin. NIRS Adult hemoglobin probe 125 may also be used to determine the pregnant mammal's heart rate.

Optionally, system 100 may include a uterine contraction measurement device 140 configured to measure the strength and/or timing of the pregnant mammal's uterine contractions. In some embodiments, uterine contractions will be measured by uterine contraction measurement device 140 as a function of pressure (measured in e.g., mmHg) over time. In some instances, the uterine contraction measurement device 140 is and/or includes a tocotransducer, which is an instrument that includes a pressure-sensing area that detects changes in the abdominal contour to measure uterine activity and, in this way, monitors frequency and duration of contractions.

In another embodiment, uterine contraction measurement device 140 may be configured to pass an electrical current through the pregnant mammal and measure changes in the electrical current as the uterus contracts. Additionally, or alternatively, uterine contractions may also be measured via near infrared spectroscopy because uterine contractions, which are muscle contractions, are oscillations of the uterine muscle between a contracted state and a relaxed state. Oxygen consumption of the uterine muscle during both of these stages is different and these differences may be detectable using NIRS.

Measurements from NIRS adult hemoglobin probe 125, pulse oximetry probe 130, Doppler and/or ultrasound probe 135, and/or uterine contraction measurement device 140 may be communicated to receiver 145 for communication to computer 150 and display on display device 155. In some instances, one or more of NIRS adult hemoglobin probe 125, pulse oximetry probe 130, a Doppler and/or ultrasound probe 135, uterine contraction measurement device 140 may include a dedicated display that provides the measurements to, for example, an operator or medical treatment provider.

As will be discussed below, measurements provided by NIRS adult hemoglobin probe 125, pulse oximetry probe 130, a Doppler and/or ultrasound probe 135, uterine contraction measurement device 140 may be used in conjunction with fetal hemoglobin probe 115 to isolate a fetal pulse signal and/or fetal heart rate from a maternal pulse signal and/or maternal heart rate.

It is important to note that not all of these probes may be used in every instance. For example, when the pregnant mammal is using fetal hemoglobin probe 115 in a setting outside of a hospital or treatment facility (e.g., at home or work) then, some of the probes (e.g., NIRS adult hemoglobin probe 125, pulse oximetry probe 130, a Doppler and/or ultrasound probe 135, uterine contraction measurement device 140) of system 100 may not be used.

Receiver 145 may be configured to receive signals and/or data from one or more components of system 100 including, but not limited to, fetal hemoglobin probe 115, NIRS adult hemoglobin probe 125, pulse oximetry probe 130, Doppler and/or ultrasound probe 135, and/or uterine contraction measurement device 140. Communication of receiver 145 with other components of system may be made using wired or wireless communication.

In some instances, receiver 145 may be configured to process or pre-process received signals so as to, for example, make the signals compatible with computer 150 (e.g., convert an optical signal to an electrical signal), improve SNR, amplify a received signal, etc. In some instances, receiver 145 may be resident within and/or a component of computer 150. Also, while receiver 145 is depicted in FIG. 2A as a single receiver, that is not necessarily the case as any number of appropriate receivers (e.g., 2, 3, 4, 5) may be used to receive signals from system 100 components and communicate them to computer 150. In some embodiments, computer 150 may amplify or otherwise condition the received reflected signal so as to, for example, improve the signal-to-noise ratio.

Receiver 145 may communicate received, pre-processed, and/or processed signals to computer 150. Computer 150 may act to process the received signals, as discussed in greater detail below, and facilitate provision of the results to a display device 155. Exemplary computers 150 include desktop and laptop computers, servers, tablet computers, personal electronic devices, mobile devices (e.g., smart phones), and so on. Exemplary display devices 155 are computer monitors, tablet computer devices, and displays provided by one or more of the components of system 100. In some instances, display device 155 may be resident in receiver 145 and/or computer 150.

Fetal hemoglobin probe 115 may be used to direct NIR light into the abdomen of the pregnant mammal so as to reach the fetus and to detect light reflected from the fetus. The NIR light may be emitted by fetal hemoglobin probe 115 in, for example, a continuous and/or pulsed manner. This reflected light might then be processed in order to determine how much light, at various wavelengths, is reflected and/or absorbed by the fetal oxyhemoglobin and/or de-oxyhemoglobin so that a fetal hemoglobin oxygen saturation level may be determined. This processing will be discussed in greater detail below. In some embodiments, fetal hemoglobin probe 115 may be configured, partially or wholly, as a single-use, or disposable, probe that is affixed to the pregnant mammal's skin on, for example, the pregnant mammal's abdomen and, in some embodiments, in the supra-pubic (bikini) region.

Exemplary dimensions for fetal hemoglobin probe 115 include, but are not limited to, 2-16 inches in length and 0.5-8 inches in width. In some instances, fetal hemoglobin probe 115 may come in a variety of sizes so as to, for example, accommodate varying clinical needs, the size of the fetus, fetal position, the size of the pregnant mammal, and/or the size of the pregnant mammal's abdomen.

Fetal hemoglobin probe 115 may include one or more components as will be described in greater detail below with regard to FIGS. 2B-2E, of which the fetal hemoglobin probes of FIGS. 2B-2D (i.e., 115A, 115B, 115C, and 115D) are trans-abdominal fetal hemoglobin probes. The fetal hemoglobin probes 115 disclosed herein may include a housing 102 configured to house one or more components of fetal hemoglobin probe 115. Although the embodiments disclosed herein have all of the components of fetal hemoglobin probes 115 contained within a single housing 102, this is not necessarily the case as, for example, two or more components of a fetal hemoglobin probe 115 may be housed in separate housings 102. Housings 102 may be, for example, square, circular, or rectangular in shape and may be designed to be, in some instances, adjustable depending on, for example, a topology of the pregnant mammal's abdomen, a level of skin pigmentation for the pregnant mammal and/or her fetus, and so on.

In some embodiments, fetal hemoglobin probe 115 and/or housing 102 may be disposable and in other embodiments, fetal hemoglobin probe 115 (including and/or housing 102) may be configured for multiple uses (i.e., reusable). In some embodiments, (e.g., when fetal hemoglobin probe is configured to be disposable), may include an adhesive designed to be applied to the skin of the pregnant mammal's abdomen (e.g., glue, tape, etc.) configured to apply housing 102/fetal hemoglobin probe 115 directly to the skin of the pregnant mammal's abdomen and hold it in place there in a manner similar to a sticker. In some instances, the fetal hemoglobin probe 115 may be applied to the pregnant mammal's skin via tape or a strap that cooperates with a mechanism (e.g., snap, loop, etc.) (not shown) provided by the housing 102. In some circumstances, housing 102 may be attached/adjacent to the pregnant mammal's skin so that it does not move and, in other instances, it may be allowed to move in order to, for example, attain better measurements/readings. In some cases, housing 102 and/or a portion thereof may not be adapted to be in contact with the pregnant mammal's abdomen.

In some embodiments, housing 102 and/or a portion thereof may cooperate with a reusable and/or disposable sleeve (not shown) that fits over fetal hemoglobin probe 115 so that fetal hemoglobin probe 115 may be placed within a housing 102 reusable and/or disposable sleeve so that it may be applied to the pregnant mammal's skin.

Fetal hemoglobin probe 115 may be adapted to direct, or shine, light of one or more wavelengths into the abdomen of a pregnant mammal and receive a signal corresponding to a reflection of a portion of that light from the pregnant mammal's tissue and fluid as well as the tissue and fluids of the fetus.

Optionally, fetal hemoglobin probe 115 may include one or more mechanisms that enable the emitted light to be directed in a particular direction. Such mechanisms include, but are not limited to, wedges or adhesive material, that may be transparent or substantially transparent. For example, a fetal hemoglobin probe 115 may include a wedge positioned on one side that operates to direct the light in a particular direction relative to the surface of the pregnant mammal's skin and/or position a detector or transceiver to receive an optimized amount of reflected light.

In some embodiments, a fetal hemoglobin probe 115 may be adapted to be worn by a pregnant mammal for an extended period of time (e.g., days, weeks, etc.) that is not necessarily coincident with the labor and delivery process in order to, for example, monitor the health of a fetus. In some embodiments, one or more components of fetal hemoglobin probe 115 may be positioned outside the fetal hemoglobin probe 115 and may be optically connected thereto via, for example, one or more fiber optic or Ethernet cable(s).

A fetal hemoglobin probe 115 may be of any appropriate size and, in some circumstances, may be sized so as to accommodate the size of the pregnant mammal using any appropriate sizing system (e.g., waist size and/or small, medium, large, etc.). Exemplary lengths for a fetal hemoglobin probe 115 include a length of 4 cm-40 cm and a width of 2 cm-10 cm. In some circumstances, the size and/or configuration of a fetal hemoglobin probe 115, or components thereof, may be responsive to skin pigmentation of the pregnant mammal and/or fetus.

It will be understood that although the components of fetal hemoglobin probe 115 are described herein as being included in a single probe, that is not necessarily so as the components of fetal hemoglobin probe 115 may be present in two or more different objects/devices applied to a pregnant mammal. In some instances, more than one fetal hemoglobin probe 115 may be used so as to, for example, improve accuracy of the fetal oxygen saturation measurement. For example, a first fetal hemoglobin probe 115 (or a component thereof) may be placed on a left side of a pregnant mammal's abdomen and a second fetal hemoglobin probe 115 (or a component thereof) may be placed on a right side of the pregnant mammal's abdomen.

In some embodiments, fetal hemoglobin probe 115 and/or a pregnant mammal wearing a fetal hemoglobin probe 115 may be electrically insulated from one or more components of system 100 by, for example, an electricity isolator 120. Exemplary electricity insulators 120 include circuit breakers, ground fault switches, and fuses.

Figure 2B:
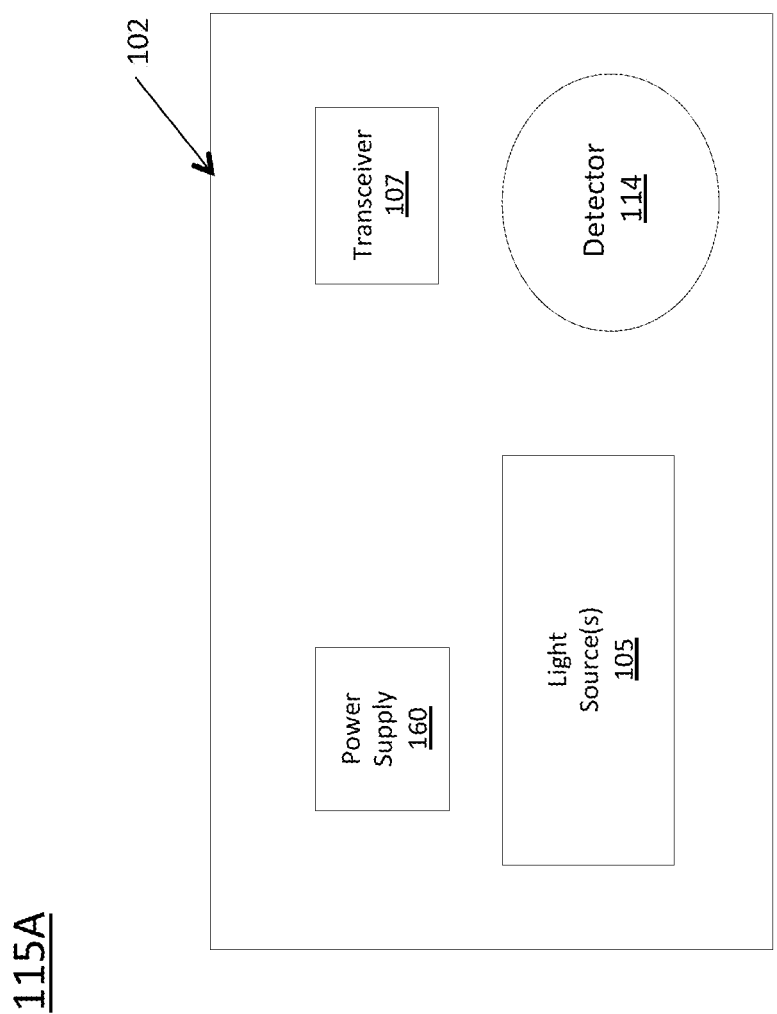
FIGS. 2B-2E provide block diagrams of exemplary fetal hemoglobin probes, consistent with embodiments of the invention.

Turning now to FIGS. 2B-2E, which show different embodiments of exemplary fetal hemoglobin probes 115 labeled as 115A, 115B, 115C, and 115D, respectively, intended to be used trans-abdominally. It will be understood that reference to fetal hemoglobin probe 115 made herein may also refer to, and include, other embodiments of fetal hemoglobin probe including fetal hemoglobin probe 115A, fetal hemoglobin probe 115B, fetal hemoglobin probe 115C, and fetal hemoglobin probe 115D. FIG. 2B illustrates exemplary fetal hemoglobin probe 115A, which includes a power supply 160, light source(s) 105, a transceiver 107, and a detector 114.

Exemplary power supplies 160 include an on-board battery and/or an electrical connection to an external power source. Detector 114 may be adapted to receive a light signal reflected from the pregnant mammal and/or the fetus and convert this light signal into an electronic signal, which may be communicated to transceiver 107. Some embodiments of fetal hemoglobin probe 115 may not include a transceiver 107 as may be the case when, for example, detector 114 is in direct communication with, for example, computer 150. Exemplary detectors 114 include, but are not limited to, cameras, traditional photomultiplier tubes (PMTs), silicon PMTs, avalanche photodiodes, and silicon photodiodes. In some embodiments, the detectors will have a relatively low cost (e.g., $50 or below), a low voltage requirement (e.g., less than 100 volts), and non-glass (e.g., plastic) form factor. However, these alternatives do not have the same sensitivity to PMTs. In other embodiments, (e.g., contactless pulse oximetry) an extremely sensitive camera may be deployed to receive light reflected by the pregnant mammal's abdomen.

Light source(s) 105 may transmit light at various wavelengths, including NIR, into the pregnant mammal's abdomen. Typically, the light emitted by light source(s) 105 will be focused or emitted as a narrow beam so as to reduce spreading of the light upon entry into the pregnant mammal's abdomen. Light source(s) 105 may be, for example, a LED and/or a LASER. In some embodiments, light source(s) 105 may be an array of two or more light source(s) 105 as will be discussed below with regard to FIGS. 2C-2E. An exemplary light source 105 is one with a relatively small form factor and high efficiency so as to limit heat emitted by the light source 105. In one embodiment, light source 105 is configured to emit light at 850 nm an example of which is the LED in Dragon Dome Package that Emits Light of 850 nm manufactured by OSRAM Opto Semiconductors (model number SFH 4783), which has a length of 7.080 mm and a width of 6.080 mm. Another exemplary light source 105 is a LED configured to emit light of 730 nm, such as the GF CSHPM1.24-3S4S-1 manufactured by OSRAM Opto Semiconductors, which has a height of 1.58 mm and a length of 3.1 mm. Exemplary flux ratios for light source(s) include, but are not limited to a luminous flux/radiant flux of 175-260 mW, a total radiant flux of 300-550 mW and a power rating of 0.6 W-3.5 W.

In some embodiments, one or more light sources 105 may be a fiber optic cable transmitting light produced by another source (e.g., a LASER or tunable light bulb or LED) not resident within fetal hemoglobin probe 115. In some instances, the light source(s) 105 may be tunable or otherwise user configurable while, in other instances, one or more of the light sources may be configured to emit light within a pre-defined range of wavelengths. Additionally, or alternatively, one or more filters (not shown) and/or polarizers may filter/polarize the light emitted by light source(s) 105 to be of one or more preferred wavelengths. These filters/polarizers may also be tunable or user configurable.

In some embodiments, the fetal hemoglobin probe 115 may direct NIR light of a plurality of wavelengths (e.g., 7, 6, 5, 4, 3, 2) via light sources 105. In a preferred embodiment, five different wavelengths are used wherein a first wavelength is used to measure an oxygen saturation level of adult oxyhemoglobin, a second wavelength is used to measure an oxygen saturation level of adult de-oxyhemoglobin, a third wavelength is used to measure an oxygen saturation level of fetal oxyhemoglobin, and a fourth wavelength is used to measure an oxygen saturation level of fetal de-oxyhemoglobin. The fifth wavelength may be used to clean up/improve the signal by assisting in the detection of portions of the reflected signal that may be caused and/or distorted by substances other than the pregnant mammal's and/or the fetal hemoglobin. For example, melanin and bilirubin are known to absorb infrared light. Thus, in instances where the fetus and/or pregnant mammal has a darker pigment or when either or both are jaundiced, the associated melanin and/or bilirubin may distort the readings of the fetal hemoglobin probe 115 which may result in incorrectly calculating the oxygen saturation of the fetal and/or pregnant mammal's hemoglobin. The fifth wavelength may acts to test for these distortions so that they may be removed from the received signal and accurate oxygen saturation levels may be determined.

In some embodiments, detector 114 may be a sensitive camera adapted to capture small changes in fetal skin tone caused by changes in cardiovascular pressure as the fetus' heart beats. In these embodiments, fetal hemoglobin probe 115 may be in contact with the pregnant mammal's abdomen, or not, as this embodiment may be used to perform so-called contactless pulse oximetry. In these embodiments, light source(s) 105 of fetal hemoglobin probe 115 may be adapted to provide light (e.g., in the visible spectrum, near-infrared, etc.) directed toward the pregnant mammal's abdomen so that the detector 114 is able to receive light reflected by the pregnant mammal's abdomen and fetus. The reflected light captured by detector 114 in this embodiment may be communicated, via transceiver 107, to computer 150 for processing so as to convert the images to a measurement of fetal hemoglobin oxygen saturation according to, for example, one or more of the processes described herein.

In this embodiment, adjustment mechanism 122 may be adapted to, for example, focus light source(s) 105, change a frequency of light emitted by light source(s) 105, change a distance light source(s) 105 and/or detector 114 is positioned away from the surface of the pregnant mammal's abdomen, and/or change an incident location of the emitted light.

Optionally, fetal hemoglobin probe 115 may also include one or more polarizers (not shown). A polarizer may act to polarize one more of the wavelengths of light prior to emission by fetal hemoglobin probe 115. Polarizing the light and giving it a specific orientation may serve to, for example, assist in the identification of a signal and/or distinguish a desired signal from noise and thereby improve a signal to noise ratio (SNR) of the received signal.

Transceiver 107 may be configured to the electronic signal (corresponding to the reflected light signal detected by detector 114) from detector 114 and communicate the electronic signal to equipment (e.g., receiver 145 and/or computer 150) external to fetal hemoglobin probe 115 via, for example, a fiber optic cable (in the case of a light signal) and/or a wireless or a wired signal (e.g., via an Ethernet port or hard-wired connection in the case of an electrical signal). In some instances, transceiver 107 may be a solid-state transceiver. In some embodiments, transceiver 107 may be resident in and/or a part of detector 114 and may be configured to detect light and/or photons reflected from the pregnant mammal and fetus and convert the detected light/photons into an electrical signal.

Figure 2C:
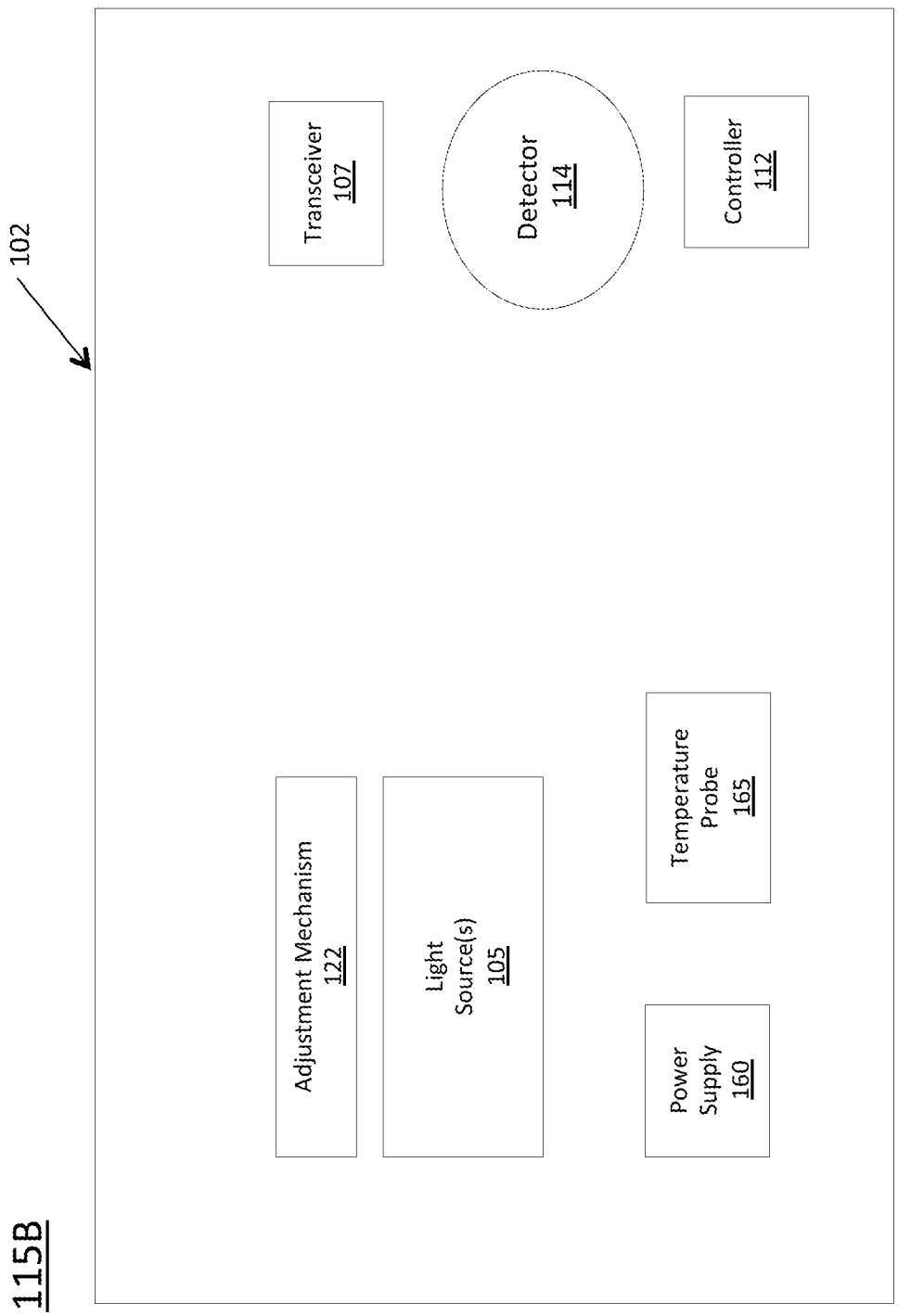

FIG. 2C shows another exemplary fetal hemoglobin probe 115b that includes power supply 160, light source(s) 105, transceiver 107, detector 114, an adjustment mechanism 122, a temperature probe 165, and a controller 112.

Temperature probe 165 may be any appropriate mechanism for obtaining a temperature measurement for the pregnant mammal. Adjustment mechanism 122 may be one or more mechanisms adapted to adjust one or more properties of the light emitted by light source(s) 105 and/or a direction/incident angle of the light directed into the abdomen of the pregnant mammal. Exemplary adjustment mechanisms include, but are not limited to, filters and polarizers that may be used to adjust a frequency/wavelength of the light emitted by light source(s) 105 and/or an orientation for the light. Other exemplary adjustment mechanisms 122 include lenses adapted to, for example, focus or spread light directed into the pregnant mammal's abdomen. In some instances, the lenses may also change the angle of incidence for the light directed to the pregnant mammal's abdomen. In some embodiments, adjustment mechanisms 122 may also include mechanisms enabled to move a light source 105 and/or operate a lens, filter, or polarizer. In some embodiments, adjustment mechanism 122 may include a material that is sensitive to electricity and may be enabled to become transparent and/or partially opaque upon application of electricity. Often times, adjustment mechanism(s) 122 may receive instructions from controller 112 that may control (wholly or partially) the operation of the adjustment mechanism 122.

Optionally, fetal hemoglobin probe 115 may also include one or more one or more ultrasonic detectors 170. An ultrasonic detector 170 may be employed in embodiments of fetal hemoglobin probe 115 configured to perform optoacoustic/photoacoustic and/or thermoacoustic imaging by way of directing a light or radio frequency pulse from light source(s) 105 into the pregnant mammal's 305 abdomen. A portion of the incident light may be absorbed by the fetus and pregnant mammal and converted into heat, which leads to transient thermoelastic expansion, which causes an ultrasonic emission from the fetus and pregnant mammal. This ultrasonic emission may be detected by ultrasonic detector 170 and analyzed to determine a level of oxygen saturation for the fetus' and/or pregnant mammal's blood. In some instances, deploying fetal hemoglobin probe 115 to perform optoacoustic/photoacoustic and/or thermoacoustic imaging may require use of a laser and/or radio frequency pulse emitter (not shown).

Controller 112 may be adapted to control one or more components (e.g., adjustment mechanism 122, light source(s) 105, power supply 160, temperature probe 165, detector 114, and/or transceiver 107) of fetal hemoglobin probe 115. In some circumstances, controller 112 may include a processor adapted to receive measurements/information from one more components (e.g., adjustment mechanism 122, light source(s) 105, power supply 160, temperature probe 165, detector 114, and/or transceiver 107) of fetal hemoglobin probe 115. The processor may be further adapted to process the received measurements, make decisions therewith, and communicate instructions based on those decisions and/or measurements to one or more components of fetal hemoglobin probe 115. For example, temperature probe 165 may act to measure the body temperature of the pregnant mammal and may provide these measurements to controller 112 and/or transceiver. In some embodiments, these measurements may be used to determine whether the temperature of the pregnant mammal exceeds a threshold measurement, which in some instances, may indicate that light source(s) 105 and/or fetal hemoglobin probe 115 are delivering too much heat/energy to the pregnant mammal. Upon reaching such a determination, controller 112 may provide instructions to light source(s) 105 and/or adjustment mechanism 122 to correct for this. Exemplary instructions include, but are not limited to, directions to redirect incident light, turn off, adjust a frequency, and adjust an intensity of one or more of the light source(s) 105.

In some instances, instructions provided by controller 112 may be based on, for example, feedback from, for example detector 114 and/or transceiver 107 regarding, for example, the strength/intensity of the reflected signal, the frequency/wavelength of light received in the reflected signal. For example, if controller 112, transceiver 107, and/or detector 114 determines that a received signal reflected from the pregnant mammal's abdomen is of insufficient strength/intensity, then controller 112 may provide instructions to adjustment mechanism 112 and/or light source(s) 105 to increase the intensity and/or wavelength/frequency of the light incident on the abdomen of the pregnant mammal.

In another example, temperature probe 165 may act to measure the body temperature of the pregnant mammal and may provide these measurements to controller 112 and/or transceiver. In some embodiments, these measurements may be used to determine whether the temperature of the pregnant mammal exceeds a threshold measurement, which in some instances, may indicate that light source(s) 105 and/or fetal hemoglobin probe 115 are delivering too much heat/energy to the pregnant mammal. Upon reaching such a determination, controller 112 may provide instructions to light source(s) 105 and/or adjustment mechanism 122 to correct for this. Exemplary instructions include, but are not limited to, directions to redirect incident light, turn off, adjust a frequency, and/or adjust an intensity of one or more of the light source(s) 105.

In some instances, light source(s) 105 may be tunable, or otherwise user configurable, by, for example, a physician or clinician assisting the pregnant mammal during the delivery process. For example, a light source 105 may be configured to emit light in multiple frequencies/wavelengths and/or intensities and the light source 105 may be tuned via, for example, direct physical manipulation of the light source 105 (e.g., via a button on knob), or the entering of an instruction regarding the desired frequency/wavelength and/or intensity into, for example, computer 150 and/or controller 112.

Tuning the frequency/wavelength and/or intensity of light emitted by one or more light source(s) 105 may be helpful in achieving a return signal of sufficient strength or clarity in a variety of circumstances (e.g., fetus position, fetus size, the amount of melanin in the skin of the pregnant mammal and/or fetus, the size and/or shape of the pregnant mammal, etc.). For example, light of a relatively higher intensity may be desired when the pregnant mammal has a relatively high body mass index (BMI) or body fat positioned in such a way as to inhibit the strength of a signal reflected from the fetus (i.e., return signal). In another example, a fetus may be positioned against the internal organs of the pregnant mammal (i.e., away from the skin of the belly), and light of relatively higher intensity and/or different wavelength may be desired so that the light reaches the fetus with a sufficiently strong signal so that a return signal may be detected by, for example, detector 114.

When fetal hemoglobin probe 115 includes more than one light source 105, the light sources 105 may be arranged in an array adapted to maximize the strength of the returned signal such as array 170 as discussed below with regard to FIGS. 2D and 2E. Array 170 may include any appropriate number of light sources 105. In some instances, array 170 may include a first row of a first type of light source 105A, 105B, through 105N and a second row of a second type of light source 105AA, 105AB, through 105AN. The different types of light sources may be configured to, for example, emit light of a particular frequency/wavelength and/or intensity. For example, light sources 105 A, 105B, through 105N may be configured to emit light with wavelengths in the red spectrum and light sources 105 AA, 105AB, through 105AN may be configured to emit light with wavelengths in the infrared or near-infrared spectrum. Although array 170 to have two rows, it will be appreciated that any number of rows (e.g., 3, 4, 5, 6, 7, 8, and so on) may be included in array 170.

Embodiments of fetal hemoglobin probe 115 with a relatively large length (e.g., 10 cm-40 cm) may have arrays 170 with rows of multiple light sources long fetal hemoglobin probe 115 that include, for example, 10, 15, 20, 25, 30, 35, 40, 45, or 50 light sources 105 each. A fetal hemoglobin probe 115 may also include more than one detector 114, as shown in FIG. 2E, which includes a first detector 114A and a second detector 114B. In some embodiments, first detector 114A may be the same as second detector 114B and, in other embodiments, they may be different. For example, first detector 114A may be sensitive to a first range of frequencies for reflected light and second detector 114B may be sensitive to a second range of frequencies for reflected light. Additionally, or alternatively, first detector 114A may be of a different size than second detector 114B. Any of the fetal hemoglobin probes 115 disclosed herein may include multiple detectors adapted to, for example, detect light reflected for one or more the light source(s) 105 included in array 170.

Figure 2D:
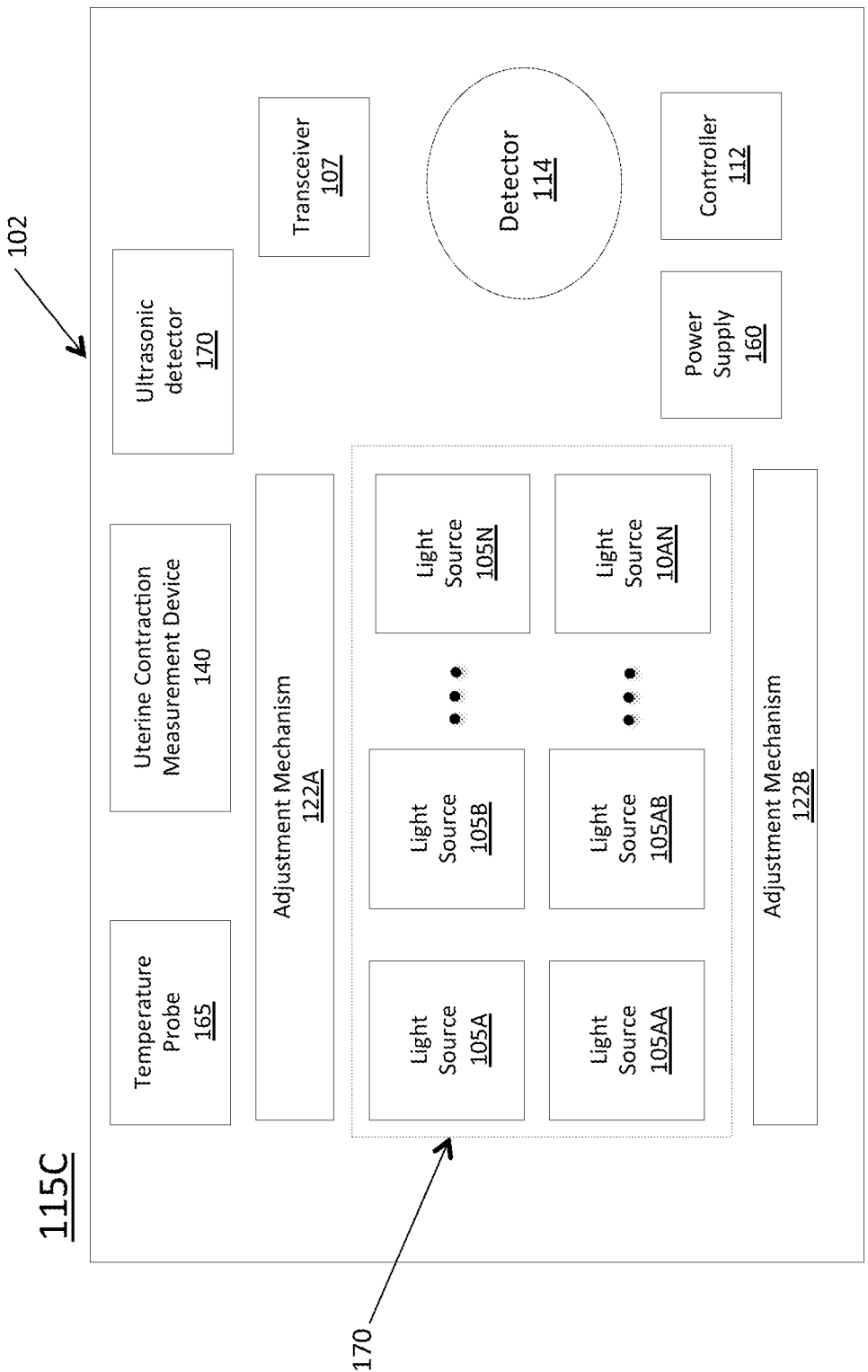
Figure 2E:
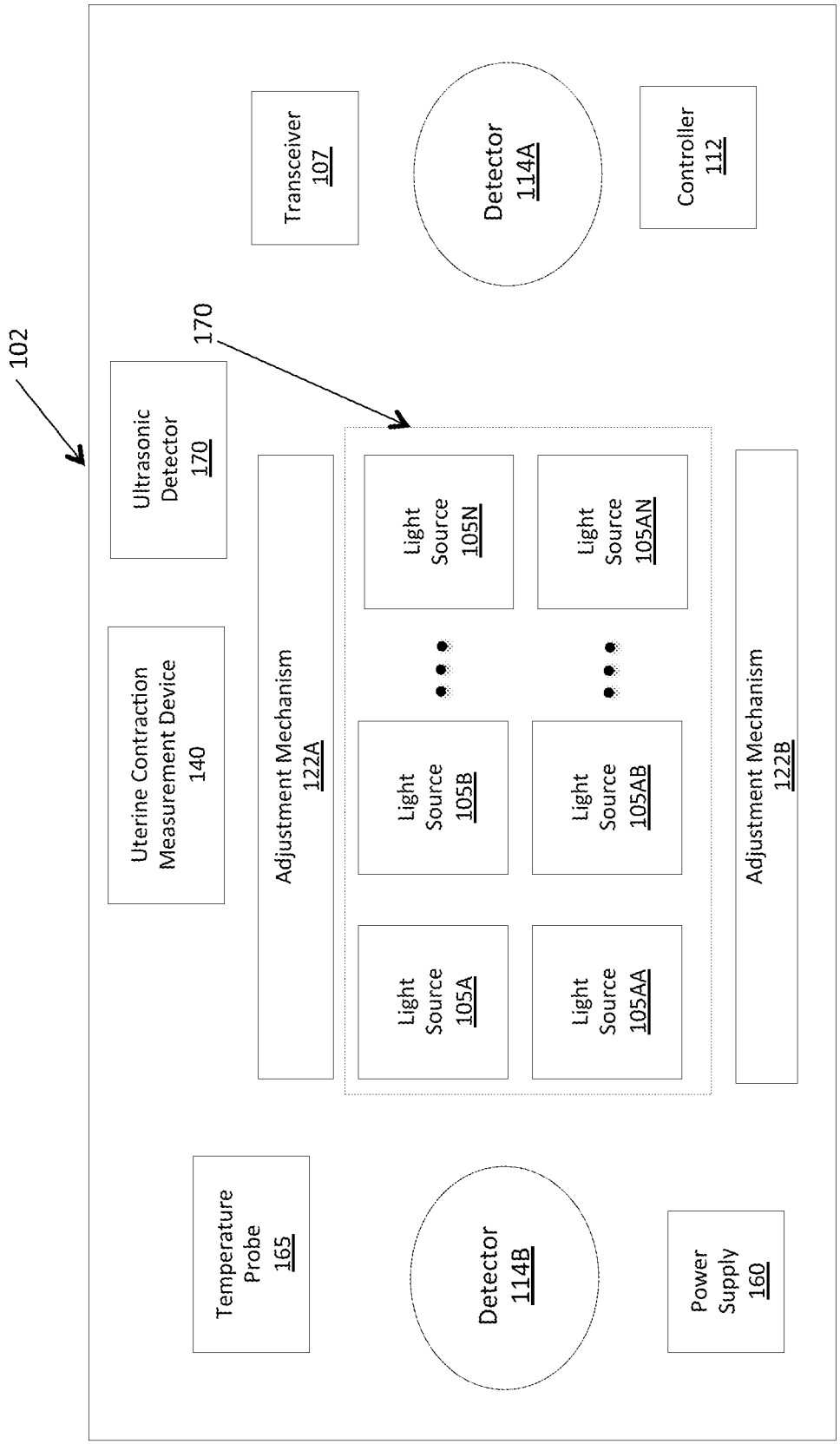

Although shown as a separate component in FIGS. 2C-2E, it will be appreciated by those of skill in the art that adjustment mechanism 122 may be partially and/or wholly positioned within and/or adjacent to one or more light sources 105.

Components of system 100 may be applied to a pregnant mammal in any acceptable manner. For example, NIRS adult hemoglobin probe 125 may be placed on the second finger of the pregnant mammal 305, pulse oximetry probe 130 may be placed on the thumb of the pregnant mammal 305, and Doppler and/or ultrasound probe 135 may be placed on the abdomen of the on the pregnant mammal.

In some implementations, uterine contraction measurement device 140 may also be on placed on the abdomen of the pregnant mammal. In other implementations, uterine contraction measurement device 140 may be embodied in the fetal hemoglobin device 115. In some cases, uterine contraction measurement device 140 may be a pressure sensor configured to detect the changes in pressure of the uterine muscle in units of pressure (mmHg and/or kPa).

In some embodiments, one or more light source(s) 105 and detector(s) 114 may act as an optoelectronic muscle contraction sensor without the need for a separate uterine contraction measurement device 140. In these embodiments, the light reflected from the pregnant mammal's uterus might change in nature when the uterus is in a relaxed state (more scattering) as opposed to a contracted state (less scattering). These changes in the rate of scattering of the light may be detected by one or more detector(s) 114 and processed by, for example, computer 150 to determine changes in the state of the uterine muscle. In some embodiments, one or more light source(s) 105 may direct light of a particular frequency/wavelength so that measurements of uterine contractions have a dedicated beam/frequency of light.

Preferably, the fetal hemoglobin probe 115 is placed at, or near, the bikini/supra-pubic region of the pregnant mammal 305. This area is typically right above the pubic hairline. This position is advantageous in the later stages of pregnancy, for example, after 9 months or 36 weeks of gestational development because the fetus's head will engage into the cervical birth canal and will, therefore, be in a fairly predictable location within the abdomen of the pregnant mammal. Additionally, when the head of the fetus is positioned within the cervical birth canal, the distance between pregnant mammal and fetus is minimal and therefore NIR light passing through the abdomen of the pregnant mammal is more likely to come into contact with the fetus and be reflected back to the fetal hemoglobin probe 115.

Figure 3A:
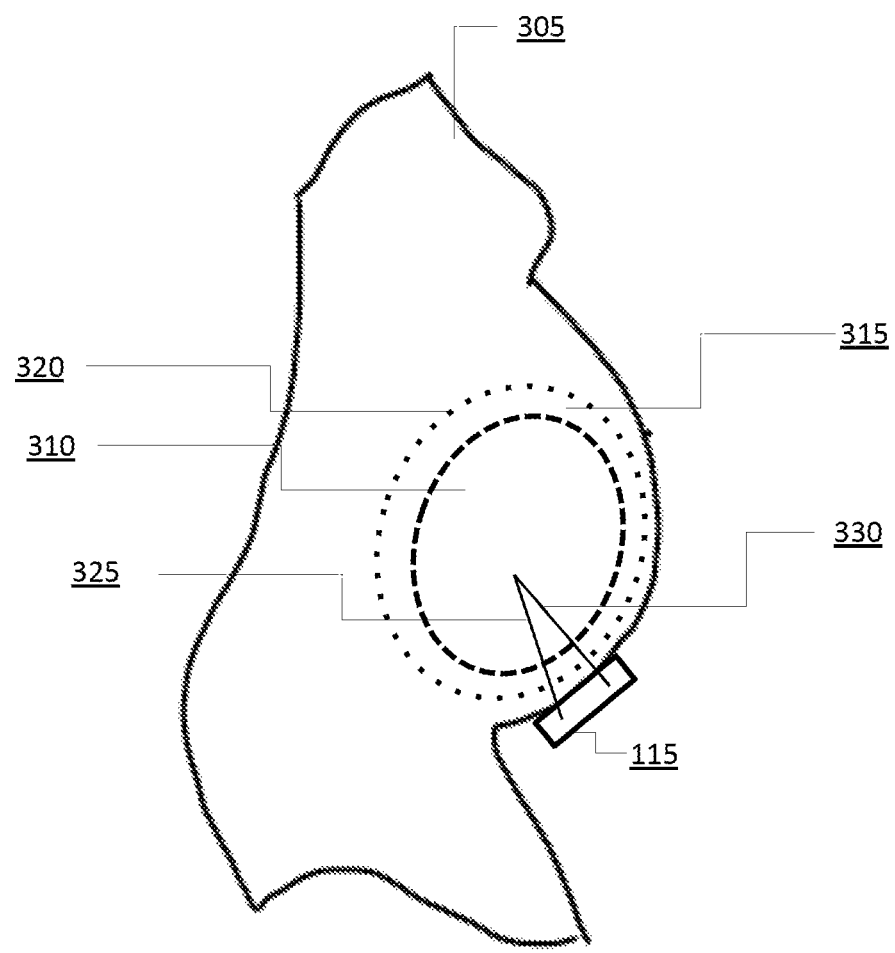
FIGS. 3A, 3B, 3C, and 3D provide illustrations of how light from a fetal hemoglobin probe may be directed into a pregnant mammal's abdomen, consistent with embodiments of the invention.
Figure 3B:
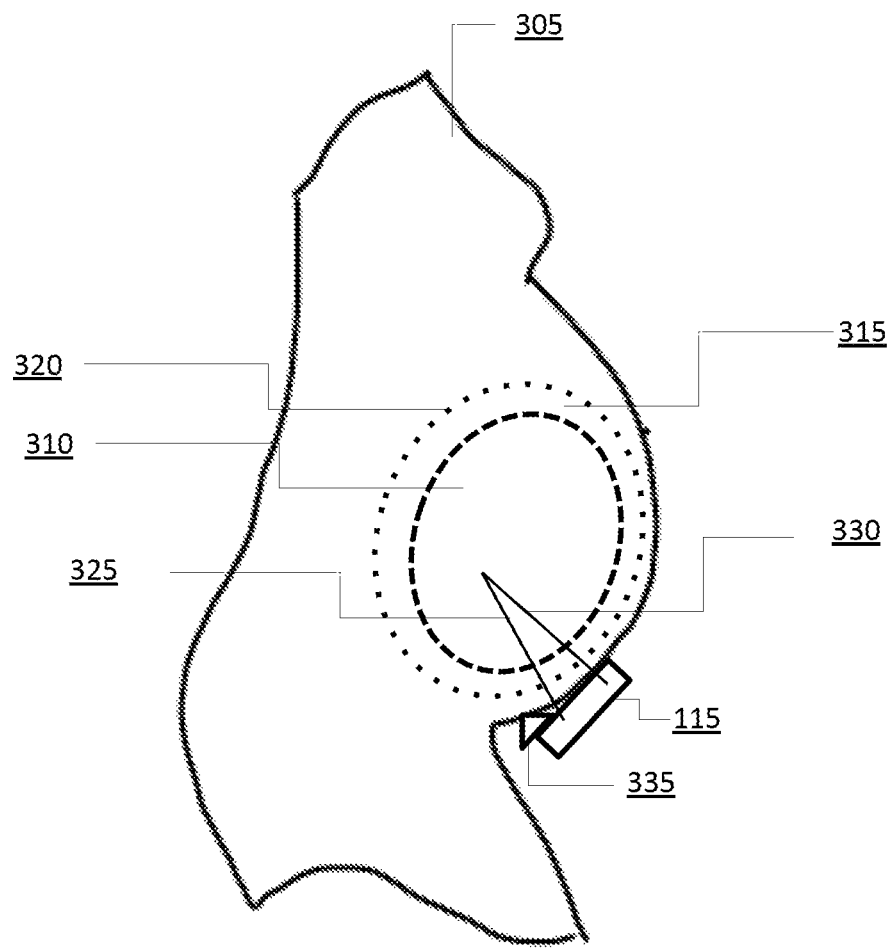
Figure 3C:
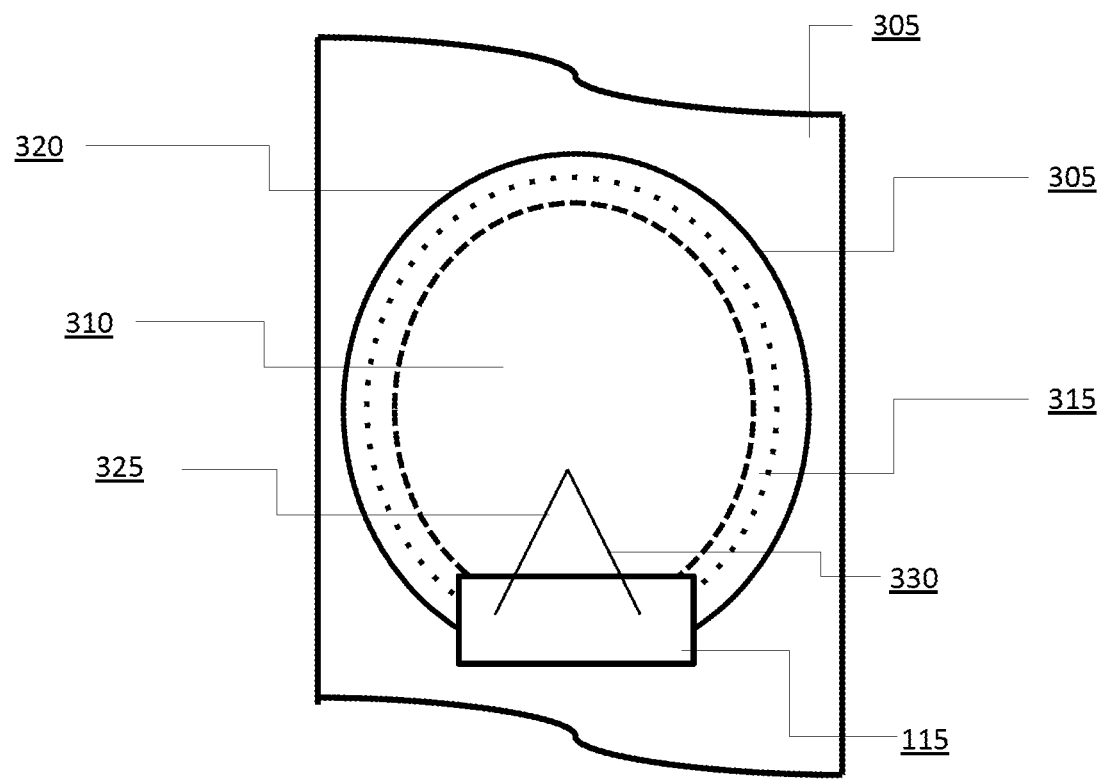

FIGS. 3A, 3B, and 3C provide illustrations of how light from fetal hemoglobin probe 115 may be directed into a pregnant mammal's 305 abdomen and reflected light may be detected by one or more detectors 114 of fetal hemoglobin probe 115. More specifically, FIG. 3A provides a cross sectional view of fetal hemoglobin probe 115 and of the pregnant mammal 305 as divided along a midline extending through the center of pregnant mammal 305 when she is viewed from the front (i.e., through the center of the face, between the breasts, etc.). FIG. 3A depicts an approximation of a fetus 310 that is surrounded by amniotic fluid and other tissue 315 present in a uterus 320 of the pregnant mammal 305. fetal hemoglobin probe 115 is show in FIG. 2C to be positioned on the lower abdomen of the pregnant mammal 305 at, or near, the bikini/supra-pubic region of the pregnant mammal 305.

As shown in FIG. 3A, a beam of light 325 (also referred to herein as an "incident beam") emitted from one or more light source(s) 105 is incident on pregnant mammal's 305 abdomen and is directed toward fetus 310. Beam of light 325 may be of any wavelength/frequency or combination of wavelengths/frequencies. In one embodiment, incident beam 325 may include light that is in the red spectrum and the near infrared spectrum.

In some embodiments, incident beam 325 may include two or more beams of light that may be emitted from, for example a single light source 105 (that emits two beams of light of the same frequency and/or a beam of light of two different frequencies) or two different light sources 105 (e.g., one frequency per light source). When two or more beams are included in incident beam 325, they may, on occasion be directed in slightly different directions so as to, for example, accommodate differences in the frequency of the light of the beam, a condition of the pregnant mammal 305 (e.g., skin pigmentation, body mass index, etc.) and/or a condition of the fetus (e.g., size, position, location within the uterus, skin pigmentation, etc.).

A portion of incident beam 325 may reflect from the fetus 310, amniotic fluid and other tissue 315, and uterus 320 as a reflected beam 330 and may be received by one or more detectors 114 provided by fetal hemoglobin probe 115. Although reflected beam 330 is shown as one beam, it may be any number of beams or individual photons. It is expected that not all of the light of incident beam 325 will be included in reflected beam 330 as some of the light of incident beam 325 may be lost/undetected due to, for example, scattering and/or absorption.

FIG. 3B provides an image of fetal hemoglobin probe 115 with an adjustment device 335 positioned between the skin of the pregnant mammal's 305 abdomen and a portion of fetal hemoglobin probe 115. In the embodiment of FIG. 3B, adjustment device 335 is triangular in shape and acts as a wedge to change an orientation/position of fetal hemoglobin probe 115 (and the corresponding orientation/position of light source(s) 105 and/or detector(s) 114) relative to the pregnant mammal's abdomen. In some cases, adjustment device 335 may change the angle of incidence for incident beam 325 and/or an orientation of one or more detectors 114. In some embodiments, adjustment device 335 may be transparent so as to allow for the passage of light into, and out of, the pregnant mammal's 305 abdomen. In other embodiments, adjustment device 335 may be semi-transparent or opaque so as to, for example, change a frequency of the incident beam 325 and/or reflected beam 330.

Adjustment device 335 may be configured to adjust for physiological conditions of the pregnant mammal's 305 abdomen that make it difficult to receive a reflected beam of sufficient strength. For example, for a pregnant mammal 305 with a high fat content around her abdomen, applying the fetal hemoglobin probe 115 directly to the pregnant mammal's 305 skin may not direct the incident beam 325 in the proper direction and/or enable detection of the reflected beam 330. Additionally, or alternatively, adjustment device 335 may be configured to adjust for physiological conditions of the fetus 310 including the size and/or placement of the fetus 310 within the uterus 320. For example, adjustment device 335 may be deployed so as to direct incident beam 325 toward the head of fetus 310.

In some embodiments, two or more adjustment mechanisms 335 may be used. An adjustment device 335 may be of any appropriate shape and/or configuration including, but not limited to, a triangle, circle, or rectangle and may be configured to adjust the positioning or operation of some, or all, of the components of fetal hemoglobin probe 115. In some instances, adjustment device 335 may be designed to improve the comfort of the pregnant mammal 305 while wearing fetal hemoglobin probe 115 and, to that end, may be configured to include soft and/or flexible material (e.g., foam) designed to adapt to a contour of the pregnant mammal's abdomen. In these instances, adjustment device 335 would be designed to engage with fetal hemoglobin probe 115 in a manner that does not obscure one or more components thereof.

In another embodiment, adjustment device 335 may include optics, filters, or other mechanical and/or electrical components configured to adjust one or more features of incident beam 325 and/or reflected beam 330. In some instances, one or more operations of adjustment device 335 may be performed upon receipt of instructions from, for example, a component of fetal hemoglobin probe 115 and/or computer 150.

FIG. 3C provides a front view of pregnant mammal's 305 abdomen with fetal hemoglobin probe 115 affixed thereto. The perspective is somewhat adjusted for FIG. 3C so that incident beam 325 and reflected beam 330 may be seen. In reality, both incident beam 325 and reflected beam 330 are directed into/reflected from the pregnant mammal's 305 abdomen along the −Z-axis.

Figure 3D:
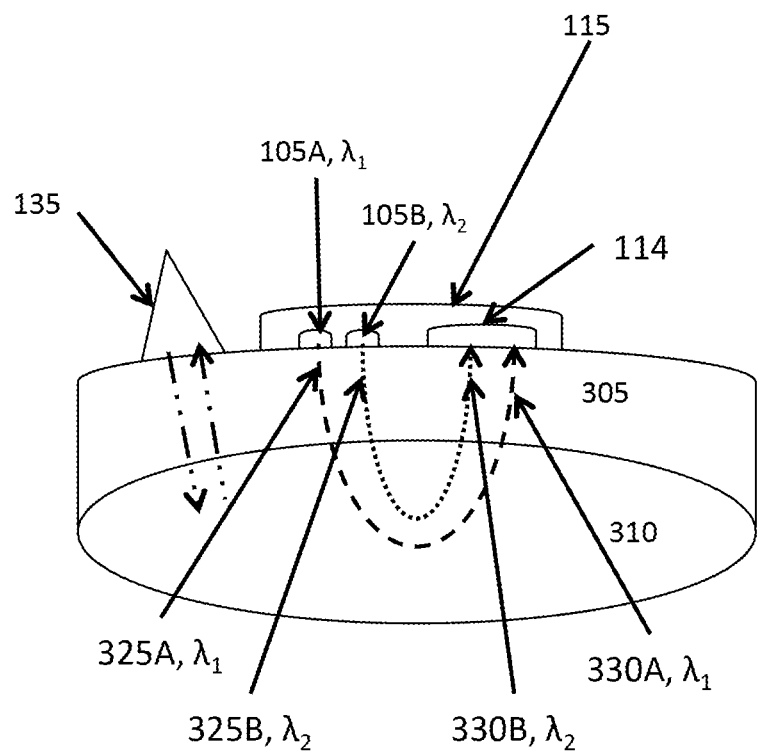

FIG. 3D provides a front cross section view of pregnant mammal's 305 abdomen with fetal hemoglobin probe 115 and Doppler/ultrasound probe 135 coincident therewith. As shown in FIG. 3D, Doppler/ultrasound probe 135 transmits a beam into pregnant mammal's 305 abdomen towards fetus 310 and receives a reflected signal. Doppler/ultrasound probe 135 is then uses this reflected signal to determine a fetal heart beat signal and/or determine a number of fetal heart beats per minute. and The fetal hemoglobin probe 115 of FIG. 3D has two light sources, a first of which, 105A, emits a light beam 325A of a first wavelength ($\lambda_1$) (noted on the figure as 105A, $\lambda_1$ and 325A, $\lambda_1$, respectively) and a second of which, 105B, emits a light beam 325B of a second wavelength ($\lambda_2$) (noted on the figure as 105B, $\lambda_2$ and 325B, $\lambda_2$, respectively). A portion of incident beams 325A and 325B is reflected by the pregnant mammal 305 and fetus 310 and received by detector 114 as reflected beam 330A and 330B, respectively ((noted on the figure as 330A, $\lambda_1$ and 330B, $\lambda_2$, respectively).

Figure 4A:
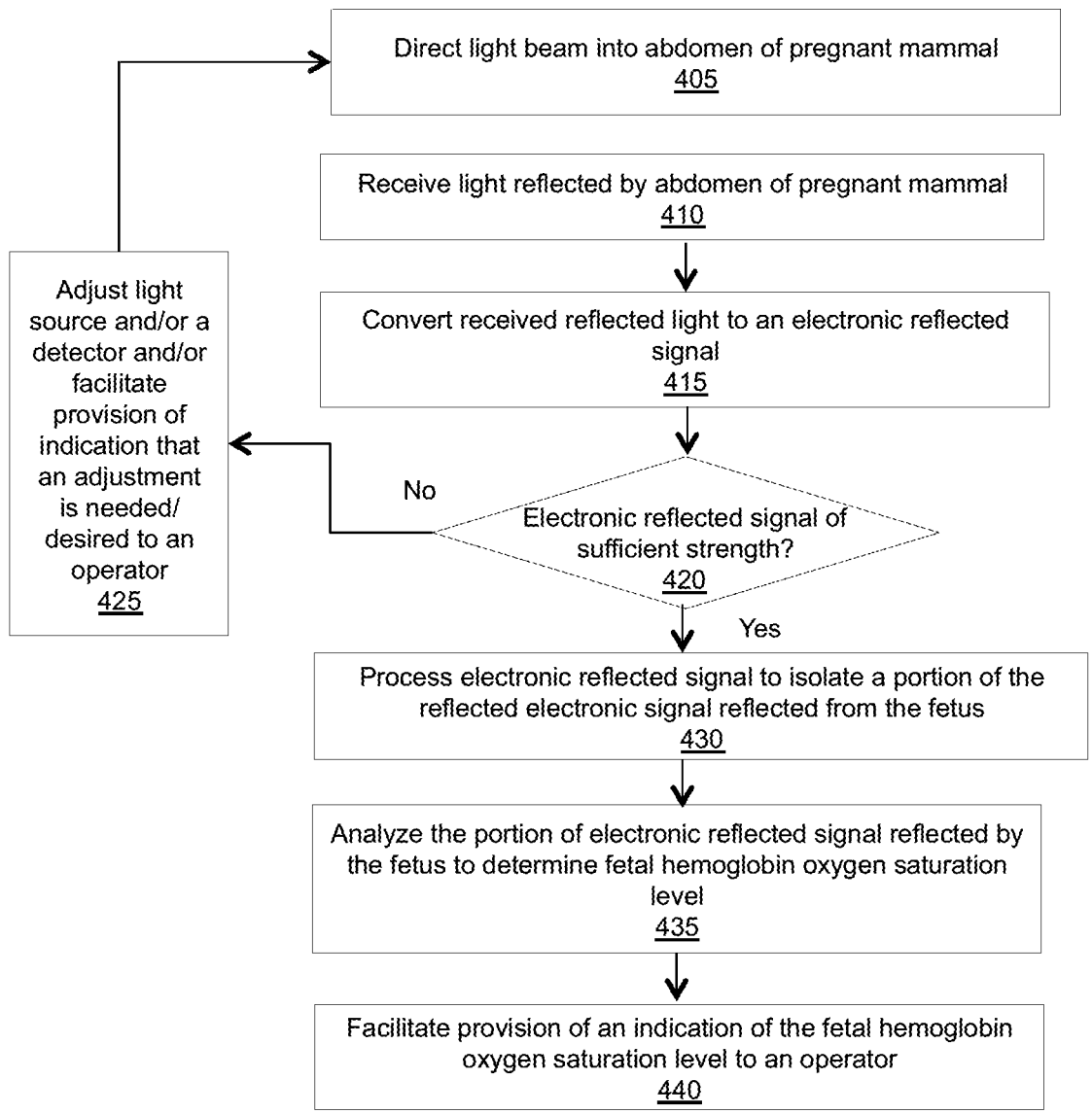
FIG. 4A is a flowchart illustrating a process for determining fetal hemoglobin saturation level, consistent with embodiments of the invention.

FIG. 4A illustrates an exemplary process 400 for performing fetal oximetry and/or fetal pulse oximetry trans-abdominally and/or in-utero to determine fetal hemoglobin oxygen saturation level. Process 400 may be performed by, for example, system 100 and/or a component thereof.

Initially, a light beam, such as incident beam 325, is directed into the abdomen of a pregnant mammal, such as pregnant mammal 305 (step 405) by, for example, one or more light sources such as light source(s) 105 provided by one or more of the fetal hemoglobin mammal' pregnant mammal's abdomen may be directed toward the pregnant mammal's fetus, such as fetus 310 as shown in FIGS. 3A and 3B discussed above.

The light beam directed into the pregnant mammal's abdomen may include any number of light beams and/or frequencies/wavelengths of light as described above with regard to incident beam 325. In some instances, the light beam of step 405 may be a plurality of light beams emitted from a plurality of light sources positioned at a plurality of different locations along the abdomen of the pregnant mammal as shown in, for example, FIGS. 2D and 2E. Additionally, or alternatively, the light beam of step 405 may include a plurality of wavelengths/frequencies emitted by a single of light source that may, for example, include multiple LEDs.

In some embodiments, the light beam of step 405 may include light of first and second wavelengths with a first of the wavelength being in the red portion of the electromagnetic spectrum (i.e., 620-750 nm) and a second of wavelengths in the near-infrared (NIR) portion of the electromagnetic spectrum (e.g., 750 nm-2,500 nm). Use of these wavelengths is preferred, but not required, because light of wavelengths in the red and near-infrared spectrum are known to travel through, and/or be reflected by, skin and body tissue. In some embodiments, light of, for example, a third, fourth, fifth, or more different wavelengths may be directed toward the abdomen of the pregnant mammal. In some circumstances, use of more than two wavelengths of light may be useful to enhance reflected signal strength and/or clarity in various circumstances including, but not limited to, distance of the fetus from the external skin, or uterine wall, of the pregnant mammal (i.e., depth of the fetus), level of melanin/pigment in the skin of the pregnant mammal and/or fetus, strength of fetal pulse signal, how much the fetus moves within the placenta and/or uterus of the pregnant mammal, and so on.

In some embodiments, an intensity of the light directed into the pregnant mammal at step 405 may be varied and/or different for different wavelengths of light. For example, the intensity of red light directed into the pregnant mammal's abdomen may be greater than the intensity of the near-infrared light due to the transmission/reflection properties of red light verses near infrared light (i.e., near-infrared light is known to reflect more light when shown into body tissue than red light). However, it is expected that an intensity of the light beam of step 405 will be safe for both the pregnant mammal and her fetus (e.g., not cause burns to the pregnant mammal's skin and/or damage to fetal tissue (e.g., eyes)).

In step 410, light (e.g., waves and/or photons) reflected by the abdomen of the pregnant mammal (and the fetus) may be received by one or more detectors (e.g., photo-sensor, photo detectors or photodiodes), such as detector 115 and/or transceiver 107 and converted (step 415) into an electronic signal that represents the reflected light (this signal may be referred to herein as a "reflected electronic signal" by the photo-sensor/photodiode/photo detector. In some instances, the light directed into the abdomen of the pregnant mammal, may travel a distance of, for example, 3-5 cm to contact the fetus and another 3-5 cm once reflected from the fetus to be detected by the detector. Thus, the total travel distance for the incident and reflected beam may be as high as 8 or 10 cm. When traveling this distance, a substantial amount of scattering and other interference in the detection of a reflected signal may occur and it is possible that only a small fraction (e.g., 0.5-5%) of the light incident on the abdomen of the pregnant mammal will be reflected by the fetus and received by detector.

Optionally, in step 420, it may be determined whether the electronic reflected signal is of sufficient strength to detect, for example, the pulse and/or fetal oxygen saturation of the fetus. Exemplary signal strengths that are sufficient are in the range of 30-500 dB with a signal-to-noise (SNR) ratio of 1-8, with a preferred SNR of approximately 3-4.5.

When the signal isn't of sufficient strength, the light source(s) and/or detector(s) may be adjusted automatically (i.e., without operator intervention) and/or provision of an indication that an adjustment of the light source(s) and/or detector(s) may be desired or needed to an operator (e.g., doctor or nurse) may be facilitated (step 425). Exemplary indications provided in step 425 include, but are not limited to, an alarm, a message (e.g., written or audio), and a recommendation. Exemplary automatic adjustments include, but are not limited to, adjusting a lens positioned between the pregnant mammal's abdomen and the light source(s) and/or detector(s) so as to focus the light emitted by the light source(s) and/or received by the detector(s), adjusting an amount of power delivered to the light source(s) and/or detector(s), adjusting an intensity and/or frequency of the light emitted by one or more of the light source(s) and so on. In some embodiments, activation of additional light sources to direct light into the pregnant mammal's abdomen may be responsive to a determination that the electronic reflected signal is not of sufficient strength.

In some instances, the adjustment(s) of step 425 may be performed and/or facilitated by one or more adjustment mechanisms, such as adjustment mechanisms 122 and/or controllers, such as controller 112. Once adjusted, the light beam may again be directed into the pregnant mammal's abdomen (i.e., step 405 may be repeated) and steps 410-420 may be repeated. When the electronic reflected signal is of sufficient strength, or when steps 420 and 425 are not performed, process 400 may advance to step 430.

In step 430, the electronic reflected signal may be processed to isolate a portion of the reflected electronic signal reflected from the fetus (as opposed to the pregnant mammal or noise). For ease of discussion, the portion of the reflected electronic signal reflected from the fetus may be referred to herein as the fetal reflected electronic signal. Examples of how step 430 may be executed are discussed below with regard FIGS. 5A-5D. Following step 430, the fetal reflected electronic signal may be analyzed to determine the oxygen saturation level of hemoglobin contained in the fetus' blood via, for example, oximetry and/or pulse oximetry techniques (step 440). Typical values for the oxygen saturation of fetal blood fall within the range of 30-70%. An exemplary method of determining fetal hemoglobin saturation level uses a version of the Beer-Lambert law modified to account for the scattering effect of the reflected light as it is scattered by tissues in the body as described by Zourabian, Anna, et al., *Trans-abdominal Monitoring of Fetal Arterial Blood Oxygenation Using Pulse Oximetry*, Journal of Biomedical Optics, 5(4), pp. 391-405 (October 2000), which is incorporated by reference herein. Further details regarding execution of step 435 is provided below with regard to FIGS. 6A-6H.

Then, in step 440, provision of an indication of fetal oxygen level to an operator may be facilitated. Exemplary operators include, but are not limited to, doctors, nurses, and other caregivers. Exemplary indicators include a waveform shown on a display device (e.g., computer monitor), a numerical value provided via a display device and/or message (e.g., SMS text message), such as a fetal hemoglobin oxygen saturation level. Facilitating provision of the indication of step 465 may include providing the indication to a computer, such as computer 150 and/or a display device such as display device 155. An example of such a display of fetal hemoglobin oxygen saturation level is provided by FIGS. 8A and 8B and is discussed below.

Figure 5A:
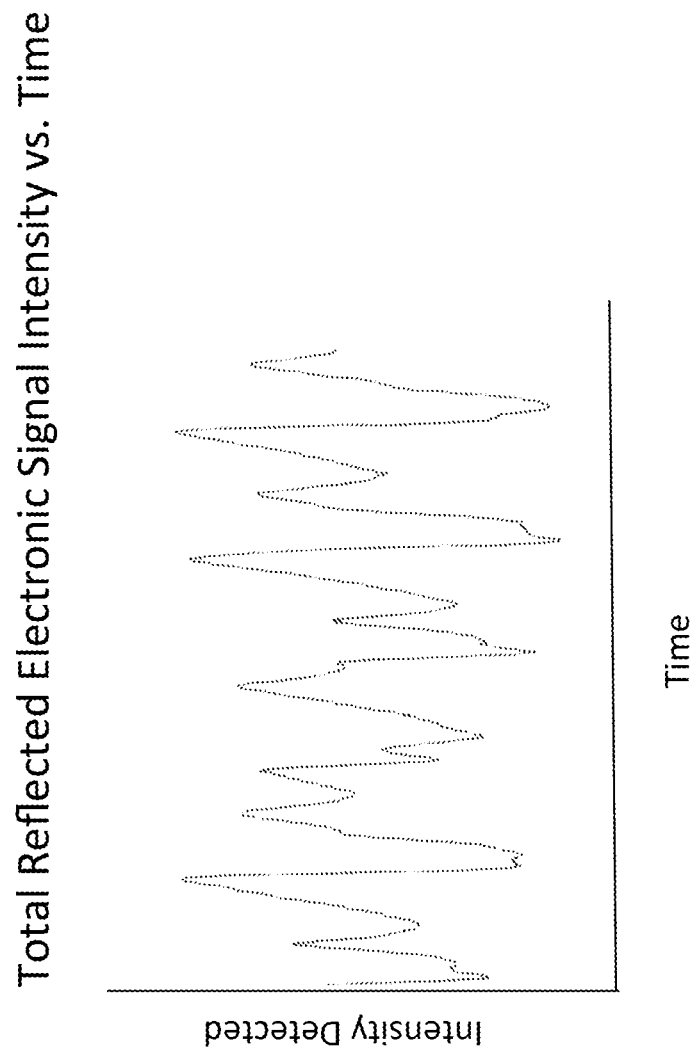
FIG. 5A provides a graph of total reflected electronic signal intensity vs. time, consistent with an embodiment of the invention.
Figure 5B:
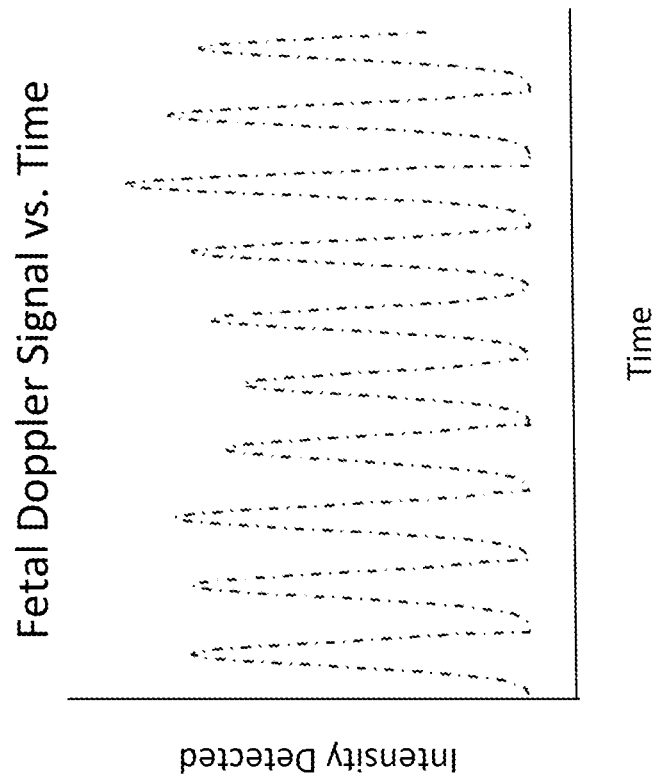
FIG. 5B provides a graph of a fetal Doppler signal vs. time, consistent with an embodiment of the invention.
Figure 5C:
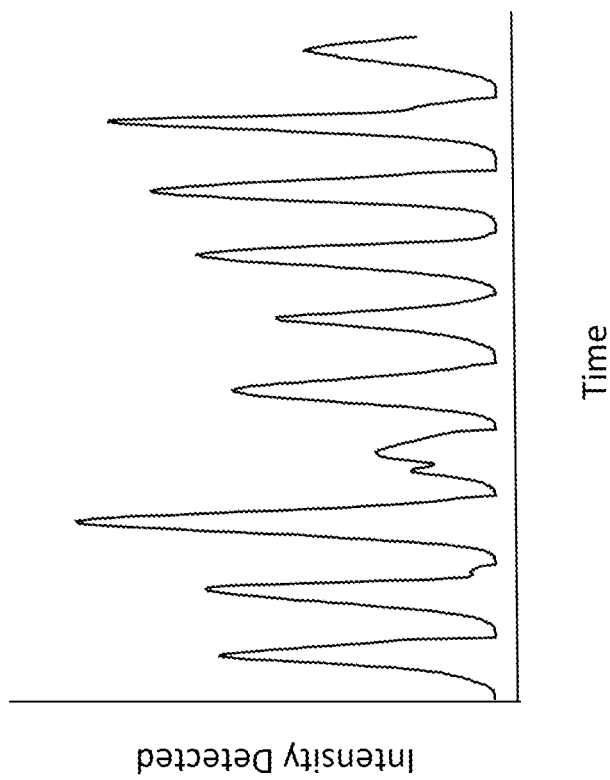
FIG. 5C provides a graph that shows the product of multiplying the total reflected electronic signal intensity and the Doppler signal together while synchronizing over time, consistent with an embodiment of the invention.

One method of processing the signal to isolate the portion of the reflected electronic signal reflected from the fetus from the total reflected electronic signal is to multiply the total reflected electronic signal by signal that provides the fetal heart (i.e., perform step 430) beat as may be provided by, for example, a Doppler and/or ultrasound probe such as Doppler/ultrasound probe 135. The resultant signal (i.e., the signal that is the product of multiplying the total reflected electronic signal and the fetal heartbeat signal) may approximate the portion of the total reflected electronic signal reflected by the fetus. To improve this approximation, the signal reading may be averaged over a number of cycles to provide a more accurate approximation of the portion of the total reflected electronic signal reflected by the fetus. An example of this process is provided by FIGS. 5A-5D, of which FIG. 5A provides a graph 500 of total reflected electronic signal intensity vs. time and represents light reflected by the abdomen of the pregnant mammal detected in step 410. FIG. 5B provides a graph 501 of a Doppler signal vs. time. This signal and represents light reflected by the abdomen of the pregnant mammal detected in step 410. The Doppler signal represents the fetus' heartbeat. This signal may be received from, for example, Doppler/ultrasound probe 135. FIG. 5C provides a graph 502 that shows the product of multiplying the total reflected electronic signal intensity (from FIG. 2A) and the Doppler signal (from FIG. 2B) together while synchronizing over time so that a signal intensity of the total reflected electronic signal at a particular moment in time is multiplied by the Doppler signal intensity at that same particular moment in time. The resultant signal shown in FIG. 5C approximates the portion of the total reflected electronic signal reflected from the fetus. This signal may then be analyzed to determine fetal oxygen saturation levels using, for example, oximetry or pulse oximetry techniques.

Figure 5D:
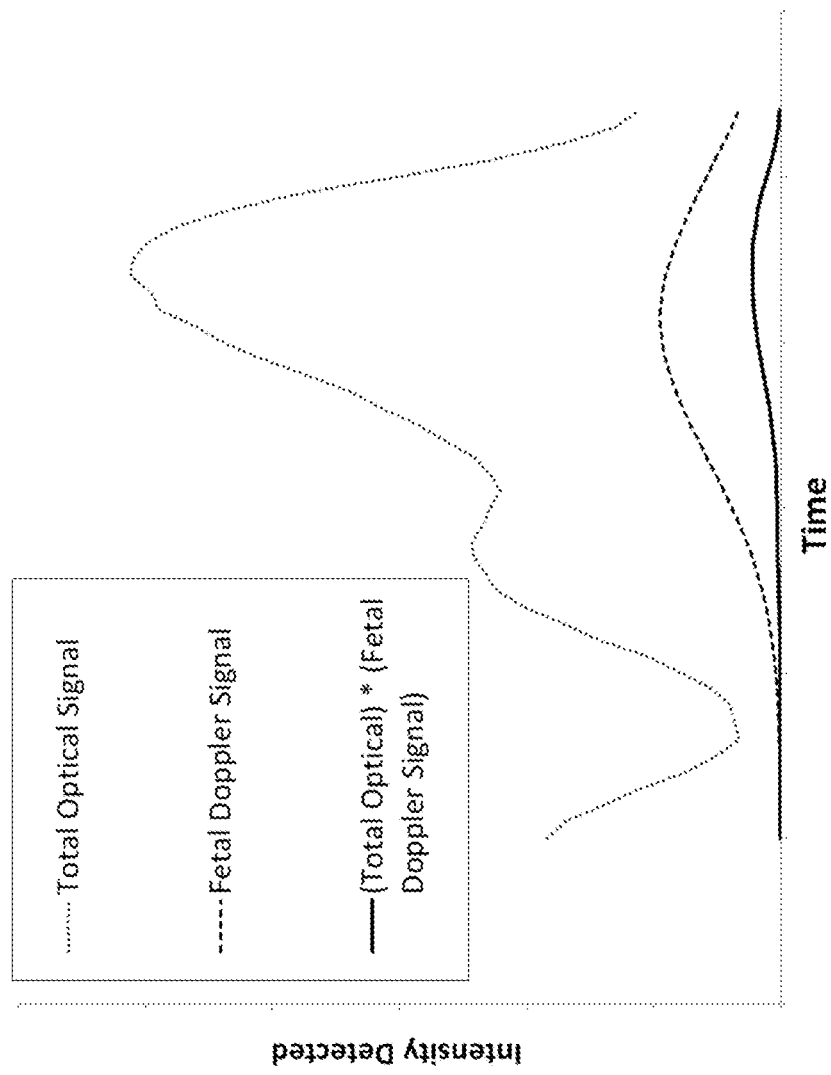
FIG. 5D, provides a graph of the total reflected electronic signal intensity, the fetal heartbeat/Doppler signal and the result of multiplying total reflected electronic signal intensity and Doppler signal synchronized over time, consistent with an embodiment of the invention.

In some embodiments, the accuracy of the approximated portion of the total reflected electronic signal reflected from the fetus may be improved by averaging a number of signal intensities over a period of time (e.g., a number of periods) as shown in FIG. 5D, which provides a graph 503 of the total reflected electronic signal intensity, the fetal heartbeat/Doppler signal and the result of multiplying total reflected electronic signal intensity and Doppler signal synchronized over time (referred to on graph 503 as "fetal reflected signal."

Figure 4B:
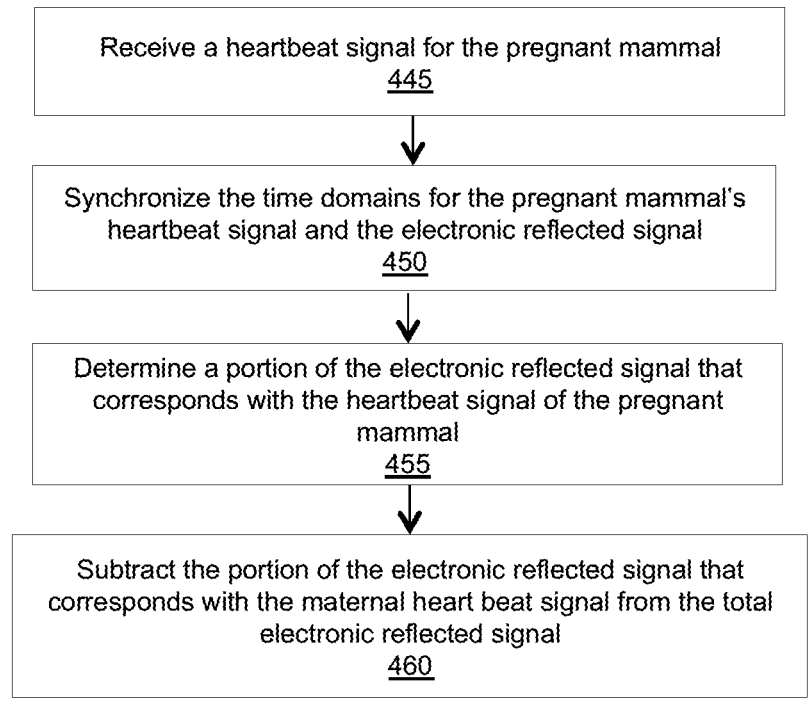
FIGS. 4B and 4C are flowcharts illustrating processes for processing the reflected electronic signal to isolate the portion of the reflected electronic signal reflected from the fetus, consistent with embodiments of the invention.

Another method of processing the electronic reflected signal to isolate the portion of the reflected electronic signal reflected from the fetus from the total reflected electronic signal is to multiply the total reflected electronic signal by signal that provides the fetal heart (i.e., perform step 430) is provided by FIG. 4B, which shows sub-process 401.

In step 445 of sub-process 401, a heartbeat signal for the pregnant mammal is received from, for example, a pulse oximetry probe like pulse oximetry probe 130 and/or an adult hemoglobin probe like NIRS adult hemoglobin probe 125. Next, the received pregnant mammal's heartbeat signal may be synchronized in the time domain with the electronic reflected signal (step 450). Then a correlation between the pregnant mammal's heartbeat and changes in the electronic reflected signal may be established so as to determine a portion of the electronic reflected signal that is reflected by the pregnant mammal (step 455). In step 460, the portion of the portion of the electronic reflected signal that is reflected by the pregnant mammal is then subtracted from the electronic reflected signal with the portion of the electronic reflected signal reflected by the fetus being thereby isolated.

Figure 4C:
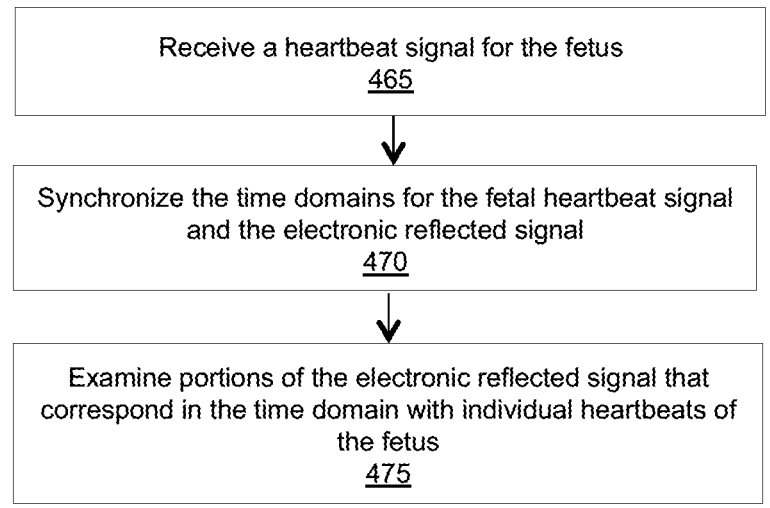

Another method of processing the signal to isolate the portion of the reflected electronic signal reflected from the fetus from the total reflected electronic signal is to multiply the total reflected electronic signal by signal that provides the fetal heart (i.e., perform step 430) is provided by FIG. 4C, which shows sub-process 402.

In step 465 of sub-process 402, a heartbeat signal for the fetus may be received from, for example, an ultrasound device and/or a Doppler device, such as Doppler/ultrasound probe 135. Next, the received fetus' heartbeat signal may be synchronized in the time domain with the electronic reflected signal (step 470). Then, portions of the electronic reflected signal that correspond in the time domain with the individual heartbeats may be examined (step 475). In this way, the entire electronic reflected signal does not have to be processed/analyzed; only the portions of the electronic reflected signal where a fetal heartbeat, or pulse, occur are examined. This saves processing time and resources because the entire signal does not have to be processed.

In some embodiments, the processing of step 430 and/or analysis of step 435 may include processing the reflected electronic signal in order to ascertain a signal that corresponds to the absorption/reflection of NIR light by oxygenated hemoglobin and deoxygenated hemoglobin of the fetus. Using this information, a level (or percentage) of fetal hemoglobin oxygen saturation (step 435) may be determined.

Because fetal hemoglobin is structurally different from adult hemoglobin it absorbs light differently and the signal reflected from the fetal hemoglobin at various wavelengths will be of a different magnitude when compared to the magnitude of the signal at those same wavelengths reflected by the pregnant woman. In this way, measuring a quantity of light reflected from the hemoglobin of the pregnant woman and fetus at various wavelengths will provide an indication of the amount of light of a particular wavelength that is absorbed by the fetal hemoglobin as well as the pregnant woman's hemoglobin. Looking at the ratios of light reflected at various wavelengths will provide a benchmark that correlates to a specific fetal blood oxygen level. In some instances, the variations in wavelength absorption of the fetal hemoglobin when compared to the pregnant woman's hemoglobin may not be sufficient to provide an adequately strong or clear signal indicating fetal hemoglobin oxygen saturation levels for clinical and/or diagnostic purposes. Therefore, one or more signal processing techniques may be applied to the signal received by the fetal hemoglobin probe 115 to determine fetal hemoglobin oxygen saturation as will be discussed in detail below.

In an exemplary signal processing technique, a signal received from the pregnant woman's pulse oximetry probe (e.g., pulse oximetry probe 130) may be used to determine the oxygen saturation level of the pregnant woman's arterial blood, which corresponds to an oxygenated state of pregnant woman's hemoglobin. The pulse oximetry probe is used to make this determination because the depth of a human finger is 1-2 cm, a measurable amount of light can pass through the fingertip and there is no interference from fetal blood flow or circulating fetal hemoglobin at the pregnant woman's fingertip position. Hence, a reading from pulse oximetry probe 130 will directly correspond to how much light is absorbed and/or reflected at various wavelengths by the pregnant woman's adult hemoglobin. This information may be used to understand how the light is interacting with pregnant woman's hemoglobin near the fetus and this information may be subtracted from the signal received by the fetal hemoglobin probe 115 to determine how much light is absorbed and/or reflected at various wavelengths by the fetus' hemoglobin.

Additionally, or alternatively, the signal received by the fetal hemoglobin probe 115 may be processed using a heart rate of the fetus and/or pregnant woman. The timing of the pregnant woman's heartbeat correlates to the timing for various levels of blood oxygen saturation for the pregnant woman. This correlation may be used to detect a signal corresponding the level of blood oxygen saturation for the pregnant woman within the signal received by the fetal hemoglobin probe 115. The fetal oxygen saturation level may then be determined by subtracting, or otherwise filtering, the detected signal corresponding the level of blood oxygen saturation for the pregnant woman from signal received by the fetal hemoglobin probe 115.

Additionally, or alternatively, the fetal heartbeat correlates to the timing for various levels of blood oxygen saturation for the fetus. This correlation may then be used to detect a signal corresponding the level of blood oxygen saturation for the fetus within the signal received by the fetal hemoglobin probe 115. For example, Doppler/ultrasound probe 135 and/or an ultrasound device may indicate that the fetus' heart rate is in the range of 120-160 beats per minute and this fetal heart rate may be used to gate and/or correlate a NIR signal from the fetus.

In the rare circumstance when the fetal heart rate and maternal heart rate are similar (fetal bradycardia and maternal tachycardia) the two heartbeats may be distinguished from one another using the known fact that there is a slight pause in the heart rate during respiration. So, by monitoring the heart rate signal (via, e.g., pulse oximetry probe 130), one may observe that the pregnant woman's the heart rate slows down for a moment when she takes in a deep breath. This slowing will only be present in the signal providing the pregnant woman's heart rate because fetuses do not breathe while in utero. In this way, the two heart rates may be distinguished from one another.

In some embodiments, a signal from NIRS adult hemoglobin probe 125 may be processed to determine a ratio of adult oxyhemoglobin to adult de-oxyhemoglobin. This ratio may then be used to subtract readings from the pregnant woman's blood flow so that a signal from the fetus's blood flow may be isolated and analyzed to, for example, determine a level of fetal hemoglobin oxygen saturation.

In other embodiments, processing the signals received by the fetal hemoglobin probe 115 may include oscillating between time domain and frequency domain analysis. This oscillation may allow identification signals that have a cyclical (periodic) component as opposed to signals that are random or non-periodic (acyclic/aperiodic). Random or non-periodic signals are more likely to be noise and examining the received signal for random or non-periodic signals will assist in determining a noise level of the signal as well as portions of the signal that may be filtered or otherwise removed therefrom.

In some embodiments, process 400 may include the establishment of a set of correlations between the intensity of light reflected/absorbed at certain wavelengths by fetal oxyhemoglobin and de-oxyhemoglobin and the oxygen saturation levels of the fetal oxyhemoglobin and de-oxyhemoglobin. This set of correlations may be performed prior to executing process 400 for a particular pregnant mammal during the fetal labor and delivery process and may be stored in, for example, computer 150. An exemplary correlation may be a reflection of light of wavelength A with an intensity X and a reflection of light of wavelength B with an intensity 0.8X to an fetal oxygen saturation level of 50% of fetal hemoglobin being bound to oxygen. Another exemplary correlation may be a reflection of light of wavelength A with an intensity X and a reflection of light of wavelength B with an intensity 0.5X to an fetal oxygen saturation level of 25% of fetal hemoglobin being bound to oxygen.

Figure 6A:
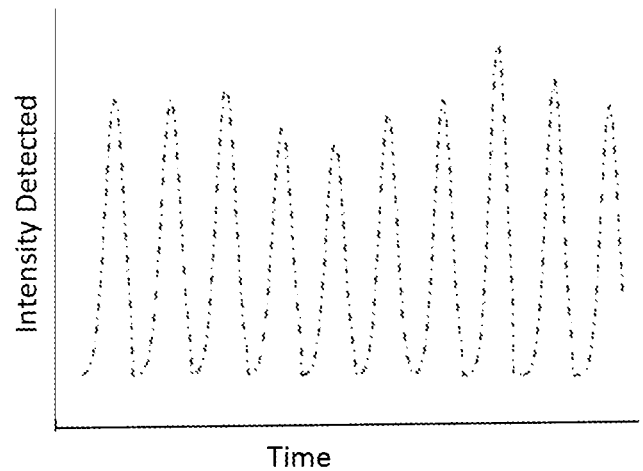
FIG. 6A provides a graph of a fetal Doppler signal vs. time, consistent with an embodiment of the invention.

(noted on the figure as 105A, $\lambda_1$ and 325A, $\lambda_1$, respectively) and a second of which, 105B, emits a light beam 325B of a second wavelength ($\lambda_2$) (noted on the figure as 105B, $\lambda_2$ and 325B, $\lambda_2$, respectively). A portion of incident beams 325A and 325B is reflected by the pregnant mammal 305 and fetus 310 and received by detector 114 as reflected beam 330A and 330B, respectively ((noted on the figure as 330A, $\lambda_1$ and 330B, $\lambda_2$, FIGS. 6A-6H provide information in the form of graphs regarding an example of how reflected electronic signal is analyzed to determine fetal hemoglobin oxygen saturation level. At times, fetal hemoglobin oxygen saturation level may also be referred to herein as fetal arterial oxygen saturation level, which may be abbreviated to (% SaO2). More specifically, FIG. 6A provides a graph 601 of a Doppler signal vs. time. The Doppler signal corresponds to a fetal heart beat signal. The Doppler signal of FIG. 6A is similar to the Doppler signal of FIG. 5B.

Figure 6B:
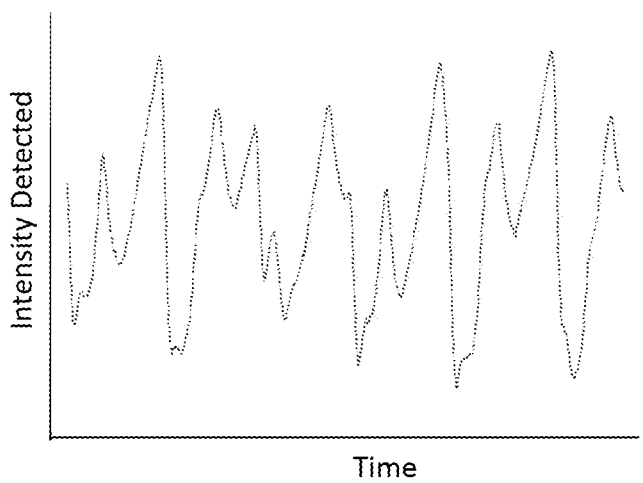
FIG. 6B provides a graph of reflected electronic signal intensity for $\lambda_1$ vs. time, consistent with an embodiment of the invention.
Figure 6C:
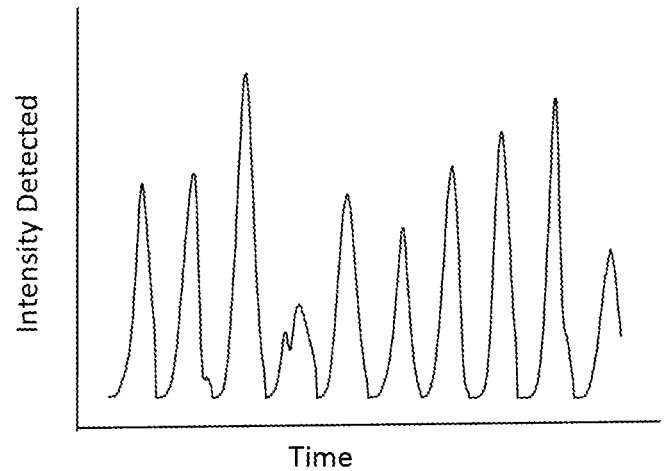
FIG. 6C provides a graph that shows the product of multiplying the total reflected electronic signal intensity for $\lambda_1$ and the fetal Doppler signal together while synchronizing over time, consistent with an embodiment of the invention.

FIG. 6B provides a graph 602 of reflected electronic signal intensity for $\lambda_1$ vs. time. This graph may correspond to reflected signal 330A, $\lambda_1$. Any of the processes discussed above may be used to isolate the portion of the signal reflected by the fetus from the reflected electronic signal intensity for $\lambda_1$. In the example provided, the total reflected electronic signal intensity for $\lambda_1$ and the fetal Doppler signal are multiplied together while synchronizing over time to provide the product of multiplying the total reflected electronic signal intensity for $\lambda_1$ and the Doppler signal together while synchronizing over time as shown in graph 603 of FIG. 6C.

Figure 6D:
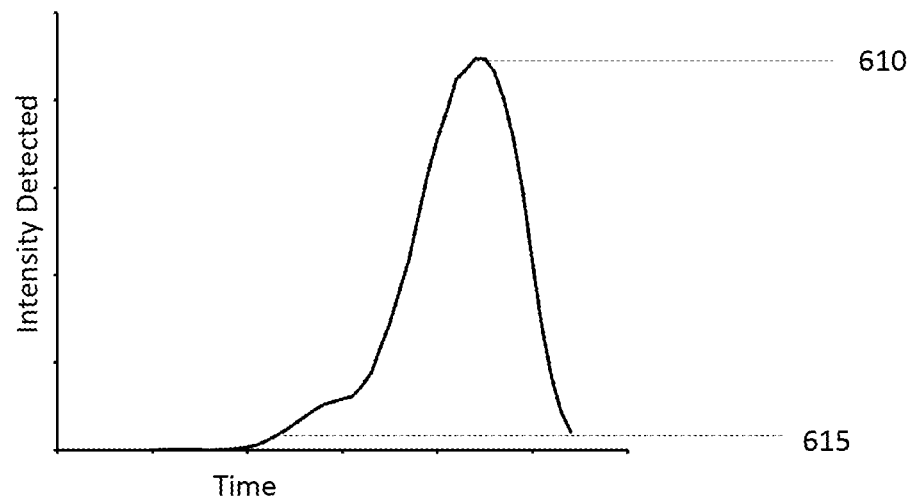
FIG. 6D, provides a graph that shows the product of multiplying the total reflected electronic signal intensity for $\lambda_1$ and the fetal Doppler signal together while synchronizing over time averaged over several periods, consistent with an embodiment of the invention.

FIG. 6D provides a graph 604 that shows the product of multiplying the total reflected electronic signal intensity for $\lambda_1$ and the fetal Doppler signal together while synchronizing over time averaged over several periods. This graph (or the data used to generate the graph) is analyzed to determine an intensity of a systolic value for the first wavelength $\lambda_1$ 610, which corresponds to the peak of the curve (i.e., highest value) and an intensity of a diastolic value for the first wavelength $\lambda_1$ 615, which corresponds to the trough of the curve (i.e., lowest/smallest value).

Figure 6E:
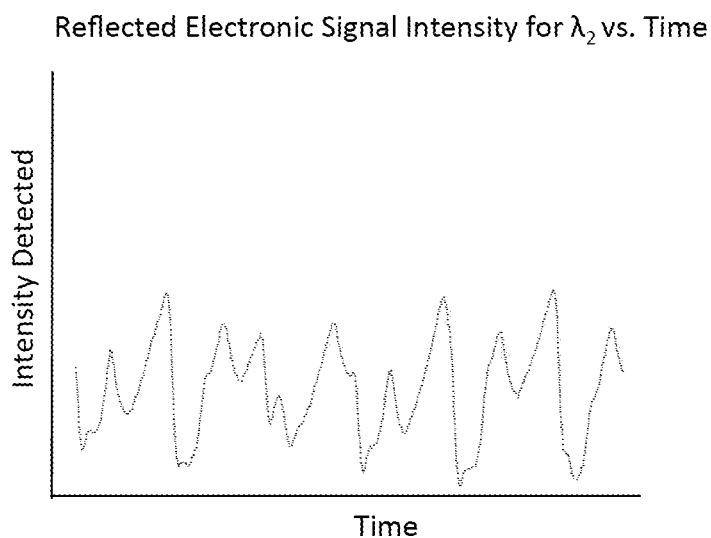
FIG. 6E provides a graph of reflected electronic signal intensity for $\lambda_2$ vs. time, consistent with an embodiment of the invention.
Figure 6F:
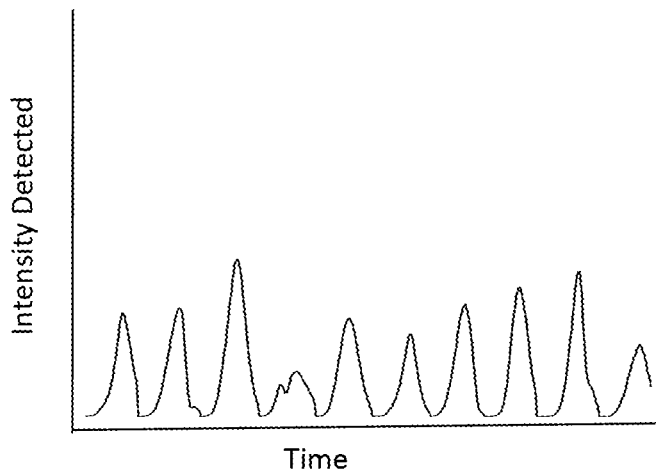
FIG. 6F provides a graph that shows the product of multiplying the total reflected electronic signal intensity for $\lambda_2$ and the fetal Doppler signal together while synchronizing over time, consistent with an embodiment of the invention.

FIG. 6E provides a graph 605 of reflected electronic signal intensity for $\lambda_2$ vs. time. Any of the processes discussed above may be used to isolate the portion of the signal reflected by the fetus from the reflected electronic signal intensity for $\lambda_2$. In the example provided, the total reflected electronic signal intensity for $\lambda_2$ and the fetal Doppler signal are multiplied together while synchronizing over time to provide the product of multiplying the total reflected electronic signal intensity for $\lambda_2$ and the Doppler signal together while synchronizing over time as shown in graph 606 of FIG. 6F.

Figure 6G:
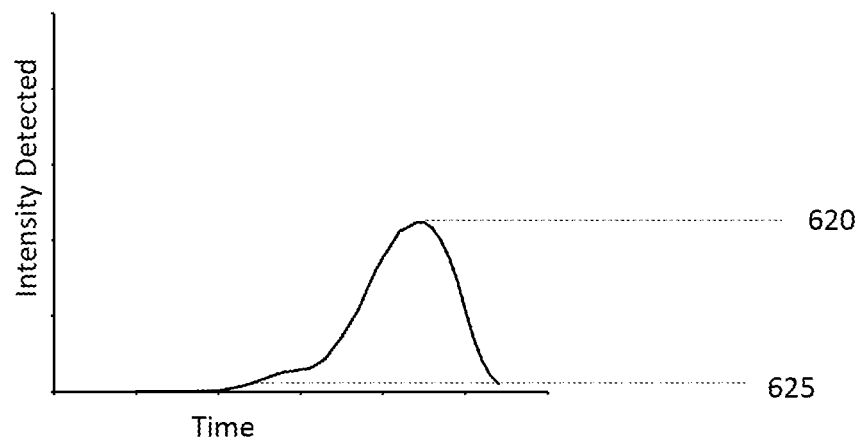
FIG. 6G, provides a graph that shows the product of multiplying the total reflected electronic signal intensity for $\lambda_2$ and the fetal Doppler signal together while synchronizing over time averaged over several periods, consistent with an embodiment of the invention.

FIG. 6G provides a graph 607 that shows the product of multiplying the total reflected electronic signal intensity for $\lambda_2$ and the fetal Doppler signal together while synchronizing over time averaged over several periods. This graph (or the data used to generate the graph) is analyzed to determine an intensity of a systolic value for the second wavelength $\lambda_2$ 620, which corresponds to the peak of the curve (i.e., highest value) and an intensity of a diastolic value for the second wavelength $\lambda_2$ 625, which corresponds to the trough of the curve (i.e., lowest/smallest value).

A modulation ratio (R) between the reflected intensity of two wavelengths of light may be calculated as follows:

$$R = \log\left(\frac{T_{sys\lambda1}}{T_{dias\lambda1}}\right) \bigg/ \log\left(\frac{T_{sys\lambda2}}{T_{dias\lambda2}}\right) \qquad \text{Equation 1}$$

where:

$T_{sys\lambda 1}$ is the intensity of the systolic value for the first wavelength ($\lambda_1$);

$T_{dias\lambda 1}$ is the intensity of the diastolic value for the first wavelength ($\lambda_1$);

$T_{sys\lambda 2}$ is the intensity of the systolic value for the second wavelength ($\lambda_2$); and $T_{dias\lambda 2}$ is the intensity of the diastolic value for the second wavelength ($\lambda_2$).

Figure 6H:
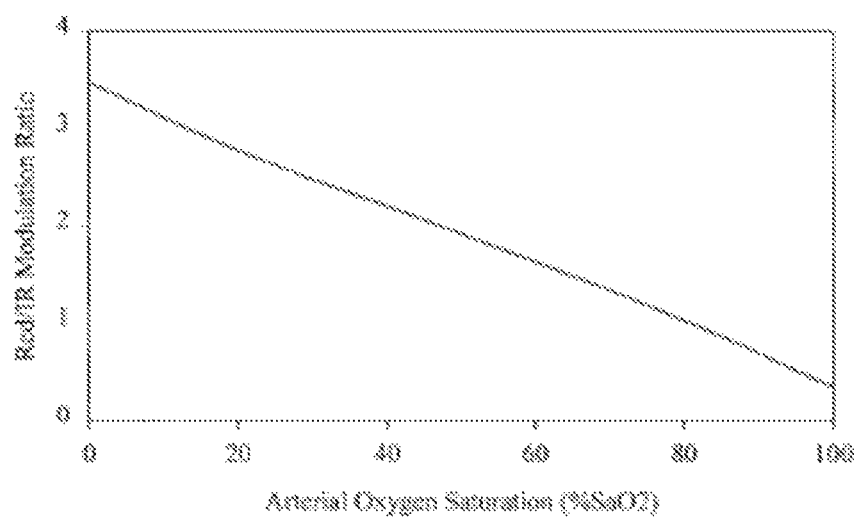
FIG. 6H provides a graph that shows a relationship between a red/IR wavelength modulation ration and arterial oxygen saturation (% SaO2)

The modulation ratio, R, may then be used to determine a level of arterial oxygen saturation value (% SaO2) in one of at least two fashions. When a relationship between a modulation ratio, R, for a pair of wavelengths (i.e., $\lambda_1$ and $\lambda_2$) and arterial oxygen saturation is known (from, for example, experimentally determined values), then the value of R may be used to look up a corresponding arterial oxygen saturation level. FIG. 6H provides an exemplary graph that plots a known relationship between values for R (when $\lambda_1$ is in the red spectrum and $\lambda_2$ is in the infrared spectrum) with arterial oxygen saturation values.

[1] Source of FIG. 6H: Paul D. et al., *Wavelength Selection for Low-Saturation Pulse Oximetry*, IEEE Transactions on Biomedical Engineering, Vol. 44, No. 3, March 1997, p. 149.

Following through with the above example (with the appropriate reference numbers for intensity values inserted from graphs 604 and 607), would yield the following calculation for equation 1:

$$R = \log\left(\frac{610}{615}\right) / \log\left(\frac{620}{625}\right)$$

The ratio, R, calculated from this equation may then be used to find a corresponding arterial oxygen saturation level for the fetus (i.e., fetal hemoglobin oxygen saturation level).

Fetal oxygen saturation level may also be calculated using the following equation (Equation 2):

$$S = \frac{\epsilon_{Hb}^{\lambda 2} R(B^{\lambda 2}/B^{\lambda 1}) - \epsilon_{Hb}^{\lambda 1}}{(\epsilon_{HbO}^{\lambda 1} - \epsilon_{Hb}^{\lambda 1}) - R(B^{\lambda 2}/B^{\lambda 1})(\epsilon_{HbO}^{\lambda 2} - \epsilon_{Hb}^{\lambda 2})}. \quad \text{Equation 2}$$

where:

S is the hemoglobin oxygen saturation,

R is the modulation ratio calculated using equation 1;

$\epsilon_{Hb}$ is the molar extinction coefficient for deoxygenated hemoglobin;

$\epsilon_{HbO}$ is the molar extinction coefficient for oxygenated hemoglobin; and B is a factor the can be estimated by solving the photon diffusion equation for the appropriate measurement geometry via the following expression (Equation 3):

$$B = \frac{1}{2}\left(\frac{3u'_s}{\mu_a^{initial}}\right)^{1/2}\left(1 - \frac{1}{1 + L(3u'^{initial}_3 u_a^{initial})^{\frac{1}{2}}}\right). \quad \text{Equation 3}$$

where:

L is the length;

$\mu_s$ is the scattering coefficient;

$\mu_a$ is the absorption coefficient;

$\mu_{s'}$ is the transport scattering coefficient, which is provided by the following expression (Equation 4):

$$\mu_s' = \mu_s(1-g), \quad \text{Equation 4}$$

where:

g is the anisotropy factor of scattering equal to the average cosine of the sing phase scattering function.

Further details regarding the calculations using equations 1, 2, 3, and 4 as well as how to determine fetal hemoglobin oxygen saturation levels are provided by Mannheimer, Paul D. et al., *Wavelength Selection for Low-Saturation Pulse Oximetry*, IEEE Transactions on Biomedical Engineering, Vol. 44, No. 3, March 1997, pp. 148-158 and Zourabian, Anna, et al., *Trans-abdominal Monitoring of Fetal Arterial Blood Oxygenation Using Pulse Oximetry*, Journal of Biomedical Optics, 5(4), pp. 391-405 (October 2000), both of which are incorporated by reference herein.

Figure 7B:
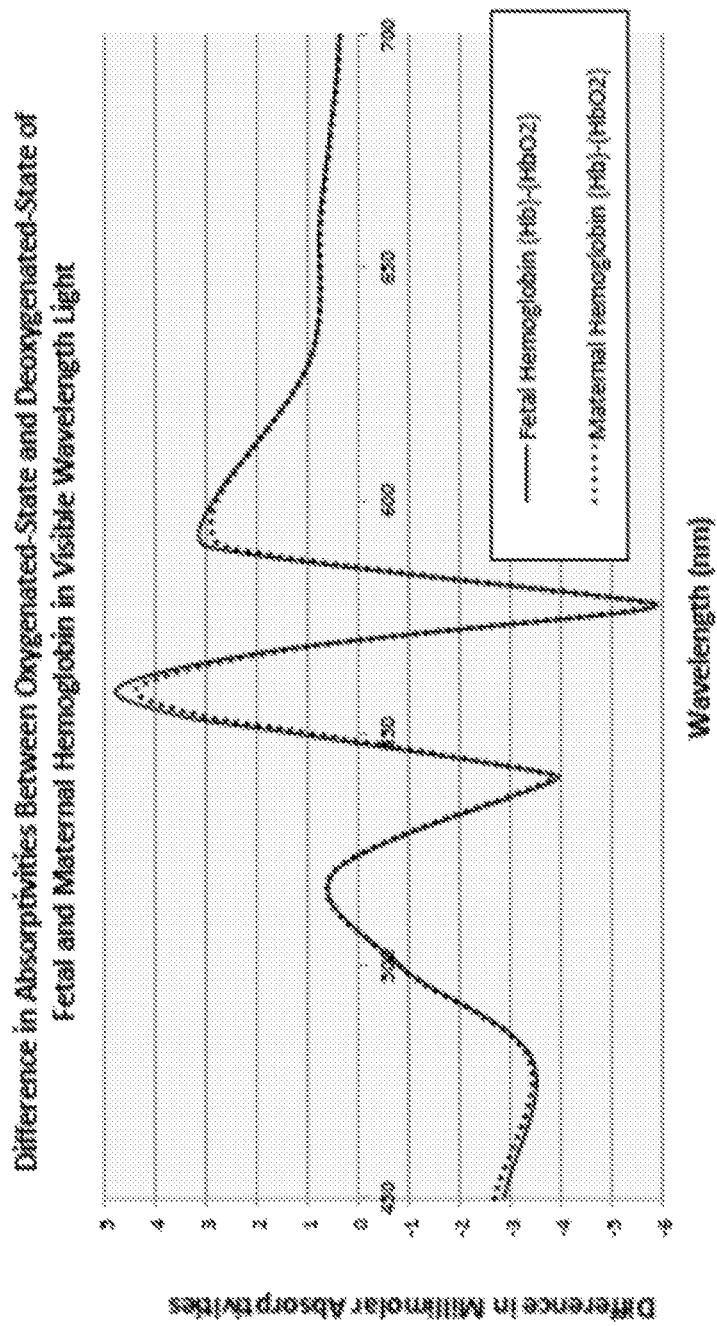
FIG. 7B depicts a graph that shows difference in absorptivities between oxygenated and deoxygenated state of fetal and the pregnant woman's hemoglobin in visible wavelengths of light, consistent with an embodiment of the invention.

FIG. 7A provides a table 700 of various hemoglobin measurements as a function of light wavelength shone into the blood of an adult donor and fetal blood obtained by puncture of the umbilical cord immediately after delivery[2]. The values in columns 2-8 of the table are measured in millimolar absorptivities (L*mmol$^{-1}$*cm$^{-1}$). More specifically, the first column of table 700 provides a list of wavelengths measured in nanometers (nm) ranging from 450 nm to 1000 nm, the second column of table 700 provides a fetal hemoglobin (HbF) measurement in a deoxyhemoglobin state (Hb), the third column of table 700 provides an adult hemoglobin (HbA) measurement in a deoxyhemoglobin state (Hb), the fourth column of table 700 provides a fetal hemoglobin measurement in an oxyhemoglobin state (HbO2), the fifth column of table 700 provides an adult hemoglobin measurement in an oxyhemoglobin state (HbO2), the sixth column of table 700 provides a value representing a difference between the fetal hemoglobin measurement deoxyhemoglobin state and the fetal hemoglobin measurement in an oxyhemoglobin state (Hb-HbO2), the seventh column of table 700 provides a value representing a difference between the adult hemoglobin measurement in a deoxyhemoglobin state and the adult hemoglobin measurement in an oxyhemoglobin state (Hb-HbO2), and the eighth column of table 700 provides a ratio of the fetal (Hb-HbO2)/HbO2. The data from table 700 is used to make the graphs depicted in FIGS. 7B and 7C.

[2] Experimental results are provided by Zijistra, W. G., et al. *Absorption Spectra of Human Fetal and Adult Oxyhemoglobin, De-Oxyhemoglobin, Carboxyhemoglobin, and Methemoglobin*, Clin. Chem. Vol. 39/9, pp. 1633-1638 (1991).

FIG. 7B depicts a graph 701 that shows difference in absorptivities between oxygenated (oxy-) and deoxygenated (deoxy-) state of fetal and the pregnant woman's hemoglobin in visible wavelengths of light from 450 nm to 700 nm wherein the green dashed line represents the difference in absorptivities between oxy- and deoxy-state of fetal hemoglobin as a function of wavelength and the red dashed line represents the difference in absorptivities between oxy- and deoxy-state of fetal hemoglobin of the pregnant woman as a function of wavelength.

Figure 7C:
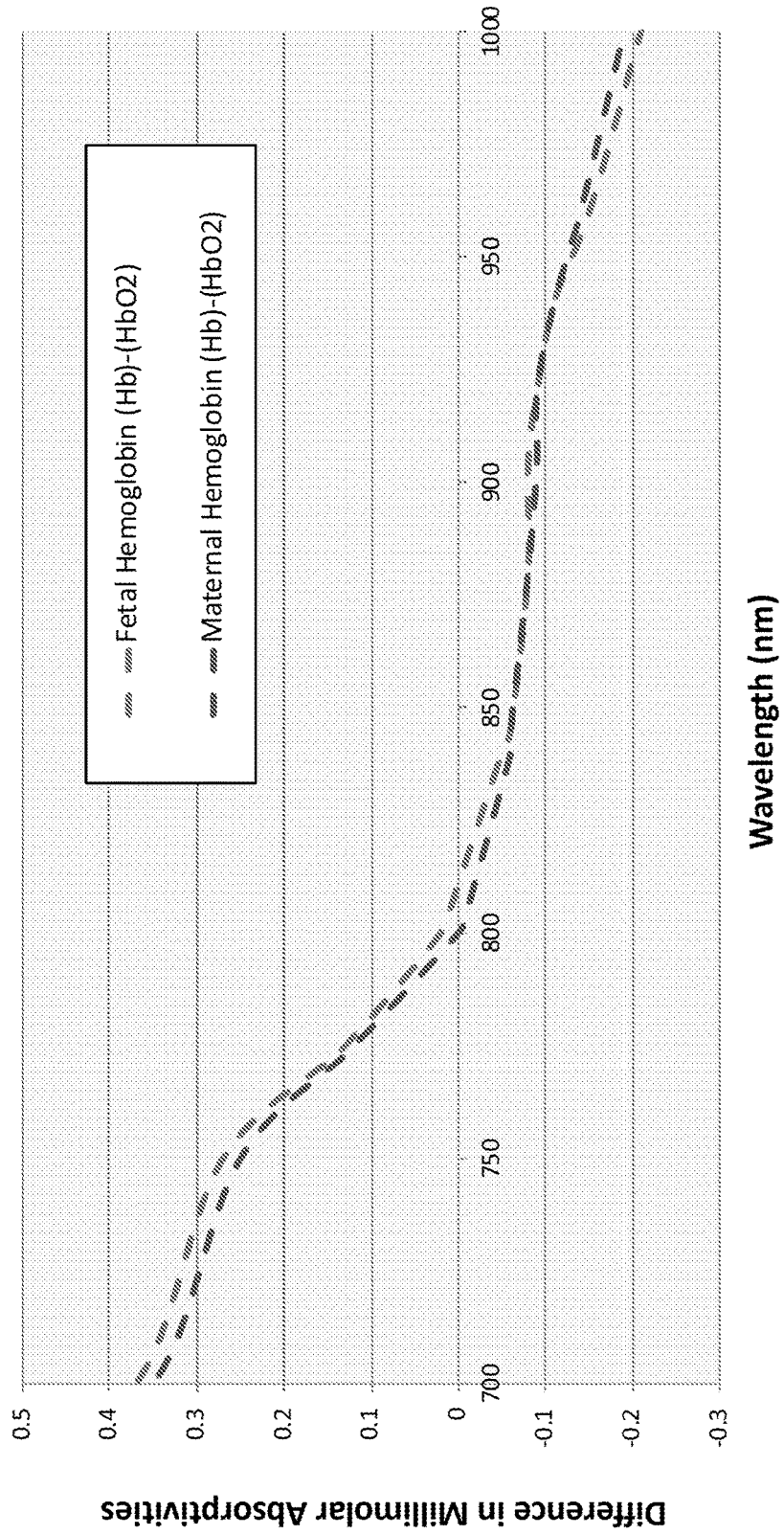
FIG. 7C depicts a graph that shows difference in absorptivities between oxy- and deoxy-state of fetal and the pregnant woman's hemoglobin in the near infrared (NIR) wavelengths of light, consistent with an embodiment of the invention.

FIG. 7C depicts a graph 702 that shows difference in absorptivities between oxy- and deoxy-state of fetal and the pregnant woman's hemoglobin in the near infrared (NIR) wavelengths of light from 700 nm to 1000 nm wherein the green dashed line represents the difference in absorptivities between oxy- and deoxy-state of fetal hemoglobin as a function of wavelength and the red dashed line represents the difference in absorptivities between oxy- and deoxy-state of fetal hemoglobin of the pregnant woman as a function of wavelength.

As can be seen in FIGS. 7A-7C, the greatest difference in absorbativities between the fetus and the pregnant woman occur within the wavelength ranges of approximately 700-

750 nm and 950-1000 nm. Thus, emission of infrared light in these wavelength ranges by fetal hemoglobin probe 115 is preferred so as to achieve optimal differentiation between the signal from the pregnant woman's hemoglobin and the fetus' hemoglobin.

All of the signal processing and analysis techniques described herein may employ one or more noise reduction techniques including, but not limited to, cancelling out of ambient noise as may occur from lights in the room where the pregnant mammal is located and the operation of electrical equipment near the pregnant mammal. Noise cancelling techniques may also include looking for non-periodic modulations of the electronic reflected signal and cancelling such modulations from the signal because it is unlikely that a non-periodic contribution to the signal is indicative of blood flow for either the pregnant mammal or the fetus.

Additionally, or alternatively, one or more of signal processing and analysis techniques described herein may be combined with one another. For example, an electronic reflected signal may be processed using process 401 and 402 so as to isolate the portion of the electronic reflected signal reflected by the fetus.

Figure 8A:
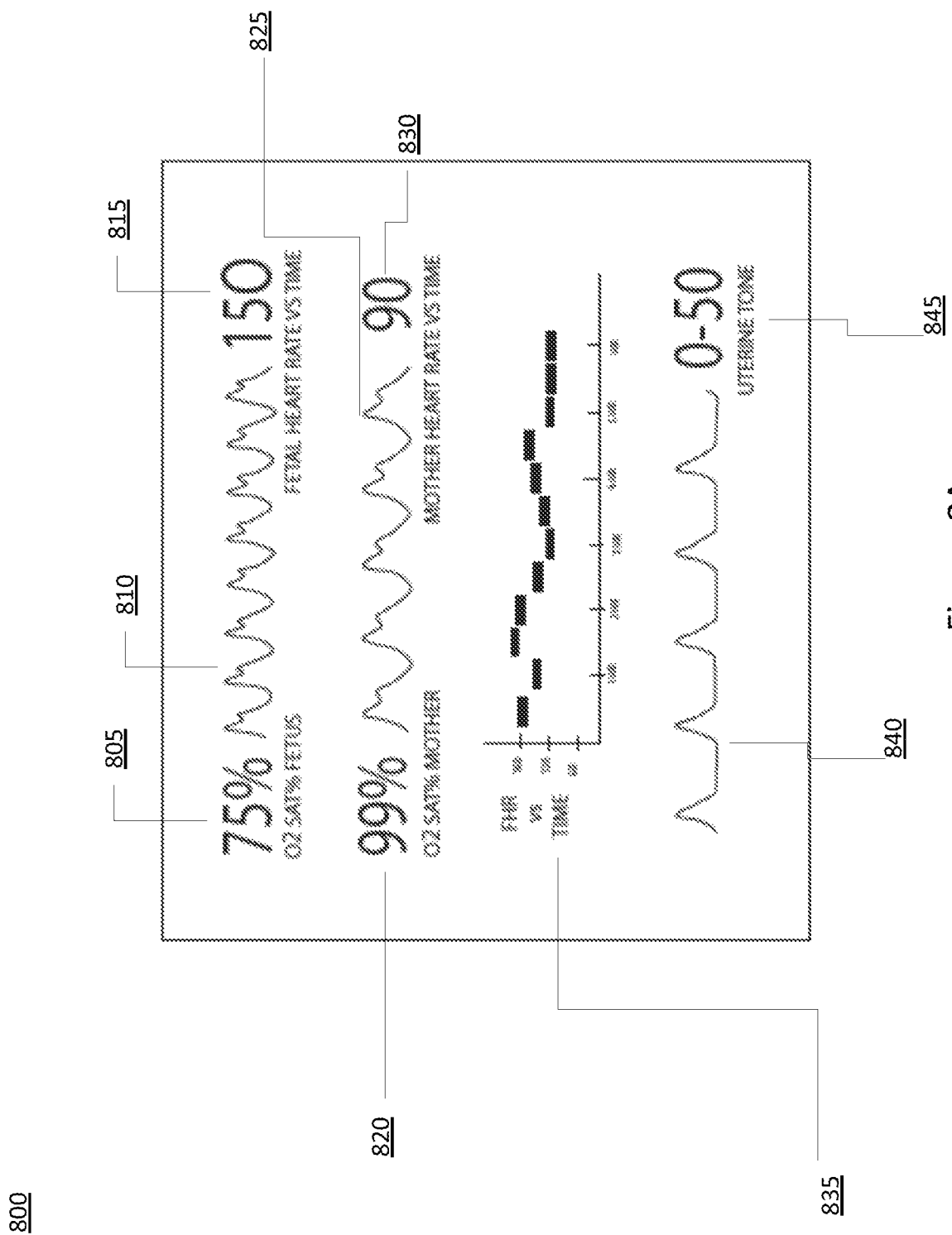
FIG. 8A provides an exemplary display that provides a level of fetal hemoglobin oxygen saturation along with other information regarding measurements of the pregnant mammal and fetus, consistent with an embodiment of the invention.

FIG. 8A provides an exemplary display 800 that provides a level of fetal hemoglobin oxygen saturation along with other information regarding measurements of the pregnant mammal and fetus. Display 800 provides a fetal hemoglobin oxygen saturation level 805 that is, for example, expressed as a percentage of 100, a continuous waveform (i.e., a plethysmogram) that represents the fetal heart rate over time 810, and a numerical value representing fetal heart rate represented in beats per minute 815. Display 800 also provides, the pregnant mammal's hemoglobin oxygen saturation level 820 that is, for example, expressed as a percentage of 100, a continuous waveform that represents the pregnant mammal's heart rate over time 825, a numerical value representing the pregnant woman's heart rate represented in beats per minute 830. Display 800 further provides a graph showing fetal heart rate over time as measured in hours 835, and an indication of uterine tone or pressure generated by uterine contractions as measured over time as measured in mmHG vs. time in minutes is provided as numerical value 845. The fetal heart rate over time graph 835 enables a physician to visually assess how the fetal heart rate changes during uterine contractions and may determine how well the fetus is tolerating the labor and delivery process. Uterine contraction numerical value 845 is a number from 0-50 calculated by a pressure sensor and it allows the physician to assess how long contractions are lasting, the intensity of the contractions, and the frequency of the contractions.

Figure 8B:
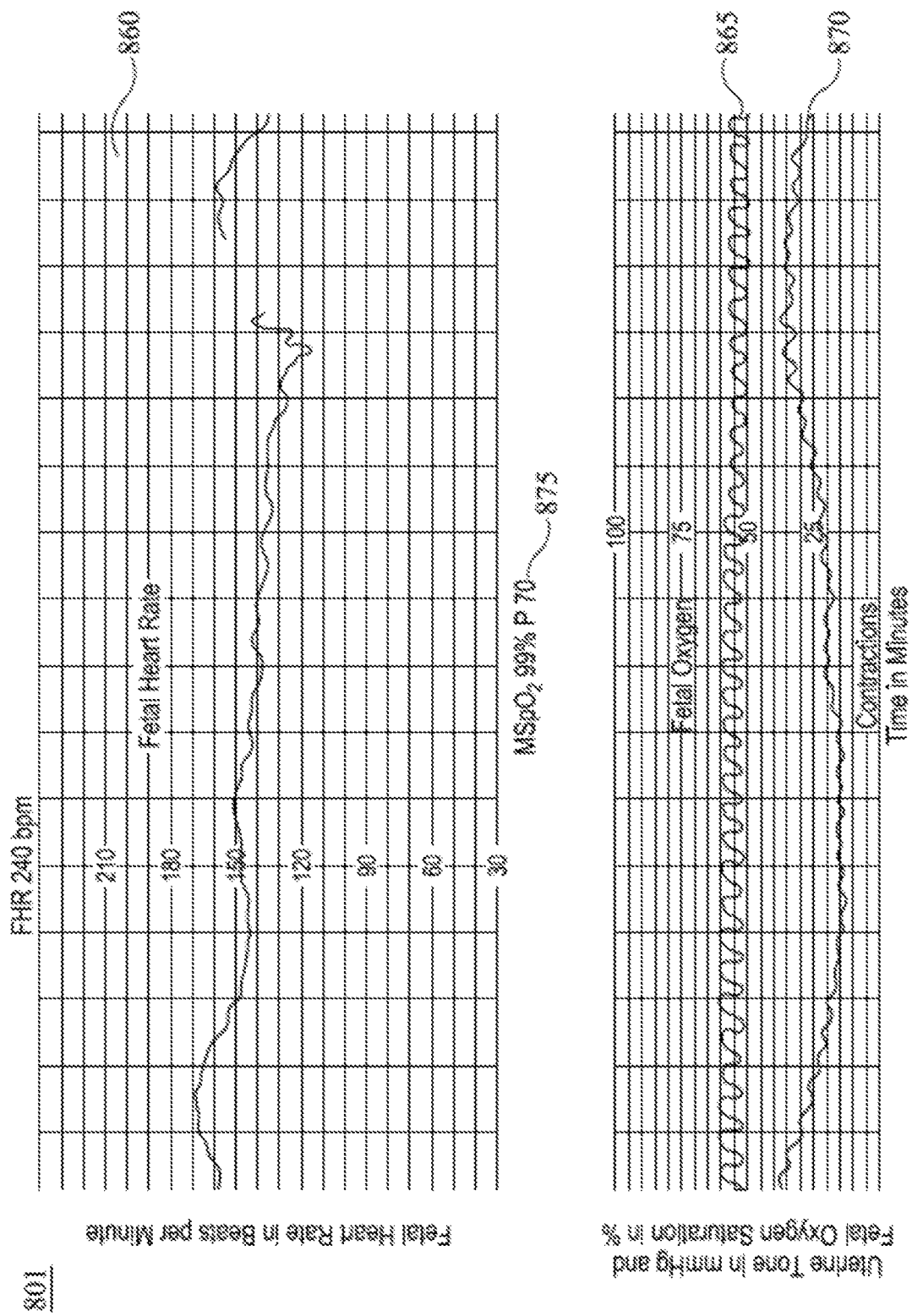
FIG. 8B provides an exemplary display of synchronized fetal heartbeat, fetal hemoglobin oxygen saturation rate, and uterine tone for corresponding moments in time, consistent with an embodiment of the invention.

FIG. 8B provides an exemplary display 801 of synchronized fetal heartbeat, fetal hemoglobin oxygen saturation rate, and uterine tone for corresponding moments in time. Display 801 is provided on a paper tape that has a Cartesian grid printed thereon with the vertical lines representing the passage of time (e.g., each vertical line represents a minute) and horizontal lines indicating a measurement scale. Paper tape of this type is not printed with a specific time scale as these tapes are typically used continuously through a monitoring period that may last many hours so, starting a time scale at 1, and progressing to 2, 3, 4, etc. is not relevant to the information being provided to the physician attending the pregnant mammal.

The upper graph of display 801 provides a graph of fetal heart rate as measured in beats per minute over time 860. The second graph of display 801 provides a graph of fetal hemoglobin oxygen concentration (termed "fetal oxygen" for brevity's sake on the graph) over time 865. The third graph of display 801 provides a graph of uterine tone (termed "contractions" for brevity's sake on the graph) 870. All three of graphs 860, 865 and 870 are synchronized in the time domain so that a measurement of fetal heartbeat for a particular moment in time corresponds with the fetal hemoglobin oxygen concentration level and the uterine tone at that particular moment in time. In this way, the attending doctor (or other medical professional) can simultaneously monitor pregnant mammal's uterine tone, the fetus' heartbeat and the fetus' hemoglobin oxygen concentration level during, for example, the labor and delivery process, to assess the health of the fetus.

Hence, systems, devices, and methods for determining fetal oxygen level have been herein disclosed. In some embodiments, use of the systems, devices, and methods described herein may be particularly useful during the labor and delivery of the fetus (e.g., during the first and/or second stage of labor) because it is difficult to assess fetal health during the labor and delivery process.

I claim:

1. A fetal monitoring system, comprising:
a detector adapted to detect light reflected from an abdomen of a pregnant mammal and a fetus contained therein, the reflected light corresponding to incident light projected into the pregnant mammal's abdomen and the fetus by a light source, the detector being further adapted to convert the detected light into a reflected electronic signal and communicate the reflected electronic signal to a processor; and
the processor in communication with the detector, the processor being configured to:
  (i) isolate a portion of the reflected electronic signal that corresponds to light reflected from the fetus from the reflected electronic signal, the isolation comprising:
    (a) receiving the reflected electronic signal from the detector over a first time domain,
    (b) receiving a heartbeat signal of the fetus over a second time domain,
    (c) synchronizing the reflected electronic signal and the fetal heartbeat signal over the first and second time domains; and
    (d) examining portions of the synchronized electronic reflected signal that correspond in time with individual heartbeats of the fetus as indicated by the received heartbeat signal for the fetus;
  (ii) analyze the isolated portion of the reflected electronic signal to determine a hemoglobin oxygen saturation level of the fetus; and
  (iii) facilitate provision of an indication of the hemoglobin oxygen saturation level of the fetus to a display device.

2. The system of claim 1, further comprising:
the light source configured to project light into the abdomen of the pregnant mammal toward the fetus contained therein.

3. The system of claim 2, further comprising:
an adjustment mechanism coupled to the light source and configured to adjust at least one of (i) a frequency of light emitted by the light source, (ii) an incident angle of the light emitted by the light source, and (iii) a focus of a beam of the light.

4. The system of claim 2, further comprising:
an additional light source configured to project light into the abdomen of the pregnant mammal toward the fetus contained therein.

5. The system of claim 2, wherein the light source emits a light of a wavelength within a range at least one of between 700 nm and 740 nm and between 800 and 900 nm.

6. The system of claim 1, further comprising:
an additional detector configured to (i) detect light reflected from the pregnant mammal's abdomen, (ii) convert the detected light into an additional reflected electronic signal, and (iii) communicate the additional reflected electronic signal to the processor.

7. The system of claim 1, further comprising:
a temperature probe configured to measure a temperature of the pregnant mammal's abdomen and communicate the temperature measurement to the processor, the processor being further configured to provide an indication of the measured temperature to the display device.

8. The system of claim 1, further comprising:
an ultrasonic detector configured to detect ultrasonic emissions of the pregnant mammal's abdomen and fetus and to communicate a signal corresponding to the detected ultrasonic emissions to the processor.

9. The system of claim 1, further comprising:
an ultrasonic detector adapted to detect ultrasonic emissions of the pregnant mammal's abdomen and fetus caused by transient thermoelastic expansion resultant from an interaction of the pregnant mammal's abdomen and the fetus' tissue to light emitted from the light source and communicate a signal corresponding to the detected ultrasonic emissions to the processor.

10. The system of claim 1, further comprising:
a uterine contraction measurement device configured to measure changes in a muscular state of the pregnant mammal's uterus and to communicate the measured changes to the processor, the processor being further configured to provide an indication of the measured changes to the display device.

11. The system of claim 1, further comprising:
a transceiver communicatively coupled to at least one of the detector and the processor, the transceiver being configured to receive the reflected electronic signal from the detector and to communicate the received reflected electronic signal to the processor.

12. The system of claim 1, further comprising:
a receiver communicatively coupled to the detector, a source of the fetal heartbeat signal, and the processor, the receiver being configured to receive the heartbeat signal for the fetus from the source of the fetal heartbeat signal and the reflected electronic signal from the detector and to communicate the received heartbeat signal for the fetus and reflected electronic signal to the processor.

13. The system of claim 1, wherein the processor further receives an indication of the hemoglobin oxygen saturation level of the pregnant mammal, the processor being further configured to analyze the indication of the oxygen saturation level to determine a heartbeat signal for the pregnant mammal.

14. A method for determining a fetal hemoglobin oxygen saturation level, the method comprising:
receiving, by a processor, a heartbeat signal for a fetus over a first time domain from a monitor communicatively coupled to the processor;
receiving, by the processor, a reflected electronic signal from a detector communicatively coupled to the processor, the reflected electronic signal corresponding to light reflected from a pregnant mammal's abdomen and a fetus contained therein, the reflected light being a portion of light projected, by a light source, into the pregnant mammal's abdomen and fetus contained therein, wherein the reflected light has been converted, by the detector, into the reflected electronic signal;
processing, by the processor, the reflected electronic signal to isolate a portion of the reflected electronic signal that is reflected from the fetus, the processing of the reflected electronic signal comprising:
synchronizing the electronic reflected signal and the fetal heartbeat signal over the first and second time domains; and
examining, by the processor, portions of the synchronized electronic reflected signal that correspond in time with individual heartbeats of the fetus as indicated by the received heartbeat signal for the fetus;
analyzing, by the processor, the isolated portion of the reflected electronic signal to determine a fetal hemoglobin oxygen saturation level of the fetus; and
facilitating, by the processor, provision of an indication of the fetal hemoglobin oxygen saturation level to a display device.

15. The method of claim 14, further comprising:
projecting, by the light source, the incident light into the pregnant mammal's abdomen.

16. The method of claim 15, further comprising:
adjusting at least one of a frequency of the incident light, an incident angle of the incident light, and a focus of a beam of the incident light.

17. The method of claim 15, further comprising:
determining whether the reflected electronic signal is of sufficient strength; and
adjusting the light source responsively to a determination that the reflected electronic signal is not of sufficient strength.

18. The method of claim 14, further comprising:
determining whether the reflected electronic signal is of sufficient strength; and
adjusting the detector responsively to a determination that the reflected electronic signal is not of sufficient strength.

19. The method of claim 14, further comprising:
receiving, by the processor, a signal indicating ultrasonic emissions of the pregnant mammal's abdomen and fetus from an ultrasonic detector in communication with the processor, the ultrasonic emissions of the pregnant mammal's abdomen and fetus being caused by transient thermoelastic expansion resultant from an interaction of the pregnant mammal's abdomen and the fetus' tissue to light emitted from the light source.

20. The method of claim 14, further comprising:
processing, by the processor, the reflected electronic signal to determine a muscular state of the pregnant mammal's uterus; and
facilitating, by the processor, provision of an indication of the muscular state of the pregnant mammal's uterus to the display device.

21. A computer for determining a fetal hemoglobin oxygen saturation level comprising:
a processor, the processor being configured to:
receive a heartbeat signal for a pregnant mammal from a monitor communicatively coupled to the processor;
receive a reflected electronic signal from a detector communicatively coupled to the processor, the reflected electronic signal corresponding to light reflected from a pregnant mammal's abdomen and a fetus contained therein, the reflected light being a portion of light projected, by a light source, into the pregnant mammal's abdomen and fetus contained therein, wherein the reflected light has been converted, by the detector, into the reflected electronic signal;

isolate a portion of the reflected electronic signal reflected from the fetus by:

receiving the reflected electronic signal from the detector over a first time domain receiving a heartbeat signal of the fetus over a second time domain, synchronizing the reflected electronic signal and the fetal heartbeat signal over the first and second time domains; and examining portions of the synchronized electronic reflected signal that correspond in time with individual heartbeats of the fetus as indicated by the received heartbeat signal for the fetus;

analyze the isolated portion of the reflected electronic signal to determine a fetal hemoglobin oxygen saturation level of the fetus; and facilitate provision of an indication of the fetal hemoglobin oxygen saturation level to a display device.

22. The computer of claim 21, the processor being further configured to:

receive a signal indicating ultrasonic emissions of the pregnant mammal's abdomen and fetus from an ultrasonic detector in communication with the processor, the ultrasonic emissions of the pregnant mammal's abdomen and fetus being caused by transient thermoelastic expansion resultant from an interaction of the pregnant mammal's abdomen and the fetus' tissue to light emitted from the light source.

23. The computer of claim 21, the processor being further configured to:

process the reflected electronic signal to determine a muscular state of the pregnant mammal's uterus; and facilitate provision of an indication of the muscular state of the pregnant mammal's uterus to the display device.

\* \* \* \* \*